(12) United States Patent
Sexton et al.

(10) Patent No.: US 12,031,094 B2
(45) Date of Patent: *Jul. 9, 2024

(54) ASSEMBLIES AND METHODS FOR ENHANCING FLUID CATALYTIC CRACKING (FCC) PROCESSES DURING THE FCC PROCESS USING SPECTROSCOPIC ANALYZERS

(71) Applicant: MARATHON PETROLEUM COMPANY LP, Findlay, OH (US)

(72) Inventors: Jeffrey A. Sexton, Findlay, OH (US); Roy Roger Bledsoe, Jr., Findlay, OH (US); Lance T. Campbell, Findlay, OH (US); Randy N. Ridge, Findlay, OH (US); Brian K. Wilt, Findlay, OH (US)

(73) Assignee: MARATHON PETROLEUM COMPANY LP, Findlay, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/213,233

(22) Filed: Jun. 22, 2023

(65) Prior Publication Data
US 2023/0357649 A1 Nov. 9, 2023

Related U.S. Application Data

(63) Continuation of application No. 18/052,780, filed on Nov. 4, 2022, now Pat. No. 11,702,600, which is a
(Continued)

(51) Int. Cl.
*C10G 11/00* (2006.01)
*G01N 21/31* (2006.01)
(Continued)

(52) U.S. Cl.
CPC ............ *C10G 11/00* (2013.01); *G01N 21/31* (2013.01); *G01N 33/28* (2013.01); *G06F 30/28* (2020.01);
(Continued)

(58) Field of Classification Search
CPC ........ G06F 30/28; G01N 21/31; G01N 33/28; C10G 11/00; C10G 2300/4012; C10G 2300/4006
See application file for complete search history.

(56) References Cited

U.S. PATENT DOCUMENTS

| 981,434 A | 1/1911 | Lander |
| 1,526,301 A | 2/1925 | Stevens |
(Continued)

FOREIGN PATENT DOCUMENTS

| AT | 11772 U1 | 4/2011 |
| BR | PI0701518 | 11/2008 |
(Continued)

OTHER PUBLICATIONS

"Development of Model Equations for Predicting Gasoline Blending Properties", Odula et al., American Journal of Chemical Engineering, vol. 3, No. 2-1, 2015, pp. 9-17.
(Continued)

*Primary Examiner* — Sang H Nguyen
(74) *Attorney, Agent, or Firm* — Womble Bond Dickinson (US) LLP

(57) ABSTRACT

Assemblies and methods to enhance a fluid catalytic cracking (FCC) process associated with a refining operation, during the FCC process, may include supplying a hydrocarbon feedstock to first processing units associated with the refining operation. The assemblies and methods also may include conditioning a hydrocarbon feedstock and unit material samples, and analyzing the samples via one or more spectroscopic analyzers. The assemblies and methods further may include prescriptively controlling, via one or more FCC process controllers, based at least in part on the hydrocarbon feedstock properties and the unit material properties, the FCC processing assembly, so that the prescriptively controlling results in causing the FCC process to
(Continued)

produce intermediate materials, the unit materials, and/or the downstream materials having properties within selected ranges of target properties, thereby to cause the FCC process to achieve material outputs that more accurately and responsively converge on one or more of the target properties.

43 Claims, 21 Drawing Sheets

Related U.S. Application Data continuation-in-part of application No. 17/652,431, filed on Feb. 24, 2022.

(60) Provisional application No. 63/268,875, filed on Mar. 4, 2022, provisional application No. 63/268,827, filed on Mar. 3, 2022, provisional application No. 63/268,456, filed on Feb. 24, 2022, provisional application No. 63/153,452, filed on Feb. 25, 2021.

(51) Int. Cl.
*G01N 33/28* (2006.01)
*G06F 30/28* (2020.01)

(52) U.S. Cl.
CPC .............. *C10G 2300/4006* (2013.01); *C10G 2300/4012* (2013.01)

(56) References Cited

U.S. PATENT DOCUMENTS

| | | |
|---|---|---|
| 1,572,922 A | 2/1926 | Govers et al. |
| 1,867,143 A | 7/1932 | Fohl |
| 2,401,570 A | 6/1946 | Koehler |
| 2,498,442 A | 2/1950 | Morey |
| 2,516,097 A | 7/1950 | Woodham et al. |
| 2,686,728 A | 8/1954 | Wallace |
| 2,691,621 A | 10/1954 | Gagle |
| 2,691,773 A | 10/1954 | Lichtenberger, V |
| 2,731,282 A | 1/1956 | Mcmanus et al. |
| 2,740,616 A | 4/1956 | Walden |
| 2,792,908 A | 5/1957 | Glanzer |
| 2,804,165 A | 8/1957 | Blomgren |
| 2,867,913 A | 1/1959 | Faucher |
| 2,888,239 A | 5/1959 | Slemmons |
| 2,909,482 A | 10/1959 | Williams et al. |
| 2,925,144 A | 2/1960 | Kroll |
| 2,963,423 A | 12/1960 | Birchfield |
| 3,063,681 A | 11/1962 | Duguid |
| 3,070,990 A | 1/1963 | Stanley |
| 3,109,481 A | 11/1963 | Yahnke |
| 3,167,305 A | 1/1965 | Backx et al. |
| 3,188,184 A | 6/1965 | Rice et al. |
| 3,199,876 A | 8/1965 | Magos et al. |
| 3,203,460 A | 8/1965 | Kuhne |
| 3,279,441 A | 10/1966 | Lippert et al. |
| 3,307,574 A | 3/1967 | Anderson |
| 3,364,134 A | 1/1968 | Hamblin |
| 3,400,049 A | 9/1968 | Wolfe |
| 3,545,411 A | 12/1970 | Vollradt |
| 3,660,057 A | 5/1972 | Ilnyckyj |
| 3,719,027 A | 3/1973 | Salka |
| 3,720,601 A | 3/1973 | Coonradt |
| 3,771,638 A | 11/1973 | Schneider et al. |
| 3,775,294 A | 11/1973 | Peterson |
| 3,795,607 A | 3/1974 | Adams |
| 3,838,036 A | 9/1974 | Stine et al. |
| 3,839,484 A | 10/1974 | Zimmerman, Jr. |
| 3,840,209 A | 10/1974 | James |
| 3,841,144 A | 10/1974 | Baldwin |
| 3,854,843 A | 12/1974 | Penny |
| 3,874,399 A | 4/1975 | Ishihara |
| 3,901,951 A | 8/1975 | Nishizaki |
| 3,906,780 A | 9/1975 | Baldwin |
| 3,912,307 A | 10/1975 | Totman |
| 3,928,172 A | 12/1975 | Davis et al. |
| 3,937,660 A | 2/1976 | Yates et al. |
| 4,006,075 A | 2/1977 | Luckenbach |
| 4,017,214 A | 4/1977 | Smith |
| 4,066,425 A | 1/1978 | Nett |
| 4,085,078 A | 4/1978 | McDonald |
| 4,144,759 A | 3/1979 | Slowik |
| 4,149,756 A | 4/1979 | Tackett |
| 4,151,003 A | 4/1979 | Smith et al. |
| 4,167,492 A | 9/1979 | Varady |
| 4,176,052 A | 11/1979 | Bruce et al. |
| 4,217,116 A | 8/1980 | Seever |
| 4,260,068 A | 4/1981 | McCarthy et al. |
| 4,299,687 A | 11/1981 | Myers et al. |
| 4,302,324 A | 11/1981 | Chen et al. |
| 4,308,968 A | 1/1982 | Thiltgen et al. |
| 4,328,947 A | 5/1982 | Reimpell et al. |
| 4,332,671 A | 6/1982 | Boyer |
| 4,340,204 A | 7/1982 | Heard |
| 4,353,812 A | 10/1982 | Lomas et al. |
| 4,357,603 A | 11/1982 | Roach et al. |
| 4,392,870 A | 7/1983 | Chieffo et al. |
| 4,404,095 A | 9/1983 | Haddad et al. |
| 4,422,925 A | 12/1983 | Williams et al. |
| 4,434,044 A | 2/1984 | Busch et al. |
| 4,439,533 A | 3/1984 | Lomas et al. |
| 4,468,975 A | 9/1984 | Sayles et al. |
| 4,482,451 A | 11/1984 | Kemp |
| 4,495,063 A | 1/1985 | Walters et al. |
| 4,539,012 A | 9/1985 | Ohzeki et al. |
| 4,554,313 A | 11/1985 | Hagenbach et al. |
| 4,554,799 A | 11/1985 | Pallanch |
| 4,570,942 A | 2/1986 | Diehl et al. |
| 4,601,303 A | 7/1986 | Jensen |
| 4,615,792 A | 10/1986 | Greenwood |
| 4,621,062 A | 11/1986 | Stewart et al. |
| 4,622,210 A | 11/1986 | Hirschberg et al. |
| 4,624,771 A | 11/1986 | Lane et al. |
| 4,647,313 A | 3/1987 | Clementoni |
| 4,654,748 A | 3/1987 | Rees |
| 4,661,241 A | 4/1987 | Dabkowski et al. |
| 4,673,490 A | 6/1987 | Subramanian et al. |
| 4,674,337 A | 6/1987 | Jonas |
| 4,684,759 A | 8/1987 | Lam |
| 4,686,027 A | 8/1987 | Bonilla et al. |
| 4,728,348 A | 3/1988 | Nelson et al. |
| 4,733,888 A | 3/1988 | Toelke |
| 4,741,819 A | 5/1988 | Robinson et al. |
| 4,764,347 A | 8/1988 | Milligan |
| 4,765,631 A | 8/1988 | Kohnen et al. |
| 4,771,176 A | 9/1988 | Scheifer et al. |
| 4,816,137 A | 3/1989 | Swint et al. |
| 4,820,404 A | 4/1989 | Owen |
| 4,824,016 A | 4/1989 | Cody et al. |
| 4,844,133 A | 7/1989 | von Meyerinck et al. |
| 4,844,927 A | 7/1989 | Morris et al. |
| 4,849,182 A | 7/1989 | Luetzelschwab |
| 4,854,855 A | 8/1989 | Rajewski |
| 4,875,994 A | 10/1989 | Haddad et al. |
| 4,877,513 A | 10/1989 | Haire et al. |
| 4,798,463 A | 11/1989 | Koshi |
| 4,901,751 A | 2/1990 | Story et al. |
| 4,914,249 A | 4/1990 | Benedict |
| 4,916,938 A | 4/1990 | Aikin et al. |
| 4,917,790 A | 4/1990 | Owen |
| 4,923,834 A | 5/1990 | Lomas |
| 4,940,900 A | 7/1990 | Lambert |
| 4,957,511 A | 9/1990 | Ljusberg-Wahren |
| 4,960,503 A | 10/1990 | Haun et al. |
| 4,963,745 A | 10/1990 | Maggard |
| 4,972,867 A | 11/1990 | Ruesch |
| 5,000,841 A | 3/1991 | Owen |
| 5,002,459 A | 3/1991 | Swearingen et al. |
| 5,008,653 A | 4/1991 | Kidd et al. |
| 5,009,768 A | 4/1991 | Galiasso et al. |
| 5,013,537 A | 5/1991 | Patarin et al. |
| 5,022,266 A | 6/1991 | Cody et al. |

(56) References Cited

U.S. PATENT DOCUMENTS

| | | |
|---|---|---|
| 5,032,154 A | 7/1991 | Wright |
| 5,034,115 A | 7/1991 | Avidan |
| 5,045,177 A | 9/1991 | Cooper et al. |
| 5,050,603 A | 9/1991 | Stokes et al. |
| 5,053,371 A | 10/1991 | Williamson |
| 5,056,758 A | 10/1991 | Bramblet |
| 5,059,305 A | 10/1991 | Sapre |
| 5,061,467 A | 10/1991 | Johnson et al. |
| 5,066,049 A | 11/1991 | Staples |
| 5,076,910 A | 12/1991 | Rush |
| 5,082,985 A | 1/1992 | Crouzet et al. |
| 5,096,566 A | 3/1992 | Dawson et al. |
| 5,097,677 A | 3/1992 | Holtzapple |
| 5,111,882 A | 5/1992 | Tang et al. |
| 5,112,357 A | 5/1992 | Bjerklund |
| 5,114,562 A | 5/1992 | Haun et al. |
| 5,115,686 A | 5/1992 | Walker et al. |
| 5,121,337 A | 6/1992 | Brown |
| 5,128,109 A | 7/1992 | Owen |
| 5,128,292 A | 7/1992 | Lomas |
| 5,129,624 A | 7/1992 | Icenhower et al. |
| 5,138,891 A | 8/1992 | Johnson |
| 5,139,649 A | 8/1992 | Owen et al. |
| 5,145,785 A | 9/1992 | Maggard et al. |
| 5,149,261 A | 9/1992 | Suwa et al. |
| 5,154,558 A | 10/1992 | McCallion |
| 5,160,426 A | 11/1992 | Avidan |
| 5,170,911 A | 12/1992 | Della Riva |
| 5,174,250 A | 12/1992 | Lane |
| 5,174,345 A | 12/1992 | Kesterman et al. |
| 5,178,363 A | 1/1993 | Icenhower et al. |
| 5,196,110 A | 3/1993 | Swart et al. |
| 5,201,850 A | 4/1993 | Lenhardt et al. |
| 5,203,370 A | 4/1993 | Block et al. |
| 5,211,838 A | 5/1993 | Staubs et al. |
| 5,212,129 A | 5/1993 | Lomas |
| 5,221,463 A | 6/1993 | Kamienski et al. |
| 5,223,714 A | 6/1993 | Maggard |
| 5,225,679 A | 7/1993 | Clark et al. |
| 5,230,498 A | 7/1993 | Wood et al. |
| 5,235,999 A | 8/1993 | Lindquist et al. |
| 5,236,765 A | 8/1993 | Cordia et al. |
| 5,243,546 A | 9/1993 | Maggard |
| 5,246,860 A | 9/1993 | Hutchins et al. |
| 5,246,868 A | 9/1993 | Busch et al. |
| 5,248,408 A | 9/1993 | Owen |
| 5,250,807 A | 10/1993 | Sontvedt |
| 5,257,530 A | 11/1993 | Beattie et al. |
| 5,258,115 A | 11/1993 | Heck et al. |
| 5,258,117 A | 11/1993 | Kolstad et al. |
| 5,262,645 A | 11/1993 | Lambert et al. |
| 5,263,682 A | 11/1993 | Covert et al. |
| 5,301,560 A | 4/1994 | Anderson et al. |
| 5,302,294 A | 4/1994 | Schubert |
| 5,316,448 A | 5/1994 | Ziegler et al. |
| 5,320,671 A | 6/1994 | Schilling |
| 5,326,074 A | 7/1994 | Spock et al. |
| 5,328,505 A | 7/1994 | Schilling |
| 5,328,591 A | 7/1994 | Raterman |
| 5,332,492 A | 7/1994 | Maurer et al. |
| 5,338,439 A | 8/1994 | Owen et al. |
| 5,348,645 A | 9/1994 | Maggard et al. |
| 5,349,188 A | 9/1994 | Maggard |
| 5,349,189 A | 9/1994 | Maggard |
| 5,354,451 A | 10/1994 | Goldstein et al. |
| 5,354,453 A | 10/1994 | Bhatia |
| 5,361,643 A | 11/1994 | Boyd et al. |
| 5,362,965 A | 11/1994 | Maggard |
| 5,370,146 A | 12/1994 | King et al. |
| 5,370,790 A | 12/1994 | Maggard et al. |
| 5,372,270 A | 12/1994 | Rosenkrantz |
| 5,372,352 A | 12/1994 | Smith et al. |
| 5,381,002 A | 1/1995 | Morrow et al. |
| 5,388,805 A | 2/1995 | Bathrick et al. |
| 5,389,232 A | 2/1995 | Adewuyi et al. |
| 5,404,015 A | 4/1995 | Chimenti et al. |
| 5,415,025 A | 5/1995 | Bartman et al. |
| 5,416,323 A | 5/1995 | Hoots et al. |
| 5,417,843 A | 5/1995 | Swart et al. |
| 5,417,846 A | 5/1995 | Renard |
| 5,423,446 A | 6/1995 | Johnson |
| 5,431,067 A | 7/1995 | Anderson et al. |
| 5,433,120 A | 7/1995 | Boyd et al. |
| 5,435,436 A | 7/1995 | Manley et al. |
| 5,443,716 A | 8/1995 | Anderson et al. |
| 5,446,681 A | 8/1995 | Gethner et al. |
| 5,452,232 A | 9/1995 | Espinosa et al. |
| RE35,046 E | 10/1995 | Hettinger et al. |
| 5,459,677 A | 10/1995 | Kowalski et al. |
| 5,472,875 A | 12/1995 | Monticello |
| 5,474,607 A | 12/1995 | Holleran |
| 5,475,612 A | 12/1995 | Espinosa et al. |
| 5,476,117 A | 12/1995 | Pakula |
| 5,490,085 A | 2/1996 | Lambert et al. |
| 5,492,617 A | 2/1996 | Trimble et al. |
| 5,494,079 A | 2/1996 | Tiedemann |
| 5,507,326 A | 4/1996 | Cadman et al. |
| 5,510,265 A | 4/1996 | Monticello |
| 5,516,969 A | 5/1996 | Krasznai et al. |
| 5,532,487 A | 7/1996 | Brearley et al. |
| 5,540,893 A | 7/1996 | English |
| 5,549,814 A | 8/1996 | Zinke |
| 5,556,222 A | 9/1996 | Chen |
| 5,559,295 A | 9/1996 | Sheryll |
| 5,560,509 A | 10/1996 | Laverman et al. |
| 5,569,808 A | 10/1996 | Cansell et al. |
| 5,573,032 A | 11/1996 | Lenz et al. |
| 5,584,985 A | 12/1996 | Lomas |
| 5,596,196 A | 1/1997 | Cooper et al. |
| 5,600,134 A | 2/1997 | Ashe et al. |
| 5,647,961 A | 7/1997 | Lofland |
| 5,652,145 A | 7/1997 | Cody et al. |
| 5,675,071 A | 10/1997 | Cody et al. |
| 5,684,580 A | 11/1997 | Cooper et al. |
| 5,699,269 A | 12/1997 | Ashe et al. |
| 5,699,270 A | 12/1997 | Ashe et al. |
| 5,712,481 A | 1/1998 | Welch et al. |
| 5,712,797 A | 1/1998 | Descales et al. |
| 5,713,401 A | 2/1998 | Weeks |
| 5,716,055 A | 2/1998 | Wilkinson et al. |
| 5,717,209 A | 2/1998 | Bigman et al. |
| 5,740,073 A | 4/1998 | Bages et al. |
| 5,744,024 A | 4/1998 | Sullivan, III et al. |
| 5,744,702 A | 4/1998 | Roussis et al. |
| 5,746,906 A | 5/1998 | McHenry et al. |
| 5,758,514 A | 6/1998 | Genung et al. |
| 5,763,883 A | 6/1998 | Descales et al. |
| 5,800,697 A | 9/1998 | Lengemann |
| 5,817,517 A | 10/1998 | Perry et al. |
| 5,822,058 A | 10/1998 | Adler-Golden et al. |
| 5,834,539 A | 11/1998 | Krivohlavek |
| 5,837,130 A | 11/1998 | Crossland |
| 5,853,455 A | 12/1998 | Gibson |
| 5,856,869 A | 1/1999 | Cooper et al. |
| 5,858,207 A | 1/1999 | Lomas |
| 5,858,210 A | 1/1999 | Richardson |
| 5,858,212 A | 1/1999 | Darcy |
| 5,861,228 A | 1/1999 | Descales et al. |
| 5,862,060 A | 1/1999 | Murray, Jr. |
| 5,865,441 A | 2/1999 | Orlowski |
| 5,883,363 A | 3/1999 | Motoyoshi et al. |
| 5,885,439 A | 3/1999 | Glover |
| 5,892,228 A | 4/1999 | Cooper et al. |
| 5,895,506 A | 4/1999 | Cook et al. |
| 5,916,433 A | 6/1999 | Tejada et al. |
| 5,919,354 A | 7/1999 | Bartek |
| 5,935,415 A | 8/1999 | Haizmann et al. |
| 5,940,176 A | 8/1999 | Knapp |
| 5,972,171 A | 10/1999 | Ross et al. |
| 5,979,491 A | 11/1999 | Gonsior |
| 5,997,723 A | 12/1999 | Wiehe et al. |
| 6,015,440 A | 1/2000 | Noureddini |
| 6,025,305 A | 2/2000 | Aldrich et al. |
| 6,026,841 A | 2/2000 | Kozik |

(56) References Cited

U.S. PATENT DOCUMENTS

| | | | |
|---|---|---|---|
| 6,047,602 A | 4/2000 | Lynnworth |
| 6,056,005 A | 5/2000 | Piotrowski et al. |
| 6,062,274 A | 5/2000 | Pettesch |
| 6,063,263 A | 5/2000 | Palmas |
| 6,063,265 A | 5/2000 | Chiyoda et al. |
| 6,070,128 A | 5/2000 | Descales et al. |
| 6,072,576 A | 6/2000 | McDonald et al. |
| 6,076,864 A | 6/2000 | Levivier et al. |
| 6,087,662 A | 7/2000 | Wilt et al. |
| 6,093,867 A | 7/2000 | Ladwig et al. |
| 6,099,607 A | 8/2000 | Haslebacher |
| 6,099,616 A | 8/2000 | Jenne et al. |
| 6,102,655 A | 8/2000 | Kreitmeier |
| 6,105,441 A | 8/2000 | Conner et al. |
| 6,107,631 A | 8/2000 | He |
| 6,117,812 A | 9/2000 | Gao et al. |
| 6,130,095 A | 10/2000 | Shearer |
| 6,140,647 A | 10/2000 | Welch et al. |
| 6,153,091 A | 11/2000 | Sechrist et al. |
| 6,155,294 A | 12/2000 | Cornford et al. |
| 6,162,644 A | 12/2000 | Choi et al. |
| 6,165,350 A | 12/2000 | Lokhandwala et al. |
| 6,169,218 B1 | 1/2001 | Hearn |
| 6,171,052 B1 | 1/2001 | Aschenbruck et al. |
| 6,174,501 B1 | 1/2001 | Noureddini |
| 6,190,535 B1 | 2/2001 | Kalnes et al. |
| 6,203,585 B1 | 3/2001 | Majerczak |
| 6,235,104 B1 | 5/2001 | Chattopadhyay et al. |
| 6,258,987 B1 | 7/2001 | Schmidt et al. |
| 6,271,518 B1 | 8/2001 | Boehm et al. |
| 6,274,785 B1 | 8/2001 | Gore |
| 6,284,128 B1 | 9/2001 | Glover et al. |
| 6,296,812 B1 | 10/2001 | Gauthier et al. |
| 6,312,586 B1 | 11/2001 | Kalnes et al. |
| 6,315,815 B1 | 11/2001 | Spadaccini |
| 6,324,895 B1 | 12/2001 | Chitnis et al. |
| 6,328,348 B1 | 12/2001 | Cornford et al. |
| 6,331,436 B1 | 12/2001 | Richardson et al. |
| 6,348,074 B2 | 2/2002 | Wenzel |
| 6,350,371 B1 | 2/2002 | Lokhandwala et al. |
| 6,368,495 B1 | 4/2002 | Kocal et al. |
| 6,382,633 B1 | 5/2002 | Hashiguchi et al. |
| 6,390,673 B1 | 5/2002 | Camburn |
| 6,395,228 B1 | 5/2002 | Maggard et al. |
| 6,398,518 B1 | 6/2002 | Ingistov |
| 6,399,800 B1 | 6/2002 | Haas et al. |
| 6,420,181 B1 | 7/2002 | Novak |
| 6,422,035 B1 | 7/2002 | Phillippe |
| 6,435,279 B1 | 8/2002 | Howe et al. |
| 6,446,446 B1 | 9/2002 | Cowans |
| 6,446,729 B1 | 9/2002 | Bixenman et al. |
| 6,451,197 B1 | 9/2002 | Kalnes |
| 6,454,935 B1 | 9/2002 | Lesieur et al. |
| 6,467,303 B2 | 10/2002 | Ross |
| 6,482,762 B2 | 11/2002 | Ruffin et al. |
| 6,503,460 B1 | 1/2003 | Miller et al. |
| 6,528,047 B2 | 3/2003 | Arif et al. |
| 6,540,797 B1 | 4/2003 | Scott et al. |
| 6,558,531 B2 | 5/2003 | Steffens et al. |
| 6,589,323 B1 | 7/2003 | Korin |
| 6,609,888 B1 | 8/2003 | Ingistov |
| 6,622,490 B2 | 9/2003 | Ingistov |
| 6,644,935 B2 | 11/2003 | Ingistov |
| 6,660,895 B1 | 12/2003 | Brunet et al. |
| 6,672,858 B1 | 1/2004 | Benson et al. |
| 6,733,232 B2 | 5/2004 | Ingistov et al. |
| 6,733,237 B2 | 5/2004 | Ingistov |
| 6,736,961 B2 | 5/2004 | Plummer et al. |
| 6,740,226 B2 | 5/2004 | Mehra et al. |
| 6,772,581 B2 | 8/2004 | Ojiro et al. |
| 6,772,741 B1 | 8/2004 | Pittel et al. |
| 6,814,941 B1 | 11/2004 | Naunheimer et al. |
| 6,824,673 B1 | 11/2004 | Ellis et al. |
| 6,827,841 B2 | 12/2004 | Kiser et al. |
| 6,835,223 B2 | 12/2004 | Walker et al. |
| 6,841,133 B2 | 1/2005 | Niewiedzial et al. |
| 6,842,702 B2 | 1/2005 | Haaland et al. |
| 6,854,346 B2 | 2/2005 | Nimberger |
| 6,858,128 B1 | 2/2005 | Hoehn et al. |
| 6,866,771 B2 | 3/2005 | Lomas et al. |
| 6,869,521 B2 | 3/2005 | Lomas |
| 6,897,071 B2 | 5/2005 | Sonbul |
| 6,962,484 B2 | 11/2005 | Brandl et al. |
| 7,013,718 B2 | 3/2006 | Ingistov et al. |
| 7,035,767 B2 | 4/2006 | Archer et al. |
| 7,048,254 B2 | 5/2006 | Laurent et al. |
| 7,074,321 B1 | 7/2006 | Kalnes |
| 7,078,005 B2 | 7/2006 | Smith et al. |
| 7,087,153 B1 | 8/2006 | Kalnes |
| 7,156,123 B2 | 1/2007 | Welker et al. |
| 7,172,686 B1 | 2/2007 | Ji et al. |
| 7,174,715 B2 | 2/2007 | Armitage et al. |
| 7,194,369 B2 | 3/2007 | Lundstedt et al. |
| 7,213,413 B2 | 5/2007 | Battiste et al. |
| 7,225,840 B1 | 6/2007 | Craig et al. |
| 7,228,250 B2 | 6/2007 | Naiman et al. |
| 7,244,350 B2 | 7/2007 | Kar et al. |
| 7,252,755 B2 | 8/2007 | Kiser et al. |
| 7,255,531 B2 | 8/2007 | Ingistov |
| 7,260,499 B2 | 8/2007 | Watzke et al. |
| 7,291,257 B2 | 11/2007 | Ackerson et al. |
| 7,332,132 B2 | 2/2008 | Hedrick et al. |
| 7,404,411 B2 | 7/2008 | Welch et al. |
| 7,419,583 B2 | 9/2008 | Nieskens et al. |
| 7,445,936 B2 | 11/2008 | O'Connor et al. |
| 7,459,081 B2 | 12/2008 | Koenig |
| 7,485,801 B1 | 2/2009 | Pulter et al. |
| 7,487,955 B1 | 2/2009 | Buercklin |
| 7,501,285 B1 | 3/2009 | Triche et al. |
| 7,551,420 B2 | 6/2009 | Cerqueira et al. |
| 7,571,765 B2 | 8/2009 | Themig |
| 7,637,970 B1 | 12/2009 | Fox et al. |
| 7,669,653 B2 | 3/2010 | Craster et al. |
| 7,682,501 B2 | 3/2010 | Soni et al. |
| 7,686,280 B2 | 3/2010 | Lowery |
| 7,857,964 B2 | 12/2010 | Mashiko et al. |
| 7,866,346 B1 | 1/2011 | Walters |
| 7,895,011 B2 | 2/2011 | Youssefi et al. |
| 7,914,601 B2 | 3/2011 | Farr et al. |
| 7,931,803 B2 | 4/2011 | Buchanan |
| 7,932,424 B2 | 4/2011 | Fujimoto et al. |
| 7,939,335 B1 | 5/2011 | Triche et al. |
| 7,981,361 B2 | 7/2011 | Bacik |
| 7,988,753 B1 | 8/2011 | Fox et al. |
| 7,993,514 B2 | 8/2011 | Schlueter |
| 8,007,662 B2 | 8/2011 | Lomas et al. |
| 8,017,910 B2 | 9/2011 | Sharpe |
| 8,029,662 B2 | 10/2011 | Varma et al. |
| 8,037,938 B2 | 10/2011 | Jardim De Azevedo et al. |
| 8,038,774 B2 | 10/2011 | Peng |
| 8,064,052 B2 | 11/2011 | Feitisch et al. |
| 8,066,867 B2 | 11/2011 | Dziabala |
| 8,080,426 B1 | 12/2011 | Moore et al. |
| 8,127,845 B2 | 3/2012 | Assal |
| 8,193,401 B2 | 6/2012 | McGehee et al. |
| 8,236,566 B2 | 8/2012 | Carpenter et al. |
| 8,286,673 B1 | 10/2012 | Recker et al. |
| 8,354,065 B1 | 1/2013 | Sexton |
| 8,360,118 B2 | 1/2013 | Fleischer et al. |
| 8,370,082 B2 | 2/2013 | De Peinder et al. |
| 8,388,830 B2 | 3/2013 | Sohn et al. |
| 8,389,285 B2 | 3/2013 | Carpenter et al. |
| 8,397,803 B2 | 3/2013 | Crabb et al. |
| 8,397,820 B2 | 3/2013 | Fehr et al. |
| 8,404,103 B2 | 3/2013 | Dziabala |
| 8,434,800 B1 | 5/2013 | LeBlanc |
| 8,481,942 B2 | 7/2013 | Mertens |
| 8,506,656 B1 | 8/2013 | Turocy |
| 8,518,131 B2 | 8/2013 | Mattingly et al. |
| 8,524,180 B2 | 9/2013 | Canari et al. |
| 8,569,068 B2 | 10/2013 | Carpenter et al. |
| 8,579,139 B1 | 11/2013 | Sablak |
| 8,591,814 B2 | 11/2013 | Hodges |
| 8,609,048 B1 | 12/2013 | Beadle |

(56) References Cited

U.S. PATENT DOCUMENTS

| | | |
|---|---|---|
| 8,647,415 B1 | 2/2014 | De Haan et al. |
| 8,670,945 B2 | 3/2014 | van Schie |
| 8,685,232 B2 | 4/2014 | Mandal et al. |
| 8,735,820 B2 | 5/2014 | Mertens |
| 8,753,502 B1 | 6/2014 | Sexton et al. |
| 8,764,970 B1 | 7/2014 | Moore et al. |
| 8,778,823 B1 | 7/2014 | Oyekan et al. |
| 8,781,757 B2 | 7/2014 | Farquharson et al. |
| 8,784,645 B2 | 7/2014 | Iguchi et al. |
| 8,829,258 B2 | 9/2014 | Gong et al. |
| 8,916,041 B2 | 12/2014 | Van Den Berg et al. |
| 8,932,458 B1 | 1/2015 | Gianzon et al. |
| 8,986,402 B2 | 3/2015 | Kelly |
| 8,987,537 B1 | 3/2015 | Droubi et al. |
| 8,999,011 B2 | 4/2015 | Stern et al. |
| 8,999,012 B2 | 4/2015 | Kelly et al. |
| 9,011,674 B2 * | 4/2015 | Milam .................. C10G 45/04 208/112 |
| 9,057,035 B1 | 6/2015 | Kraus et al. |
| 9,097,423 B2 | 8/2015 | Kraus et al. |
| 9,109,176 B2 | 8/2015 | Stern et al. |
| 9,109,177 B2 | 8/2015 | Freel et al. |
| 9,138,738 B1 | 9/2015 | Glover et al. |
| 9,216,376 B2 | 12/2015 | Liu et al. |
| 9,272,241 B2 | 3/2016 | Königsson |
| 9,273,867 B2 | 3/2016 | Buzinski et al. |
| 9,279,748 B1 | 3/2016 | Hughes et al. |
| 9,289,715 B2 | 3/2016 | Høy-Petersen et al. |
| 9,315,403 B1 | 4/2016 | Laur et al. |
| 9,371,493 B1 | 6/2016 | Oyekan |
| 9,371,494 B2 | 6/2016 | Oyekan et al. |
| 9,377,340 B2 | 6/2016 | Hägg |
| 9,393,520 B2 | 7/2016 | Gomez |
| 9,410,102 B2 | 8/2016 | Eaton et al. |
| 9,428,695 B2 | 8/2016 | Narayanaswamy et al. |
| 9,453,169 B2 | 9/2016 | Stippich, Jr. et al. |
| 9,458,396 B2 | 10/2016 | Weiss et al. |
| 9,487,718 B2 | 11/2016 | Kraus et al. |
| 9,499,758 B2 | 11/2016 | Droubi et al. |
| 9,500,300 B2 | 11/2016 | Daigle |
| 9,506,649 B2 | 11/2016 | Rennie et al. |
| 9,580,662 B1 | 2/2017 | Moore |
| 9,624,448 B2 | 4/2017 | Joo et al. |
| 9,650,580 B2 | 5/2017 | Merdrignac et al. |
| 9,657,241 B2 | 5/2017 | Craig et al. |
| 9,662,597 B1 | 5/2017 | Formoso |
| 9,663,729 B2 | 5/2017 | Baird et al. |
| 9,665,693 B2 | 5/2017 | Saeger et al. |
| 9,709,545 B2 | 7/2017 | Mertens |
| 9,757,686 B2 | 9/2017 | Peng |
| 9,789,290 B2 | 10/2017 | Forsell |
| 9,803,152 B2 | 10/2017 | Kar et al. |
| 9,834,731 B2 | 12/2017 | Weiss et al. |
| 9,840,674 B2 | 12/2017 | Weiss et al. |
| 9,873,080 B2 | 1/2018 | Richardson |
| 9,878,300 B2 | 1/2018 | Norling |
| 9,890,907 B1 | 2/2018 | Highfield et al. |
| 9,891,198 B2 | 2/2018 | Sutan |
| 9,895,649 B2 | 2/2018 | Brown et al. |
| 9,896,630 B2 | 2/2018 | Weiss et al. |
| 9,914,094 B2 | 3/2018 | Jenkins et al. |
| 9,920,270 B2 | 3/2018 | Robinson et al. |
| 9,925,486 B1 | 3/2018 | Botti |
| 9,982,788 B1 | 5/2018 | Maron |
| 9,988,585 B2 | 6/2018 | Hayasaka et al. |
| 10,047,299 B2 | 8/2018 | Rubin-Pitel et al. |
| 10,087,397 B2 | 10/2018 | Phillips et al. |
| 10,099,175 B2 | 10/2018 | Takashashi et al. |
| 10,150,078 B2 | 12/2018 | Komatsu et al. |
| 10,228,708 B2 | 3/2019 | Lambert et al. |
| 10,239,034 B1 | 3/2019 | Sexton |
| 10,253,269 B2 | 4/2019 | Cantley et al. |
| 10,266,779 B2 | 4/2019 | Weiss et al. |
| 10,295,521 B2 | 5/2019 | Mertens |
| 10,308,884 B2 | 6/2019 | Klussman |
| 10,316,263 B2 | 6/2019 | Rubin-Pitel et al. |
| 10,384,157 B2 | 8/2019 | Balcik |
| 10,435,339 B2 | 10/2019 | Larsen et al. |
| 10,435,636 B2 | 10/2019 | Johnson et al. |
| 10,443,000 B2 | 10/2019 | Lomas |
| 10,443,006 B1 | 10/2019 | Fruchey et al. |
| 10,457,881 B2 | 10/2019 | Droubi et al. |
| 10,479,943 B1 | 11/2019 | Liu et al. |
| 10,494,579 B2 | 12/2019 | Wrigley et al. |
| 10,495,570 B2 | 12/2019 | Owen et al. |
| 10,501,699 B2 | 12/2019 | Robinson et al. |
| 10,526,547 B2 | 1/2020 | Larsen et al. |
| 10,533,141 B2 | 1/2020 | Moore et al. |
| 10,563,130 B2 | 2/2020 | Narayanaswamy et al. |
| 10,563,132 B2 | 2/2020 | Moore et al. |
| 10,563,133 B2 | 2/2020 | Moore et al. |
| 10,570,078 B2 | 2/2020 | Larsen et al. |
| 10,577,551 B2 | 3/2020 | Kraus et al. |
| 10,584,287 B2 | 3/2020 | Klussman et al. |
| 10,604,709 B2 | 3/2020 | Moore et al. |
| 10,640,719 B2 | 5/2020 | Freel et al. |
| 10,655,074 B2 | 5/2020 | Moore et al. |
| 10,696,906 B2 | 6/2020 | Cantley et al. |
| 10,808,184 B1 | 10/2020 | Moore |
| 10,836,966 B2 | 11/2020 | Moore et al. |
| 10,876,053 B2 | 12/2020 | Klussman et al. |
| 10,954,456 B2 | 3/2021 | Moore et al. |
| 10,961,468 B2 | 3/2021 | Moore et al. |
| 10,962,259 B2 | 3/2021 | Shah et al. |
| 10,968,403 B2 | 4/2021 | Moore |
| 11,021,662 B2 | 6/2021 | Moore et al. |
| 11,098,255 B2 | 8/2021 | Larsen et al. |
| 11,124,714 B2 | 9/2021 | Eller et al. |
| 11,136,513 B2 | 10/2021 | Moore et al. |
| 11,164,406 B2 | 11/2021 | Meroux et al. |
| 11,168,270 B1 | 11/2021 | Moore |
| 11,175,039 B2 | 11/2021 | Lochschmied et al. |
| 11,203,719 B2 | 12/2021 | Cantley et al. |
| 11,203,722 B2 | 12/2021 | Moore et al. |
| 11,214,741 B2 | 1/2022 | Davdov et al. |
| 11,306,253 B2 | 4/2022 | Timken et al. |
| 11,319,262 B2 | 5/2022 | Wu et al. |
| 11,352,577 B2 | 6/2022 | Woodchick et al. |
| 11,352,578 B2 | 6/2022 | Eller et al. |
| 11,384,301 B2 | 7/2022 | Eller et al. |
| 11,421,162 B2 | 8/2022 | Pradeep et al. |
| 11,460,478 B2 | 10/2022 | Sugiyama et al. |
| 11,467,172 B1 | 10/2022 | Mitzel et al. |
| 11,542,441 B2 | 1/2023 | Larsen et al. |
| 11,578,638 B2 | 2/2023 | Thobe |
| 11,634,647 B2 | 4/2023 | Cantley et al. |
| 11,667,858 B2 | 6/2023 | Eller et al. |
| 11,692,141 B2 | 7/2023 | Larsen et al. |
| 11,702,600 B2 | 7/2023 | Sexton et al. |
| 11,715,950 B2 | 8/2023 | Miller et al. |
| 11,720,526 B2 | 8/2023 | Miller et al. |
| 11,802,257 B2 | 10/2023 | Short et al. |
| 11,835,450 B2 | 12/2023 | Bledsoe, Jr. et al. |
| 11,860,069 B2 | 1/2024 | Bledsoe, Jr. |
| 11,891,581 B2 | 2/2024 | Cantley et al. |
| 11,898,109 B2 | 2/2024 | Sexton et al. |
| 11,905,468 B2 | 2/2024 | Sexton et al. |
| 11,905,479 B2 | 2/2024 | Eller et al. |
| 11,906,423 B2 | 2/2024 | Bledsoe, Jr. |
| 11,920,096 B2 | 3/2024 | Woodchick et al. |
| 11,921,035 B2 | 3/2024 | Bledsoe, Jr. et al. |
| 11,970,664 B2 | 4/2024 | Larsen |
| 2002/0014068 A1 | 2/2002 | Mittricker et al. |
| 2002/0061633 A1 | 5/2002 | Marsh |
| 2002/0170431 A1 | 11/2002 | Chang et al. |
| 2003/0041518 A1 | 3/2003 | Wallace et al. |
| 2003/0113598 A1 | 6/2003 | Chow et al. |
| 2003/0188536 A1 | 10/2003 | Mittricker |
| 2003/0194322 A1 | 10/2003 | Brandl et al. |
| 2004/0010170 A1 | 1/2004 | Vickers |
| 2004/0033617 A1 | 2/2004 | Sonbul |
| 2004/0040201 A1 | 3/2004 | Roos et al. |
| 2004/0079431 A1 | 4/2004 | Kissell |
| 2004/0121472 A1 | 6/2004 | Nemana et al. |

(56) References Cited

U.S. PATENT DOCUMENTS

| | | |
|---|---|---|
| 2004/0129605 A1 | 7/2004 | Goldstein et al. |
| 2004/0139858 A1 | 7/2004 | Entezarian |
| 2004/0154610 A1 | 8/2004 | Hopp et al. |
| 2004/0232050 A1 | 11/2004 | Martin et al. |
| 2004/0251170 A1 | 12/2004 | Chiyoda et al. |
| 2005/0042151 A1 | 2/2005 | Alward et al. |
| 2005/0088653 A1 | 4/2005 | Coates et al. |
| 2005/0123466 A1 | 6/2005 | Sullivan |
| 2005/0139516 A1 | 6/2005 | Nieskens et al. |
| 2005/0143609 A1 | 6/2005 | Wolf et al. |
| 2005/0150820 A1 | 7/2005 | Guo |
| 2005/0229777 A1 | 10/2005 | Brown |
| 2006/0037237 A1 | 2/2006 | Copeland et al. |
| 2006/0042701 A1 | 3/2006 | Jansen |
| 2006/0049082 A1 | 3/2006 | Niccum et al. |
| 2006/0091059 A1 | 5/2006 | Barbaro |
| 2006/0162243 A1 | 7/2006 | Wolf |
| 2006/0169305 A1 | 8/2006 | Jansen et al. |
| 2006/0210456 A1 | 9/2006 | Bruggendick |
| 2006/0169064 A1 | 10/2006 | Anschutz et al. |
| 2006/0220383 A1 | 10/2006 | Erickson |
| 2007/0003450 A1 | 1/2007 | Burdett et al. |
| 2007/0082407 A1 | 4/2007 | Little |
| 2007/0112258 A1 | 5/2007 | Soyemi et al. |
| 2007/0202027 A1 | 8/2007 | Walker et al. |
| 2007/0212271 A1 | 9/2007 | Kennedy et al. |
| 2007/0212790 A1 | 9/2007 | Welch et al. |
| 2007/0215521 A1 | 9/2007 | Havlik et al. |
| 2007/0243556 A1 | 10/2007 | Wachs |
| 2007/0283812 A1 | 12/2007 | Liu et al. |
| 2008/0078693 A1 | 4/2008 | Sexton et al. |
| 2008/0078694 A1 | 4/2008 | Sexton et al. |
| 2008/0078695 A1 | 4/2008 | Sexton et al. |
| 2008/0081844 A1 | 4/2008 | Shires et al. |
| 2008/0087592 A1 | 4/2008 | Buchanan |
| 2008/0092436 A1 | 4/2008 | Seames et al. |
| 2008/0109107 A1 | 5/2008 | Stefani et al. |
| 2008/0149486 A1 | 6/2008 | Greaney et al. |
| 2008/0156696 A1 | 7/2008 | Niccum et al. |
| 2008/0207974 A1 | 8/2008 | McCoy et al. |
| 2008/0211505 A1 | 9/2008 | Trygstad et al. |
| 2008/0247942 A1 | 10/2008 | Kandziora et al. |
| 2008/0253936 A1 | 10/2008 | Abhari |
| 2009/0151250 A1 | 6/2009 | Agrawal |
| 2009/0152454 A1 | 6/2009 | Nelson et al. |
| 2009/0158824 A1 | 6/2009 | Brown et al. |
| 2010/0127217 A1 | 5/2010 | Lightowlers et al. |
| 2010/0131247 A1 | 5/2010 | Carpenter et al. |
| 2010/0166602 A1 | 7/2010 | Bacik |
| 2010/0243235 A1 | 9/2010 | Caldwell et al. |
| 2010/0301044 A1 | 12/2010 | Sprecher |
| 2010/0318118 A1 | 12/2010 | Forsell |
| 2011/0147267 A1 | 6/2011 | Kaul et al. |
| 2011/0155646 A1 | 6/2011 | Karas et al. |
| 2011/0175032 A1 | 7/2011 | Günther |
| 2011/0186307 A1 | 8/2011 | Derby |
| 2011/0237856 A1 | 9/2011 | Mak |
| 2011/0247835 A1 | 10/2011 | Crabb |
| 2011/0277377 A1 | 11/2011 | Novak et al. |
| 2011/0299076 A1 | 12/2011 | Feitisch et al. |
| 2011/0319698 A1 | 12/2011 | Sohn et al. |
| 2012/0012342 A1 | 1/2012 | Wilkin et al. |
| 2012/0125813 A1 | 5/2012 | Bridges et al. |
| 2012/0125814 A1 | 5/2012 | Sanchez et al. |
| 2012/0131853 A1 | 5/2012 | Thacker et al. |
| 2012/0222550 A1 | 9/2012 | Ellis |
| 2012/0272715 A1 | 11/2012 | Kriel et al. |
| 2013/0014431 A1 | 1/2013 | Jin et al. |
| 2013/0109895 A1 | 5/2013 | Novak et al. |
| 2013/0112313 A1 | 5/2013 | Donnelly et al. |
| 2013/0125619 A1 | 5/2013 | Wang |
| 2013/0186739 A1 | 7/2013 | Trompiz |
| 2013/0192339 A1 | 8/2013 | Kriel et al. |
| 2013/0225897 A1 | 8/2013 | Candelon et al. |
| 2013/0288355 A1 | 10/2013 | DeWitte et al. |
| 2013/0334027 A1 | 12/2013 | Winter et al. |
| 2013/0342203 A1 | 12/2013 | Trygstad et al. |
| 2014/0019052 A1 | 1/2014 | Zaeper et al. |
| 2014/0024873 A1 | 1/2014 | De Haan et al. |
| 2014/0041150 A1 | 2/2014 | Sjoberg |
| 2014/0121428 A1 | 5/2014 | Wang et al. |
| 2014/0229010 A1 | 8/2014 | Farquharson et al. |
| 2014/0296057 A1 | 10/2014 | Ho et al. |
| 2014/0299515 A1 | 10/2014 | Weiss et al. |
| 2014/0311953 A1 | 10/2014 | Chimenti et al. |
| 2014/0316176 A1 | 10/2014 | Fjare et al. |
| 2014/0332444 A1 | 11/2014 | Weiss et al. |
| 2014/0353138 A1 | 12/2014 | Amale et al. |
| 2014/0374322 A1 | 12/2014 | Venkatesh |
| 2015/0005547 A1 | 1/2015 | Freel et al. |
| 2015/0005548 A1 | 1/2015 | Freel et al. |
| 2015/0034570 A1 | 2/2015 | Andreussi |
| 2015/0034599 A1 | 2/2015 | Hunger et al. |
| 2015/0057477 A1 | 2/2015 | Ellig et al. |
| 2015/0071028 A1 | 3/2015 | Glanville |
| 2015/0122704 A1 | 5/2015 | Kumar et al. |
| 2015/0166426 A1 | 6/2015 | Wegerer et al. |
| 2015/0240167 A1 | 8/2015 | Kulprathipanja et al. |
| 2015/0240174 A1 | 8/2015 | Bru et al. |
| 2015/0337207 A1 | 11/2015 | Chen et al. |
| 2015/0337225 A1 | 11/2015 | Droubi et al. |
| 2015/0337226 A1 | 11/2015 | Tardif et al. |
| 2015/0353851 A1 | 12/2015 | Buchanan |
| 2016/0045918 A1 | 2/2016 | Lapham |
| 2016/0090539 A1 | 3/2016 | Frey et al. |
| 2016/0122662 A1 | 5/2016 | Weiss et al. |
| 2016/0122666 A1 | 5/2016 | Weiss et al. |
| 2016/0160139 A1 | 6/2016 | Dawe et al. |
| 2016/0168481 A1 | 6/2016 | Ray et al. |
| 2016/0175749 A1 | 6/2016 | Suda |
| 2016/0244677 A1 | 8/2016 | Froehle |
| 2016/0298851 A1 | 10/2016 | Brickwood et al. |
| 2016/0312127 A1 | 10/2016 | Frey et al. |
| 2016/0312130 A1 | 10/2016 | Majcher et al. |
| 2017/0009163 A1 | 1/2017 | Kraus et al. |
| 2017/0115190 A1 | 4/2017 | Hall et al. |
| 2017/0131728 A1 | 5/2017 | Lambert et al. |
| 2017/0151526 A1 | 6/2017 | Cole |
| 2017/0183575 A1 | 6/2017 | Rubin-Pitel et al. |
| 2017/0198910 A1 | 7/2017 | Garg |
| 2017/0226434 A1 | 8/2017 | Zimmerman |
| 2017/0233670 A1 | 8/2017 | Feustel et al. |
| 2017/0269559 A1* | 9/2017 | Trygstad .............. G01V 11/00 |
| 2018/0017469 A1 | 1/2018 | English et al. |
| 2018/0037308 A1 | 2/2018 | Lee et al. |
| 2018/0080958 A1 | 3/2018 | Marchese et al. |
| 2018/0119039 A1 | 5/2018 | Tanaka et al. |
| 2018/0134974 A1 | 5/2018 | Weiss et al. |
| 2018/0163144 A1 | 6/2018 | Weiss et al. |
| 2018/0179457 A1 | 6/2018 | Mukherjee et al. |
| 2018/0202607 A1 | 7/2018 | McBride |
| 2018/0230389 A1 | 8/2018 | Moore et al. |
| 2018/0246142 A1 | 8/2018 | Glover |
| 2018/0355263 A1 | 12/2018 | Moore et al. |
| 2018/0361312 A1 | 12/2018 | Dutra e Mello et al. |
| 2018/0371325 A1 | 12/2018 | Streiff et al. |
| 2019/0002772 A1 | 1/2019 | Moore et al. |
| 2019/0010405 A1 | 1/2019 | Moore et al. |
| 2019/0010408 A1 | 1/2019 | Moore et al. |
| 2019/0016980 A1 | 1/2019 | Kar et al. |
| 2019/0093026 A1 | 3/2019 | Wohaibi et al. |
| 2019/0099706 A1 | 4/2019 | Sampath |
| 2019/0100702 A1 | 4/2019 | Cantley et al. |
| 2019/0127651 A1 | 5/2019 | Kar et al. |
| 2019/0128160 A1 | 5/2019 | Peng |
| 2019/0136144 A1 | 5/2019 | Wohaibi et al. |
| 2019/0153340 A1 | 5/2019 | Weiss et al. |
| 2019/0153942 A1 | 5/2019 | Wohaibi et al. |
| 2019/0169509 A1 | 6/2019 | Cantley et al. |
| 2019/0185772 A1 | 6/2019 | Berkhous et al. |
| 2019/0201841 A1 | 7/2019 | McClelland |
| 2019/0203130 A1 | 7/2019 | Mukherjee |
| 2019/0218466 A1 | 7/2019 | Slade et al. |
| 2019/0233741 A1 | 8/2019 | Moore et al. |

(56) References Cited

U.S. PATENT DOCUMENTS

| | | |
|---|---|---|
| 2019/0292465 A1 | 9/2019 | McBride |
| 2019/0338205 A1 | 11/2019 | Ackerson et al. |
| 2019/0382668 A1 | 12/2019 | Klussman et al. |
| 2019/0382672 A1 | 12/2019 | Sorensen |
| 2020/0041481 A1 | 2/2020 | Burgess |
| 2020/0049675 A1 | 2/2020 | Ramirez |
| 2020/0080881 A1 | 3/2020 | Langlois et al. |
| 2020/0095509 A1 | 3/2020 | Moore et al. |
| 2020/0123458 A1 | 4/2020 | Moore et al. |
| 2020/0181502 A1 | 6/2020 | Paasikallio et al. |
| 2020/0199462 A1 | 6/2020 | Klussman et al. |
| 2020/0208068 A1 | 7/2020 | Hossain et al. |
| 2020/0246743 A1 | 8/2020 | Sorensen |
| 2020/0291316 A1 | 9/2020 | Robbins et al. |
| 2020/0312470 A1 | 10/2020 | Craig et al. |
| 2020/0316513 A1 | 10/2020 | Zhao |
| 2020/0332198 A1 | 10/2020 | Yang et al. |
| 2020/0353456 A1 | 11/2020 | Zalewski et al. |
| 2020/0378600 A1 | 12/2020 | Craig et al. |
| 2020/0385644 A1 | 12/2020 | Rogel et al. |
| 2021/0002559 A1 | 1/2021 | Larsen et al. |
| 2021/0003502 A1 | 1/2021 | Kirchmann et al. |
| 2021/0033631 A1 | 2/2021 | Field et al. |
| 2021/0103304 A1 | 4/2021 | Fogarty et al. |
| 2021/0115344 A1 | 4/2021 | Perkins et al. |
| 2021/0181164 A1 | 6/2021 | Shirkhan et al. |
| 2021/0213382 A1 | 7/2021 | Cole |
| 2021/0238487 A1 | 8/2021 | Moore et al. |
| 2021/0253964 A1 | 8/2021 | Eller et al. |
| 2021/0253965 A1 | 8/2021 | Woodchick et al. |
| 2021/0261874 A1 | 8/2021 | Eller et al. |
| 2021/0284919 A1 | 9/2021 | Moore et al. |
| 2021/0292661 A1 | 9/2021 | Klussman et al. |
| 2021/0301210 A1 | 9/2021 | Timken et al. |
| 2021/0396660 A1 | 12/2021 | Zarrabian |
| 2021/0403819 A1 | 12/2021 | Moore et al. |
| 2022/0040629 A1 | 2/2022 | Edmoundson et al. |
| 2022/0041939 A1 | 2/2022 | Titta et al. |
| 2022/0041940 A1 | 2/2022 | Pradeep et al. |
| 2022/0048019 A1 | 2/2022 | Zalewski et al. |
| 2022/0268694 A1 | 8/2022 | Bledsoe et al. |
| 2022/0298440 A1 | 9/2022 | Woodchick et al. |
| 2022/0299170 A1 | 9/2022 | Raynor et al. |
| 2022/0343229 A1 | 10/2022 | Gruber et al. |
| 2022/0357303 A1 | 11/2022 | Zhu et al. |
| 2023/0015077 A1 | 1/2023 | Kim |
| 2023/0078852 A1 | 3/2023 | Campbell et al. |
| 2023/0080192 A1 | 3/2023 | Bledsoe et al. |
| 2023/0082189 A1 | 3/2023 | Bledsoe et al. |
| 2023/0084329 A1 | 3/2023 | Bledsoe et al. |
| 2023/0087063 A1 | 3/2023 | Mitzel et al. |
| 2023/0089935 A1 | 3/2023 | Bledsoe et al. |
| 2023/0093452 A1 | 3/2023 | Sexton et al. |
| 2023/0111609 A1 | 4/2023 | Sexton et al. |
| 2023/0113140 A1 | 4/2023 | Larsen et al. |
| 2023/0118319 A1 | 4/2023 | Sexton et al. |
| 2023/0220286 A1 | 7/2023 | Cantley et al. |
| 2023/0241548 A1 | 8/2023 | Holland et al. |
| 2023/0242837 A1 | 8/2023 | Short et al. |
| 2023/0259080 A1 | 8/2023 | Whikehart et al. |
| 2023/0259088 A1 | 8/2023 | Borup et al. |
| 2023/0272290 A1 | 8/2023 | Larsen et al. |
| 2023/0295528 A1 | 9/2023 | Eller et al. |
| 2023/0332056 A1 | 10/2023 | Larsen et al. |
| 2023/0332058 A1 | 10/2023 | Larsen et al. |
| 2023/0357649 A1 | 11/2023 | Sexton et al. |
| 2023/0400184 A1 | 12/2023 | Craig |
| 2023/0416615 A1 | 12/2023 | Larsen |
| 2023/0416638 A1 | 12/2023 | Short |
| 2024/0011898 A1 | 1/2024 | Bledsoe, Jr. et al. |
| 2024/0115996 A1 | 4/2024 | Rudd |
| 2024/0117262 A1 | 4/2024 | Eller |
| 2024/0118194 A1 | 4/2024 | Bledsoe, Jr. |
| 2024/0124790 A1 | 4/2024 | Sexton |
| 2024/0132786 A1 | 4/2024 | Sexton |

FOREIGN PATENT DOCUMENTS

| | | |
|---|---|---|
| CA | 2949201 | 11/2015 |
| CA | 2822742 | 12/2016 |
| CA | 3009808 | 7/2017 |
| CA | 2904903 | 8/2020 |
| CA | 3077045 | 9/2020 |
| CA | 2947431 | 3/2021 |
| CA | 3004712 | 6/2021 |
| CA | 2980055 | 12/2021 |
| CA | 2879783 | 1/2022 |
| CA | 2991614 | 1/2022 |
| CA | 2980069 | 11/2022 |
| CA | 3109606 | 12/2022 |
| CH | 432129 | 3/1967 |
| CN | 2128346 | 3/1993 |
| CN | 201264907 Y | 7/2009 |
| CN | 201306736 | 9/2009 |
| CN | 201940168 | 8/2011 |
| CN | 102120138 | 12/2012 |
| CN | 203453713 | 2/2014 |
| CN | 103627433 | 3/2014 |
| CN | 203629938 | 6/2014 |
| CN | 203816490 | 9/2014 |
| CN | 104353357 | 2/2015 |
| CN | 204170623 | 2/2015 |
| CN | 103331093 | 4/2015 |
| CN | 204253221 | 4/2015 |
| CN | 204265565 | 4/2015 |
| CN | 105148728 | 12/2015 |
| CN | 204824775 | 12/2015 |
| CN | 103933845 | 1/2016 |
| CN | 105289241 | 2/2016 |
| CN | 105536486 | 5/2016 |
| CN | 105804900 | 7/2016 |
| CN | 103573430 | 8/2016 |
| CN | 205655095 | 10/2016 |
| CN | 104326604 | 11/2016 |
| CN | 104358627 | 11/2016 |
| CN | 106237802 | 12/2016 |
| CN | 205779365 | 12/2016 |
| CN | 106407648 | 2/2017 |
| CN | 105778987 | 8/2017 |
| CN | 207179722 | 4/2018 |
| CN | 207395575 | 5/2018 |
| CN | 108179022 | 6/2018 |
| CN | 108704478 | 10/2018 |
| CN | 109126458 | 1/2019 |
| CN | 109423345 | 3/2019 |
| CN | 109499365 | 3/2019 |
| CN | 109705939 | 5/2019 |
| CN | 109722303 | 5/2019 |
| CN | 110129103 | 8/2019 |
| CN | 110229686 | 9/2019 |
| CN | 209451617 | 10/2019 |
| CN | 110987862 | 4/2020 |
| CN | 111336612 A | 6/2020 |
| CN | 213824075 U | 7/2021 |
| CN | 215263512 U | 12/2021 |
| CN | 215288592 | 12/2021 |
| CN | 113963818 | 1/2022 |
| CN | 114001278 | 2/2022 |
| CN | 217431673 | 9/2022 |
| CN | 218565442 | 3/2023 |
| DE | 10179 | 6/1912 |
| DE | 3721725 | 1/1989 |
| DE | 19619722 | 11/1997 |
| DE | 102010017563 | 12/2011 |
| DE | 102014009231 A1 | 1/2016 |
| EP | 0142352 | 5/1985 |
| EP | 0527000 | 2/1993 |
| EP | 0783910 A1 | 7/1997 |
| EP | 0949318 | 10/1999 |
| EP | 0783910 B1 | 12/2000 |
| EP | 0801299 | 3/2004 |
| EP | 1413712 | 4/2004 |
| EP | 1600491 | 11/2005 |
| EP | 1870153 | 12/2007 |
| EP | 2047905 | 4/2009 |

(56) References Cited

FOREIGN PATENT DOCUMENTS

| | | |
|---|---|---|
| EP | 2903955 | 8/2015 |
| EP | 2955345 | 12/2015 |
| EP | 3130773 | 2/2017 |
| EP | 3139009 | 3/2017 |
| EP | 3239483 | 11/2017 |
| EP | 3085910 | 8/2018 |
| EP | 3355056 | 8/2018 |
| EP | 2998529 | 2/2019 |
| EP | 3441442 | 2/2019 |
| EP | 3569988 | 11/2019 |
| EP | 3878926 | 9/2021 |
| FR | 2357630 | 2/1978 |
| FR | 3004722 | 3/2016 |
| FR | 3027909 | 5/2016 |
| FR | 3067036 | 12/2018 |
| FR | 3067037 | 12/2018 |
| FR | 3072684 | 4/2019 |
| FR | 3075808 | 6/2019 |
| GB | 775273 | 5/1957 |
| GB | 933618 | 8/1963 |
| GB | 1207719 | 10/1970 |
| GB | 2144526 | 3/1985 |
| IN | 202111016535 | 7/2021 |
| JP | 59220609 | 12/1984 |
| JP | 2003129067 | 5/2003 |
| JP | 3160405 | 6/2010 |
| JP | 2015059220 | 3/2015 |
| JP | 2019014275 | 1/2019 |
| KR | 101751923 | 7/2017 |
| KR | 101823897 | 3/2018 |
| KR | 20180095303 | 8/2018 |
| KR | 20190004474 | 1/2019 |
| KR | 20190004475 | 1/2019 |
| RU | 2673558 | 11/2018 |
| RU | 2700705 | 9/2019 |
| RU | 2760879 | 12/2021 |
| TW | 320682 | 11/1997 |
| WO | 94/08225 | 4/1994 |
| WO | 199640436 | 12/1996 |
| WO | 1997033678 | 9/1997 |
| WO | 199803249 | 1/1998 |
| WO | 1999041591 | 8/1999 |
| WO | 2001051588 | 7/2001 |
| WO | 2002038295 | 5/2002 |
| WO | 2006126978 | 11/2006 |
| WO | 2008088294 | 7/2008 |
| WO | 2010/144191 | 12/2010 |
| WO | 2012026302 | 3/2012 |
| WO | 2012062924 | 5/2012 |
| WO | 2012089776 | 7/2012 |
| WO | 2012108584 | 8/2012 |
| WO | 2014053431 | 4/2014 |
| WO | 2014096703 | 6/2014 |
| WO | 2014096704 | 6/2014 |
| WO | 2014191004 | 7/2014 |
| WO | 2014177424 | 11/2014 |
| WO | 2014202815 | 12/2014 |
| WO | 2016167708 | 10/2016 |
| WO | 2017067088 | 4/2017 |
| WO | 2017207976 | 12/2017 |
| WO | 2018017664 | 1/2018 |
| WO | 2018073018 | 4/2018 |
| WO | 2018122274 | 7/2018 |
| WO | 2018148675 | 8/2018 |
| WO | 2018148681 | 8/2018 |
| WO | 2018231105 | 12/2018 |
| WO | 2019053323 | 3/2019 |
| WO | 2019104243 | 5/2019 |
| WO | 2019155183 | 8/2019 |
| WO | 2019178701 | 9/2019 |
| WO | 2020035797 | 2/2020 |
| WO | 2020160004 | 8/2020 |
| WO | 2021058289 | 4/2021 |
| WO | 2022133359 | 6/2022 |
| WO | 2022144495 | 7/2022 |
| WO | 2022149501 | 7/2022 |
| WO | 2022219234 | 10/2022 |
| WO | 2022220991 | 10/2022 |
| WO | 2023038579 | 3/2023 |
| WO | 2023137304 | 7/2023 |
| WO | 2023164683 | 8/2023 |
| WO | 2023242308 | 12/2023 |

OTHER PUBLICATIONS

Bollas et al., "Modeling Small-Diameter FCC Riser Reactors. A Hydrodynamic and Kinetic Approach", Industrial and Engineering Chemistry Research, 41(22), 5410-5419, 2002.

Voutetakis et al., "Computer Application and Software Development for the Automation of a Fluid Catalytic Cracking Pilot Plant—Experimental Results", Computers & Chemical Engineering, vol. 20 Suppl., S1601-S1606, 1996.

Platvoet et al., Process Burners 101, American Institute of Chemical Engineers, Aug. 2013.

Luyben, W. L., Process Modeling, Simulation, and Control for Chemical Engineers, Feedforward Control, pp. 431-433.

Cooper et al., Calibration transfer of near-IR partial least squares property models of fuels using standards, Wiley Online Library, Jul. 19, 2011.

ABB Measurement & Analytics, Using FT-NIR as a Multi-Stream Method for CDU Optimization, Nov. 8, 2018.

Modcon Systems LTD., On-Line NIR Analysis of Crude Distillation Unit, Jun. 2008.

ABB Measurement & Analytics, Crude distillation unit (CDU) optimization, 2017.

Guided Wave Inc., The Role of NIR Process Analyzers in Refineries to Process Crude Oil into Useable Petrochemical Products, 2021.

ABB Measurement & Analytics, Optimizing Refinery Catalytic Reforming Units with the use of Simple Robust On-Line Analyzer Technology, Nov. 27, 2017, https://www.azom.com/article.aspx?ArticleID=14840.

Bueno, Alexis et al., Characterization of Catalytic Reforming Streams by NIR Spectroscopy, Energy & Fuels 2009, 23, 3172-3177, Apr. 29, 2009.

Caricato, Enrico et al., Catalytic Naphtha Reforming—a Novel Control System for the Bench-Scale Evaluation of Commerical Continuous Catalytic Regeneration Catalysts, Industrial of Engineering Chemistry Research, ACS Publications, May 18, 2017.

Alves, J. C. L., et al., Diesel Oil Quality Parameter Determinations Using Support Vector Regression and Near Infrared Spectroscopy for Hydrotreationg Feedstock Monitoring, Journal of Near Infrared Spectroscopy, 20, 419-425 (2012), Jul. 23, 2012.

Rodriguez, Elena et al., Coke deposition and product distribution in the co-cracking of waste polyolefin derived streams and vacuum gas oil under FCC unit conditions, Fuel Processing Technology 192 (2019), 130-139.

Passamonti, Francisco J. et al., Recycling of waste plastics into fuels, PDPE conversion in FCC, Applied Catalysis B: Environmental 125 (2012), 499-506.

De Rezende Pinho, Andrea et al., Fast pyrolysis oil from pinewood chips co-processing with vacuum gas oil in an FCC unit for second generation fuel production, Fuel 188 (2017), 462-473.

Niaei et al., Computational Study of Pyrolysis Reactions and Coke Deposition in Industrial Naphtha Cracking, P.M.A. Sloot et al., Eds.: ICCS 2002, LNCS 2329, pp. 723-732, 2002.

Hanson et al., An atmospheric crude tower revamp, Digital Refining, Article, Jul. 2005.

Lopiccolo, Philip, Coke trap reduces FCC slurry exchanger fouling for Texas refiner, Oil & Gas Journal, Sep. 8, 2003.

Martino, Germain, Catalytic Reforming, Petroleum Refining Conversion Processes, vol. 3, Chapter 4, pp. 101-168, 2001.

Baukal et al., Natural-Draft Burners, Industrial Burners Handbook, CRC Press 2003.

Spekuljak et al., Fluid Distributors for Structured Packing Colums, AICHE, Nov. 1998.

Hemler et al., UOP Fluid Catalytic Cracking Process, Handbook of Petroleum Refining Processes, 3rd ed., McGraw Hill, 2004.

(56) References Cited

OTHER PUBLICATIONS

United States Department of Agriculture, NIR helps Turn Vegetable Oil into High-Quality Biofuel, Agricultural Research Service, Jun. 15, 1999.
NPRA, 2006 Cat Cracker Seminar Transcript, National Petrochemical & Refiners Association, Aug. 1-2, 2006.
Niccum, Phillip K. et al. KBR, CatCracking.com, More Production—Less Risk!, Twenty Questions: Identify Probably Cuase of High FCC Catalyst Loss, May 3-6, 2011.
NPRA, Cat-10-105 Troubleshooting FCC Catalyst Losses, National Petrochemical & Refiners Association, Aug. 24-25, 2010.
Fraser, Stuart, Distillation in Refining, Distillation Operation and Applications (2014), pp. 155-190 (Year: 2014).
Yasin et al., Quality and chemistry of crude oils, Journal of Petroleum Technology and Alternative Fuels, vol. 4(3), pp. 53-63, Mar. 2013.
Penn State, Cut Points, https://www.e-education.psu.edu/fsc432/content/cut-points, 2018.
The American Petroleum Institute, Petroleum HPV Testing Group, Heavy Fuel Oils Category Analysis and Hazard Characterization, Dec. 7, 2012.
Increase Gasoline Octane and Light Olefin Yeilds with ZSM-5, vol. 5, Issue 5, http://www.refiningonline.com/engelhardkb/crep/TCR4_35.htm.
Fluid Catalytic Cracking and Light Olefins Production, Hydrocarbon Publishing Company, 2011, http://www.hydrocarbonpublishing.com/store10/product.php?productid+b21104.
Zhang et al., Multifunctional two-stage riser fluid catalytic cracking process, Springer Applied Petrocchemical Research, Sep. 3, 2014.
Reid, William, Recent trends in fluid catalytic cracking patents, part V: reactor section, Dilworth IP, Sep. 3, 2014.
Akah et al., Maximizing propylene production via FCC technology, SpringerLink, Mar. 22, 2015.
Vogt et al., Fluid Catalytic Cracking: Recent Developments on the Grand Old Lady of Zeolite Catalysis, Royal Society of Chemistry, Sep. 18, 2015.
Zhou et al., Study on the Integration of Flue Gas Waste He Desulfuization and Dust Removal in Civilian Coalfired Heating Furnance, 2020 IOP Conf. Ser.: Earth Environ. Sci. 603 012018.
Vivek et al., Assessment of crude oil blends, refiner's assessment of the compatibility of opportunity crudes in blends aims to avoid the processing problems introduced by lower-quality feedstocks, www.digitalrefining.com/article/10000381, 2011.
International Standard, ISO 8217, Petroleum products—Fuels (class F)—Specifications of marine fuels, Sixth Edition, 2017.
International Standard, ISO 10307-1, Petroleum products—Total sediment in residual fuel oils—, Part 1: Determination by hot filtration, Second Edition, 2009.
International Standard, ISO 10307-2, Petroleum products—Total sediment in residual fuel oils—, Part 2: Determination using standard procedures for aging, Second Edition, 2009.
Ebner et al., Deactivatin and durability of the catalyst for Hotspot™ natural gas processing, OSTI, 2000, https://www.osti/gov/etdeweb/servlets/purl/20064378, (Year: 2000).
Morozov et al., Best Practices When Operating a Unit for Removing Hydrogen Sulfide from Residual Fuel Oil, Chemistry and Technology of Fuels and Oils, vol. 57, No. 4, Sep. 2001.
Calbry-Muzyka et al., Deep removal of sulfur and trace organic compounds from biogas to protect a catalytic methananation reactor, Chemical Engineering Joural 360, pp. 577-590, 2019.
Cheah et al., Review of Mid- to High-Tempearture Sulfur Sorbents for Desulfurization of Biomass- and Coal-derived Syngas, Energy Fuels 2009, 23, pp. 5291-5307, Oct. 16, 2019.
Mandal et al., Simultaneous absorption of carbon dioxide of hydrogen sulfide into aqueous blends of 2-amino-2-methyl-1 propanol and diethanolamine, Chemical Engineering Science 60, pp. 6438-6451, 2005.
Meng et al., In bed and downstream hot gas desulphurization during solid fuel gasification: A review, Fuel Processing Technology 91, pp. 964-981, 2010.
Okonkwo et al., Role of Amine Structure on Hydrogen Sulfide Capture from Dilute Gas Streams Using Solid Adsorbents, Energy Fuels, 32, pp. 6926-6933, 2018.
Okonkwo et al., Selective removal of hydrogen sulfide from simulated biogas streams using sterically hindered amine adsorbents, Chemical Engineering Journal 379, pp. 122-349, 2020.
Lerh et al., Feature: IMO 2020 draws more participants into Singapore's bunkering pool., S&P Global Platts, www.spglobal.com, Sep. 3, 2019.
Cremer et al., Model Based Assessment of the Novel Use of Sour Water Stripper Vapor for NOx Control in CO Boilers, Industrial Combustion Symposium, American Flame Research Committee 2021, Nov. 19, 2021.
Frederick et al., Alternative Technology for Sour Water Stripping, University of Pennsylvania, Penn Libraries, Scholarly Commons, Apr. 20, 2018.
Da Vinci Laboratory Solutions B. V., DVLS Liquefied Gas Injector, Sampling and analysis of liquefied gases, https://www.davinci-ls.com/en/products/dvls-products/dvls-liquefied-gas-injector.
Wasson ECE Instrumentation, LPG Pressurization Station, https://wasson-ece.com/products/small-devices/lpg-pressurization-station.
Mechatest B. V., Gas & Liquefied Gas Sampling Systems, https://www.mechatest.com/products/gas-sampling-system/.
La Rivista dei Combustibili, The Fuel Magazine, vol. 66, File 2, 2012.
Zulkefi et al., Overview of H2S Removal Technologies from Biogas Production, International Journal of Applied Engineering Research ISSN 0973-4562, vol. 11, No. 20, pp. 10060-10066, © Research India Publications, 2016.
Seo et al., Methanol absorption characteristics for the removal of H2S (hydrogen sulfide), COS (carbonyl sulfide) and CO2 (carbon dioxide) in a pilot-scale biomass-to-liquid process, Energy 66, pp. 56-62, 2014.
Lloyd's Register, Using technology to trace the carbon intensity of sustainable marine fuels, Feb. 15, 2023.
Cooper et al., Calibration transfer of near-IR partial least squares property models of fuels using virtual standards, Wiley Online Library, Jul. 19, 2011.
"Optimizing Refinery Catalytic Reforming Units with the Use of Simple Robust On-Line Analyzer Technology", ABB Measurement & Analytics—Analytical Measurement Products, Nov. 27, 2017, found at: https://www.azom.com/article.aspx?ArticleID=14840.
Caricato, Enrico et al., "Catalytic Naphtha Reforming—a Novel Control System for the Bench-Scale Evaluation of Commercial Continuous Catalytic Regeneration Catalysts", Industrial & Engineering Chemistry Research, ACS Publications, May 18, 2017.
Alves, J.C.L. et al., "Dielsel Oil Quality Parameter Determinations Using Support Vector Regression and Near Infrared Spectroscopy for Hydrotreating Feedstock Monitoring", Journal of Near Infrared Spectroscopy, 20, 419-425 (2012), Jul. 23, 2012.
Pashikanti et al., "Predictive modeling of large-scale integrated refinery reaction and fractionation systems from plant data. Part 3: Continuous Catalyst Regeneration (CCR) Reforming Process," Energy & Fuels 2011, 25, 5320-5344 (Year: 2011).
Swagelok, Grab Sampling Systems Application Guide, 53 pages.
Frank et al., "Fuel Tank and Charcoal Canister Fire Hazards during EVAP System Leak Testing", SAE International, 2007 World Congress, Detroit, Michigan, Apr. 16-19, 2007, 11 pages.
Doolin et al., "Catalyst Regeneration and Continuous Reforming Issues", Catalytic Naptha Reforming, 2004.

* cited by examiner

| Group | SEC | R | No. of Factors | Outliers |
|---|---|---|---|---|
| Saturates | 1.81 | 0.928 | 9 | 575 |
| Mono-Aromatics | 1.36 | 0.816 | 6 | 402 |
| Di-Aromatics | 1.17 | 0.606 | 8 | 128, 402, 405, 487 |
| Tri/Plus-Aromatics | 1.43 | 0.897 | 12 | 489, 493 |
| Polars | 0.577 | 0.864 | 10 | 575, 493, 437 |
| Sulphur (0.1% to 0.5%)(115 samples) | 0.063 | 0.838 | 9 | 563, 535, 745 |
| Sulphur (0.51% to 2.5%)(110 samples) | 0.077 | 0.992 | 13 | None |
| Nitrogen (0.013% to 0.102%)(210 samples) | 0.0080 | 0.886 | 6 | None |

FIG. 6A

| | Saturates | Mono-Aromatics | Di-Aromatics | Tri/Plus Aromatics | Polars |
|---|---|---|---|---|---|
| Minimum | 48.46 | 10.22 | 4.80 | 5.11 | 0.32 |
| Maximum | 69.85 | 26.18 | 16.25 | 21.73 | 7.61 |

FIG. 6B

| Property | PLS Regression Results[5] | | Number of Spectra | Range of Property |
|---|---|---|---|---|
| | Factors | SEC[2] | | |
| Gravity API | 8 | 0.50 | 297 | 22 - 28.6 |
| Carbon wt% | 8 | 0.08 | 245 | 0.0 - 1.8 |
| Sulphur wt% | 14 | 0.09 | 281 | 0.17 - 1.50 |
| Basic Nitrogen | 9 | 20.1 | 305 | 75 - 431 |
| Total Nitrogen | 9 | 56.9 | 303 | 270 - 1304 |
| IBP °F | 9 | 21.8 | 297 | 284 - 420 |
| 5% Point °F | 10 | 11.2 | 297 | 429 - 583 |
| 10% Point °F | 9 | 10.7 | 297 | 477 - 637 |
| 30% Point °F | 10 | 9.1 | 297 | 589 - 750 |
| 50% Point °F | 8 | 9.4 | 297 | 676 - 829 |
| 70% Point °F | 8 | 8.5 | 297 | 758 - 903 |
| 90% Point °F | 8 | 14.2 | 297 | 870 - 1071 |
| 95% Point °F | 11 | 19.6 | 297 | 926 - 1193 |
| FBP °F | 10 | 44.2 | 297 | 1050 - 1330 |

FIG. 9A

| | Regression Factors | Range wt% | Correlation Ratio[2] R[2(1)] |
|---|---|---|---|
| 1-Ring Core | 7 | 1.7 - 5.2 | 0.936 |
| 2-Ring Core | 11 | 2.2 - 6.8 | 0.892 |
| 3-Ring Core | 12 | 1.4 - 4.7 | 0.893 |
| 4-Ring Core | 7 | 0.4 - 5.6 | 0.913 |
| Polars | 5 | 0.0 - 4.3 | 0.811 |

FIG. 9B

ASSEMBLIES AND METHODS FOR ENHANCING FLUID CATALYTIC CRACKING (FCC) PROCESSES DURING THE FCC PROCESS USING SPECTROSCOPIC ANALYZERS

PRIORITY CLAIMS

This application is a continuation of U.S. Non-Provisional patent application Ser. No. 18/052,780, filed Nov. 4, 2022, titled "ASSEMBLIES AND METHODS FOR ENHANCING FLUID CATALYTIC CRACKING (FCC) PROCESSES DURING THE FCC PROCESS USING SPECTROSCOPIC ANALYZERS," which is a continuation-in-part of U.S. Non-Provisional application Ser. No. 17/652,431, filed Feb. 24, 2022, titled "METHODS AND ASSEMBLIES FOR DETERMINING AND USING STANDARDIZED SPECTRAL RESPONSES FOR CALIBRATION OF SPECTROSCOPIC ANALYZERS," which claims priority to and the benefit of U.S. Provisional Application No. 63/153,452, filed Feb. 25, 2021, titled "METHODS AND ASSEMBLIES FOR DETERMINING AND USING STANDARDIZED SPECTRAL RESPONSES FOR CALIBRATION OF SPECTROSCOPIC ANALYZERS," and U.S. Provisional Application No. 63/268,456, filed Feb. 24, 2022, titled "ASSEMBLIES AND METHODS FOR ENHANCING CONTROL OF FLUID CATALYTIC CRACKING (FCC) PROCESSES USING SPECTROSCOPIC ANALYZERS," the disclosures of which are incorporated herein by reference in their entireties; and further claims priority to and the benefit of U.S. Provisional Application No. 63/268,456, filed Feb. 24, 2022, titled "ASSEMBLIES AND METHODS FOR ENHANCING CONTROL OF FLUID CATALYTIC CRACKING (FCC) PROCESSES USING SPECTROSCOPIC ANALYZERS"; U.S. Provisional Application No. 63/268,827, filed Mar. 3, 2022, titled "ASSEMBLIES AND METHODS FOR OPTIMIZING FLUID CATALYTIC CRACKING (FCC) PROCESSES DURING THE FCC PROCESS USING SPECTROSCOPIC ANALYZERS"; and U.S. Provisional Application No. 63/268,875, filed Mar. 4, 2022, titled "ASSEMBLIES AND METHODS FOR ENHANCING CONTROL OF HYDROTREATING AND FLUID CATALYTIC CRACKING (FCC) PROCESSES USING SPECTROSCOPIC ANALYZERS," the disclosures of all three of which are incorporated herein by reference in their entireties.

TECHNICAL FIELD

The present disclosure relates to assemblies and methods to enhance fluid catalytic cracking (FCC) processes and, more particularly, to assemblies and methods to enhance FCC processes, during the FCC processes, using one or more spectroscopic analyzers.

BACKGROUND

Fluid catalytic cracking (FCC) processes may be used to produce desired petroleum-based intermediate and final products from hydrocarbon feeds. FCC processes are inherently complex because they involve a large number of variables and processing parameters associated with the hydrocarbon feeds and operation of FCC processing units and downstream processing units. Optimization, design, and control of fluid catalytic cracking (FCC) processing units may benefit from analytical models that describe conversion of hydrocarbon feeds to products. Analytical models, however, may only be useful if provided with timely and accurate information. If the information lacks sufficient accuracy, the analytical model may provide inaccurate outputs, for example, relating to hydrocarbon feedstock monitoring and control, and/or control of FCC and related processing units, and resulting products may lack desired properties. If the information is not provided to the analytical model in a sufficiently responsive manner, desired changes based on the information and model outputs may be delayed, resulting in extending the time during which the FCC processes are performed below optimum efficiency. Conventional laboratory analysis of the hydrocarbon feeds and related materials or processes may suffer from insufficiently responsive results to provide effective monitoring and control of the FCC process and related materials. For example, off-line laboratory analysis and related modeling studies may involve response times of hours, days, or even weeks, during which processing parameters are not optimized. As a result, the value of such monitoring and control may be reduced when used to monitor and control FCC processes in during operation.

Although some FCC processes may include devices and processes for monitoring and controlling the FCC process, Applicant has recognized that such devices and processes may suffer from delayed acquisition of useful information and/or inaccuracies due to the nature of the devices or processes. As a result, Applicant has recognized that there may be a desire to provide assemblies and methods for more accurately monitoring, controlling, and/or optimizing FCC processes and/or for more responsively determining properties and/or characteristics of hydrocarbon feeds, processing unit product materials, intermediate materials, FCC effluent, and/or upstream materials or downstream materials related to the FCC processes. Such assemblies and methods may result in enhanced control or optimization of FCC processes for more efficiently producing FCC products and/or downstream products.

The present disclosure may address one or more of the above-referenced considerations, as well as other possible considerations.

SUMMARY

Monitoring and control of FCC processes may be important for producing FCC-related products having certain characteristics or properties to meet industry and/or marketing standards. Using current systems and processes, it may be difficult to achieve desired standards because the systems and methods may suffer from delayed acquisition of useful information and/or inaccuracies due to the nature of the devices or processes. At least some embodiments of the present disclosure may advantageously provide assemblies and/or methods for monitoring, controlling, and/or optimizing FCC processes, such that the resulting FCC-related products have desired characteristics or properties that may be achieved more efficiently. In some embodiments, the assemblies and/or methods disclosed herein may result in acquisition of useful information and/or provide more accurate information for monitoring, controlling, and/or optimizing FCC processes while the FCC processes are occurring. This, in turn, may result in producing FCC-related products having desired characteristics or properties in a more efficient manner. For example, in at least some embodiments, at least some of the acquired information may be used to monitor and prescriptively control FCC processes, during the FCC processes, resulting in producing FCC-related products having desired characteristics or properties in a more economically efficient manner. For example, prescriptively controlling the FCC process assembly and/or the FCC process, during the FCC processes, according to some embodiments, may result in causing the FCC process to produce intermediate materials, the unit materials, and/or the downstream materials having properties within selected ranges of target properties, thereby to cause the FCC process to achieve material outputs that more accurately and responsively converge on one or more of the target properties.

According to some embodiments, a method to enhance a fluid catalytic cracking (FCC) process associated with a refining operation, during the FCC process, may include supplying a hydrocarbon feedstock to one or more first processing units associated with the refining operation. The hydrocarbon feedstock may have one or more hydrocarbon feedstock parameters, and the one or more first processing units may include an FCC processing unit. The method also may include operating the one or more first processing units to produce one or more corresponding unit materials. The one or more corresponding unit materials may include one or more of intermediate materials or unit product materials including FCC effluent. The method further may include conditioning a hydrocarbon feedstock sample to one or more of filter the hydrocarbon feedstock sample, change a temperature of the hydrocarbon feedstock sample, dilute the hydrocarbon feedstock sample in solvent, or degas the hydrocarbon feedstock sample. The method also may include analyzing the hydrocarbon feedstock sample via a first spectroscopic analyzer to provide hydrocarbon feedstock sample spectra. The method further may include conditioning a unit material sample to one or more of filter the unit material sample, change a temperature of the unit material sample, dilute the unit material sample in solvent, or degas the unit material sample. The method also may include analyzing the unit material sample via one or more of the first spectroscopic analyzer or a second spectroscopic analyzer to provide unit material sample spectra. The one or more of the first spectroscopic analyzer or the second spectroscopic analyzer may be calibrated to generate standardized spectral responses. The method still further may include predicting one or more hydrocarbon feedstock sample properties associated with the hydrocarbon feedstock sample based at least in part on the hydrocarbon feedstock sample spectra, and predicting one or more unit material sample properties associated with the unit material sample based at least in part on the unit material sample spectra. The method also may include prescriptively controlling, during the FCC process, via one or more FCC process controllers based at least in part on the one or more hydrocarbon feedstock parameters, the one or more hydrocarbon feedstock sample properties, and the one or more unit material sample properties, one or more of: (i) the one or more hydrocarbon feedstock parameters associated with the hydrocarbon feedstock supplied to the one or more first processing units; (ii) one or more intermediates properties associated with the intermediate materials produced by one or more of the first processing units; (iii) operation of the one or more first processing units; (iv) one or more unit materials properties associated with the one or more unit materials; or (v) operation of one or more second processing units positioned downstream relative to the one or more first processing units, so that the prescriptively controlling during the FCC process causes the FCC process to produce one or more of: (a) one or more intermediate materials each having one or more properties within a selected range of one or more target properties of the one or more intermediate materials; (b) one or more unit materials each having one or more properties within a selected range of one or more target properties of the one or more unit materials; or (c) one or more downstream materials each having one or more properties within a selected range of one or more target properties of the one or more downstream materials, thereby to cause the FCC process to achieve material outputs that more accurately and responsively converge on one or more of the target properties.

According to some embodiments, a fluid catalytic cracking (FCC) control assembly to enhance a fluid catalytic cracking (FCC) process associated with a refining operation, during the FCC process, may include a first spectroscopic analyzer positioned to receive a hydrocarbon feedstock sample of a hydrocarbon feedstock positioned to be supplied to one or more first processing units associated with the refining operation. The hydrocarbon feedstock may have one or more hydrocarbon feedstock parameters, and the one or more first processing units may include an FCC processing unit. The first spectroscopic analyzer also may be positioned to analyze the hydrocarbon feedstock sample to provide hydrocarbon feedstock sample spectra. The FCC control assembly further may include a second spectroscopic analyzer positioned to receive a unit material sample of one more unit materials produced by the one or more first processing units. The one or more unit materials may include one or more of intermediate materials or unit product materials comprising FCC effluent. The first spectroscopic analyzer and the second spectroscopic analyzer may be calibrated to generate standardized spectral responses. The second spectroscopic analyzer may be positioned to analyze the unit material sample to provide unit material sample spectra. The FCC control assembly further may include a sample conditioning assembly positioned to one or more of (i) condition the hydrocarbon feedstock sample, prior to being supplied to the first spectroscopic analyzer, to one or more of filter the hydrocarbon feedstock sample, change a temperature of the hydrocarbon feedstock sample, dilute the hydrocarbon feedstock sample in solvent, or degas the hydrocarbon feedstock sample; or (ii) condition the unit material sample, prior to being supplied to the second spectroscopic analyzer, to one or more of filter the unit material sample, change a temperature of the unit material sample, dilute the unit material sample in solvent, or degas the unit material sample. The FCC control assembly also may include an FCC process controller in communication with the first spectroscopic analyzer and the second spectroscopic analyzer. The FCC process controller may be configured to predict one or more hydrocarbon feedstock sample properties associated with the hydrocarbon feedstock sample based at least in part on the hydrocarbon feedstock sample spectra and predict one or more unit material sample properties associated with the unit material sample based at least in part on the unit material sample spectra. The FCC process controller further may be configured to prescriptively control, during the FCC process, based at least in part on the one or more hydrocarbon feedstock parameters, the one or more hydrocarbon feedstock sample properties, and the one or more unit material sample properties, one or more of: (i) the one or more hydrocarbon feedstock parameters associated with the hydrocarbon feedstock supplied to the one or more first processing units; (ii) one or more intermediates properties associated with the intermediate materials produced by one or more of the first processing units; (iii) operation of the one or more first processing units; (iv) one or more unit materials properties associated with the one or more unit materials; or (v) operation of one or more second processing units positioned downstream relative to the one or more first processing units, so that the prescriptively controlling during the FCC process causes the FCC process to produce one or more of: (a) one or more intermediate materials each having one or more properties within a selected range of one or more target properties of the one or more intermediate materials; (b) one or more unit materials each having one or more properties within a selected range of one or more target properties of the one or more unit materials; or (c) one or more downstream materials each having one or more properties within a selected range of one or more target properties of the one or more downstream materials, thereby to cause the FCC process to achieve material outputs that more accurately and responsively converge on one or more of the target properties.

According to some embodiments, a fluid catalytic cracking (FCC) process controller to enhance an FCC process associated with a refining operation, the FCC process controller being in communication with one or more spectroscopic analyzers and one or more first processing units, may be configured to predict one or more hydrocarbon feedstock sample properties associated with a hydrocarbon feedstock sample based at least in part on hydrocarbon feedstock sample spectra generated by the one or more spectroscopic analyzers. The FCC process controller further may be configured to predict one or more unit material sample properties associated with a unit material sample based at least in part on unit material sample spectra generated by the one or more spectroscopic analyzers. The FCC process controller also may be configured to prescriptively control, during the FCC process, based at least in part on one or more hydrocarbon feedstock parameters, the one or more hydrocarbon feedstock sample properties, and the one or more unit material sample properties, one or more of: (i) the one or more hydrocarbon feedstock parameters associated with hydrocarbon feedstock supplied to the one or more first processing units; (ii) one or more intermediates properties associated with intermediate materials produced by one or more of the first processing units; (iii) operation of the one or more first processing units; (iv) one or more unit materials properties associated with the one or more unit materials; or (v) operation of one or more second processing units positioned downstream relative to the one or more first processing units, so that the prescriptively controlling during the FCC process causes the FCC process to produce one or more of: (a) one or more intermediate materials each having one or more properties within a selected range of one or more target properties of the one or more intermediate materials; (b) one or more unit materials each having one or more properties within a selected range of one or more target properties of the one or more unit materials; or (c) one or more downstream materials each having one or more properties within a selected range of one or more target properties of the one or more downstream materials, thereby to cause the FCC process to achieve material outputs that more accurately and responsively converge on one or more of the target properties.

According to some embodiments, a fluid catalytic cracking (FCC) processing assembly for performing an FCC process associated with a refining operation may include one or more first FCC processing units associated with the refining operation including one or more of an FCC reactor or an FCC regenerator. The FCC processing assembly also may include a first spectroscopic analyzer positioned to receive, during the FCC process, a hydrocarbon feedstock sample of a hydrocarbon feedstock. The hydrocarbon feedstock may have one or more hydrocarbon feedstock parameters and may be supplied to the one or more first FCC processing units. The first spectroscopic analyzer further may be positioned to analyze during the FCC process the hydrocarbon feedstock sample to provide hydrocarbon feedstock sample spectra. The FCC processing assembly also may include a second spectroscopic analyzer positioned to receive during the FCC process a unit material sample of one more unit materials produced by the one or more first FCC processing units. The one or more unit materials may include one or more of intermediate materials or unit product materials including FCC effluent. The first spectroscopic analyzer and the second spectroscopic analyzer may be calibrated to generate standardized spectral responses. The second spectroscopic analyzer also may be positioned to analyze during the FCC process the unit material sample to provide unit material sample spectra. The FCC processing assembly further may include a sample conditioning assembly positioned to one or more of (i) condition the hydrocarbon feedstock sample, prior to being supplied to the first spectroscopic analyzer, to one or more of filter the hydrocarbon feedstock sample, change a temperature of the hydrocarbon feedstock sample, dilute the hydrocarbon feedstock sample in solvent, or degas the hydrocarbon feedstock sample; or (ii) condition the unit material sample, prior to being supplied to the second spectroscopic analyzer, to one or more of filter the unit material sample, change a temperature of the unit material sample, dilute the unit material sample in solvent, or degas the unit material sample. The FCC processing assembly also may include an FCC process controller in communication with the first spectroscopic analyzer and the second spectroscopic analyzer during the FCC process. The FCC process controller may be configured to predict during the FCC process one or more hydrocarbon feedstock sample properties associated with the hydrocarbon feedstock sample based at least in part on the hydrocarbon feedstock sample spectra. The FCC process controller also may be configured to predict during the FCC process one or more unit material sample properties associated with the unit material sample based at least in part on the unit material sample spectra. The FCC process controller further may be configured to prescriptively control, during the FCC process, based at least in part on the one or more hydrocarbon feedstock parameters, the one or more hydrocarbon feedstock sample properties, and the one or more unit material sample properties, one or more of: (i) the one or more hydrocarbon feedstock parameters associated with the hydrocarbon feedstock supplied to the one or more first FCC processing units; (ii) one or more intermediates properties associated with the intermediate materials produced by one or more of the first FCC processing units; (iii) operation of the one or more first FCC processing units; (iv) one or more unit materials properties associated with the one or more unit materials; or (v) operation of one or more second processing units positioned downstream relative to the one or more first FCC processing units, so that the prescriptively controlling during the FCC process causes the FCC process to produce one or more of: (a) one or more intermediate materials each having one or more properties within a selected range of one or more target properties of the one or more intermediate materials; (b) one or more unit materials each having one or more properties within a selected range of one or more target properties of the one or more unit materials; or (c) one or more downstream materials each having one or more properties within a selected range of one or more target properties of the one or more downstream materials, thereby to cause the FCC process to achieve material outputs that more accurately and responsively converge on one or more of the target properties.

Still other aspects, examples, and advantages of these exemplary aspects and embodiments are discussed in more detail below. It is to be understood that both the foregoing information and the following detailed description are merely illustrative examples of various aspects and embodiments, and are intended to provide an overview or framework for understanding the nature and character of the claimed aspects and embodiments. Accordingly, these and other objects, along with advantages and features of the present disclosure herein disclosed, may become apparent through reference to the following description and the accompanying drawings. Furthermore, it is to be understood that the features of the various embodiments described herein are not mutually exclusive and may exist in various combinations and permutations.

BRIEF DESCRIPTION OF THE DRAWINGS

The accompanying drawings, which are included to provide a further understanding of the embodiments of the present disclosure, are incorporated in and constitute a part of this specification, illustrate embodiments of the present disclosure, and together with the detailed description, serve to explain principles of the embodiments discussed herein. No attempt is made to show structural details of this disclosure in more detail than may be necessary for a fundamental understanding of the exemplary embodiments discussed herein and the various ways in which they may be practiced. According to common practice, the various features of the drawings discussed below are not necessarily drawn to scale. Dimensions of various features and elements in the drawings may be expanded or reduced to more clearly illustrate the embodiments of the disclosure.

FIG. 6A is a table illustrating spectroscopic analysis data associated with an example FCC process including samples of hydrotreater charges and products, and FCC feeds used to control relative amounts of each hydrocarbon class shown in weight percent, according to embodiments of the disclosure.

FIG. 6B is a table illustrating minimum and maximum amounts for a calibration set shown in weight percent for example hydrocarbon classes related to the data shown in FIG. 6A, according to embodiments of the disclosure.

FIG. 9A is a table showing NIR regression statistics for each of a plurality of example properties, according to embodiments of the disclosure.

FIG. 9B is a table showing NIR regression statistics for each of a plurality of example properties, according to embodiments of the disclosure.

DETAILED DESCRIPTION

Figure 1:
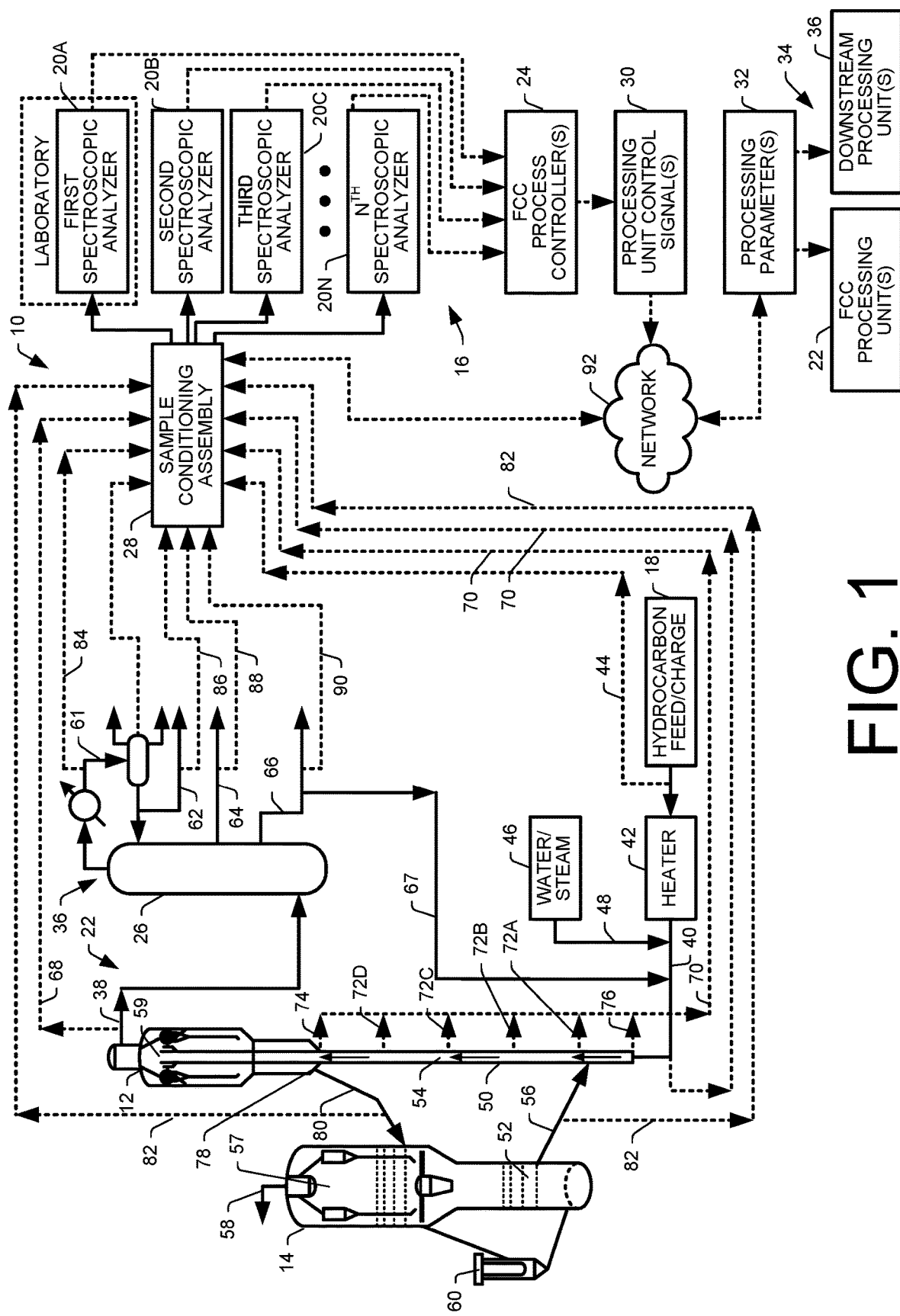
FIG. 1 is a schematic block diagram illustrating an example FCC processing assembly including an example FCC reactor, an example catalyst regenerator, and an example FCC control assembly, according to embodiments of the disclosure.

Referring now to the drawings in which like numerals indicate like parts throughout the several views, the following description is provided as an enabling teaching of exemplary embodiments, and those skilled in the relevant art will recognize that many changes may be made to the embodiments described. It also will be apparent that some of the desired benefits of the embodiments described may be obtained by selecting some of the features of the embodiments without utilizing other features. Accordingly, those skilled in the art will recognize that many modifications and adaptations to the embodiments described are possible and may even be desirable in certain circumstances. Thus, the following description is provided as illustrative of principles of the embodiments and not in limitation thereof.

The phraseology and terminology used herein is for the purpose of description and should not be regarded as limiting. Any examples of operating parameters and/or environmental conditions are not exclusive of other parameters/conditions of the disclosed embodiments. Additionally, it should be understood that references to "one embodiment," "an embodiment," "certain embodiments," or "other embodiments" of the present disclosure are not intended to be interpreted as excluding the existence of additional embodiments that also incorporate the recited features. When introducing elements of various embodiments of the present disclosure, the articles "a," "an," "the," and "said" are intended to mean that there are one or more of the elements. As used herein, the term "plurality" refers to two or more items or components. A multi-component sample may refer to a single (one) sample including a plurality of components, such as two or more components. The terms "comprising," "including," "carrying," "having," "containing," and "involving," whether in the written description or the claims and the like, are open-ended terms, in particular, to mean "including but not limited to," unless otherwise stated. Thus, the use of such terms is meant to encompass the items listed thereafter, and equivalents thereof, as well as additional items. The transitional phrases "consisting of" and "consisting essentially of," are closed or semi-closed transitional phrases, respectively, with respect to any claims. Use of ordinal terms such as "first," "second," "third," and the like in the claims to modify a claim element does not necessarily, by itself, connote any priority, precedence, or order of one claim element over another or the temporal order in which acts of a method are performed, but are used merely as labels to distinguish one claim element having a certain name from another element having a same name (but for use of the ordinal term) to distinguish claim elements.

Certain terminology used herein may have definitions provided for the purpose of illustration and not limitation. For example, as used herein, the "sampling circuit" may refer to an assembly for facilitating separation of a sample of a material, a sample of a composition of material, and/or a sample of an FCC product, for example, for processing and/or analysis of the sample.

As used herein, the term "sample conditioner" may refer to an assembly for facilitating preparation of a sample for analysis, for example, to improve the accuracy of analysis of the sample and/or to provide consistency and/or repeatability of the analysis of the sample or more than one sample.

As used herein, the term "spectroscopic analyzer" may refer an analyzer that may be used to measure or predict one or more properties of a sample of, for example, a material, a composition of materials, and/or an FCC product. In some embodiments, the spectroscopic analyzers may be used online or in a laboratory setting. "Spectroscopic analyzer" may refer in some instances to a spectroscopic analyzer assembly, which may include a spectroscopic analyzer and an analyzer controller in communication with one or more spectroscopic analyzers. The analyzer controller may be configured for use with a corresponding spectroscopic analyzer for pre-processing and/or post-processing steps or procedures related to a spectroscopic analysis, as will be understood by those skilled in the art. In some embodiments, the analyzer controller may be physically connected to the spectroscopic analyzer. In some such embodiments, the spectroscopic analyzer may include a housing, and at least a portion of the analyzer controller may be contained in the housing. In some embodiments, the analyzer controller may be in communication with the spectroscopic analyzer via a hard-wired communications link and/or wireless communications link. In some embodiments, the analyzer controller may be physically separated from the spectroscopic analyzer and may be in communication with the spectroscopic analyzer via a hard-wired communications link and/or a wireless communications link. In some embodiments, physical separation may include being spaced from one another, but within the same building, within the same facility (e.g., located at a common manufacturing facility, such as a refinery), or being spaced from one another geographically (e.g., anywhere in the world). In some physically separated embodiments, both the spectroscopic analyzer and the analyzer controller may be linked to a common communications network, such as a hard-wired communications network and/or a wireless communications network. Such communications links may operate according to any known hard-wired communications protocols and/or wireless communications protocols, as will be understood by those skilled in the art.

As used herein, the term "sample introducer" may refer to a component or assembly that may be used to facilitate the provision of a conditioned sample (portion or stream) to one or more spectroscopic analyzers for analysis.

As used herein, the term "sample stream" may refer to a portion of a sample stream supplied to one or more spectroscopic analyzers for spectroscopic analysis by the one or more spectroscopic analyzers.

As used herein, the term "predicting" may refer to measuring, estimating, determining, and/or calculating one or more properties of a material, a composition of materials, and/or an FCC product based on, for example, a mathematical relationship, a correlation, an analytical model, and/or a statistical model.

As used herein, the term "sample probe" may refer to a component or an interface used to facilitate collection of a sample for analysis by, for example, one or more spectroscopic analyzers.

As used herein, the term "analyzer probe" may refer to a component of one or more spectroscopic analyzers that facilitates direction of electromagnetic radiation (e.g., light energy) from a source through a sample stream (e.g., a conditioned sample stream) to detect and/or measure one or more of absorbance, transmittance, transflectance, reflectance, or scattering intensity associated with the sample stream.

As used herein, the term "sample cell" may refer to a receptacle or cell for receipt of samples for analysis or measurement, for example, by a spectroscopic analyzer.

As used herein, the term "on-line" may refer to equipment and/or processes that are physically located at or adjacent to processing assemblies during operation and, for at least some embodiments, may be capable of providing real-time and/or near real-time analysis and/or data capable of real-time and/or near real-time analysis. For example, in some embodiments, an on-line spectroscopic analyzer may receive one or more sample streams directly from a processing assembly or process and analyze the one or more sample streams in real-time or near real-time to provide results that may, in some embodiments, be used to at least partially control operation of one or more processing assemblies and/or one or more processes in real-time or near real-time. In some embodiments, the on-line spectroscopic analyzer or analyzers may be physically located in a laboratory setting. This may be either extractive (e.g., a sample stream is drawn off of a processing unit and supplied to a spectroscopic analyzer and/or to one or more sensors) or in situ (e.g., a probe of a spectroscopic analyzer or one or more sensors is present in a conduit associated with the processing assembly).

As used herein, the term "at-line" may refer to equipment and/or processes that are physically located at or adjacent to processing assemblies during operation, but which, for at least some embodiments, are not capable of providing real-time and/or near real-time analysis and/or are not capable providing data capable of real-time and/or near real-time analysis. For example, in an "at-line" process, a "field analyzer" located physically at or adjacent a processing assembly may be used to analyze a sample withdrawn from the processing assembly or process and manually taken to the field analyzer for analysis. In some embodiments, the at-line spectroscopic analyzer or analyzers may be physically located in a laboratory setting. For example, in some embodiments, an at-line spectroscopic analyzer would not receive a sample stream directly from processing assemblies, but instead, would manually receive a sample manually withdrawn from a processing unit by an operator and manually taken or delivered by the operator to the at-line spectroscopic analyzer.

FIG. 1 is a schematic block diagram illustrating an example fluid catalytic cracking (FCC) processing assembly 10 including an example FCC reactor 12, an example catalyst regenerator 14, and an example FCC control assembly 16, according to embodiments of the disclosure. In some embodiments, the example FCC processing assembly 10 may be used in association with a refinery. For example, catalytic cracking may be used to convert hydrocarbon feedstock or feed/charge 18, for example, heavy feeds including hydrocarbons having boiling points ranging from about 600 degrees Fahrenheit (F) to about 1,050 degrees, such as, for example, atmospheric gas oil, vacuum gas oil, coker gas oil, lube extracts, and/or slop streams, into lighter products, such as, for example, light gases, olefins, gasoline, distillate, and/or coke, by catalytically cracking large molecules into smaller molecules. In some embodiments, catalytic cracking may be performed at relatively low pressures (e.g., pressures ranging from about 15 pounds per square inch (psig) to about 30 psig), for example, in the absence of externally supplied hydrogen ($H_2$), or in some embodiments (e.g., including hydrocracking), in which hydrogen is added during one or more cracking steps.

In some embodiments, the hydrocarbon feed/charge 18 may include FCC feedstocks including a fraction of crude oil having boiling points ranging from about 650 degrees F. to about 1,000 degrees F., which, in some embodiments, may be relatively free of coke precursors and/or heavy metal contamination, such as, for example, feedstock sometimes referred to as "vacuum gas oil" (VGO), which, in some instances, may be generally obtained from crude oil by distilling off the fractions of the feedstock having boiling points below 650 degrees F. at atmospheric pressure and thereafter separating by further vacuum distillation from the heavier fractions a cut having boiling points ranging from about 650 degrees F. to about 900 degrees to 1,025 degrees F., for example, as will be understood by those skilled in the art. Fractions of the feedstock having boiling points ranging from above about 900 degrees F. to about 1,025 degrees F. may be used for other purposes, such as, for example, asphalt, residual fuel oil, #6 fuel oil, and/or marine Bunker C fuel oil. In some embodiments, some of the cuts having higher boiling points may be used, for example, as feedstock in association with FCC processes that use carbo-metallic oils formed by reduced crude conversion (RCC), for example, using a progressive flow-type reactor having an elongated reaction chamber. In some embodiments, the hydrocarbon feed/charge 18 may be selected to increase or optimize production of propylene by an FCC processing assembly, such as, for example, the hydrocarbon feedstock/charge 18 may be selected to contain feedstocks having a particular aromatics content, a particular hydrogen content, and/or other particular feedstock characteristics known to those skilled in the art to increase, enhance, or optimize propylene production by an FCC processing assembly.

In some embodiments, one or more analytical models (e.g., one or more kinetic models) may be used to predict (or determine) process yields as a function of, for example, feedstock quality (e.g., feedstock content and/or properties), catalyst conditions, and/or processing conditions or parameters. In some embodiments, an optimizer algorithm may be incorporated into or used with the one or more analytical models to determine an improved or optimum combination of, for example, feedstock rate, processing conditions or parameters, and/or catalyst properties for performing the FCC process. The use of one or more spectroscopic analyzers, for example, as described herein to provide accurate information related to hydrocarbon feedstock properties and/or parameters, accurate unit material property information (e.g., intermediates and/or product yields), and/or other related analytical data may facilitate determining the improved or optimum combination(s) of, for example, feedstock rate, processing conditions or parameters, and/or catalyst properties for performing the FCC process. Moreover, in some embodiments, the one or more spectroscopic analyzers, alone or in combination with other sources of operational information, may facilitate improvement or optimization during the FCC process (e.g., in real-time), which may reduce or eliminate inefficient operation of the FCC process that may result from delaying changes to properties and/or parameters associated with the materials and processing units due to delays with receiving test results from, for example, off-line laboratory testing.

In some embodiments of the assemblies and processes described herein, one or more spectroscopic analyzers may be used on-line to facilitate control, improvement, and/or optimization of the FCC process during the FCC process. In some embodiments, the spectroscopic analyzer(s) may be used to relatively precisely predict or determine process properties and/or parameters associated with materials involved with the FCC process, including the hydrocarbon feedstock, intermediate materials produced by the one or more FCC processing units, and/or products produced by the FCC processing units and/or downstream processing units. Such properties and parameters may include, for example, feed quality, feed rate, FCC operating conditions, and/or FCC product properties. Other properties and parameters are contemplated, such as those described herein, as well as others.

In some embodiments, measurement, for example, during the FCC process, of properties and processing parameters (e.g., processing conditions) may be used to manipulate or control the FCC process. In some embodiments, advanced process control-related (APC-related) techniques may be used to improve, optimize, and/or maximize the FCC process against processing constraints, such as, for example, processing unit capabilities. Control during the FCC process, for example, leveraging APC-related techniques, may facilitate control of the FCC process to balance intermediates and/or products yield(s), recovery, capacity, and/or efficiency, for example, selected from multiple process variables and equipment capabilities, which may include material properties and/or parameters associated with the feedstock, catalyst, intermediates, and/or products, as well as operational parameters associated with the one or more FCC processing units.

For example, in some embodiments, a spectroscopic analyzer may be used to collect spectra of samples of the hydrocarbon feedstock for the FCC process. The collected spectral data may be indicative of one or more properties and/or parameters associated with the hydrocarbon feedstock, and may be correlated to traditional laboratory tests (e.g., performed via one or more primary test methods), including, for example, HPLC Heavy Distillate Analyzer (HDA) results for aromatic core type (e.g., 1-ring core, 2-ring core, 3-ring core, 4-ring core, and/or polars), ASTM D2887 high temperature simulated distillation, basic nitrogen, total nitrogen, API gravity, total sulfur, mean cell residence time (MCRT), and percent of coker gas oil in vacuum gas oil (VGO). The spectroscopic analyzer(s) may be used to monitor the hydrocarbon feedstock more responsively, more accurately, and/or more efficiently, as compared to performing laboratory tests.

In some embodiments, certain wavelengths, wavenumbers, and/or frequencies (or ranges thereof) may be useful for controlling, improving, and/or optimizing the FCC process, for example, by controlling operation of one or more FCC processing units. For example, in some embodiments, a process may be used for controlling on-line hydrocarbon feedstock, intermediates, and unit materials (e.g., FCC products) exhibiting absorption in the near infrared region. (Other regions are contemplated.) For example, a method for controlling on-line an FCC process (e.g., during the FCC process) may include measuring absorbances of the hydrocarbon feed using a spectroscopic analyzer at wavelengths ranging from about 780 nanometers (nm) to about 2,500 nm), and outputting one or more signals indicative of the absorbances. The method may further include subjecting the one or more signals to mathematical treatment or manipulation, such as, for example, taking one or more derivatives, smoothing, and/or performing baseline correction of the one or more signals. The method further may include using an analytical model to determine one or more chemical and/or physical properties of the hydrocarbon feed, intermediates, and/or unit materials (e.g., products) based at least in part on the treated and/or manipulated one or more signals, and outputting a processed signal. The method further may include controlling on-line, based at least in part on the processed signal, at least one property and/or parameter associated with the hydrocarbon feed, the intermediates, and/or the unit materials, and/or one or more processing unit parameters.

In some embodiments, the FCC process may be at least partially controlled by selecting a hydrocarbon feedstock having certain properties and/or parameters based at least in part on one or more characteristics associated with one or more of the FCC processing units, for example, as well as controlling one or more processing parameters associated with the one or more FCC processing units.

In some embodiments, one or more FCC processing parameters and/or conditions may be varied to effect products resulting for the FCC process. For example, operating under relatively more severe cracking conditions, for example, by increasing the processing temperatures, may result in providing a gasoline product having a relatively higher octane rating, while increasing conversion may result in providing relatively more olefins for alkylate production, as well as relatively more gasoline and potential alkylate. Catalytic cracking may also be affected by inhibitors, which may be naturally present in the hydrocarbon feed and/or or may be added. Generally, as the boiling range of the hydrocarbon feed increases, the concentration of inhibitors naturally therein may also increase. The effects of inhibitors may be temporary or lasting, depending on, for example, the type of inhibitor present. Nitrogen inhibitors may generally provide temporary effects, while heavy metals, such as nickel, vanadium, iron, copper, etc., which may quantitatively transfer from the hydrocarbon feed to the catalyst may provide a more lasting effect. Metals poisoning may result in relatively higher dry gas yields, relatively higher hydrogen factors, relatively higher coke yields as a percent of conversion, and/or relatively lower gasoline yields. Coke precursors such as asphaltenes may tend to break down into coke during cracking, which may be deposited on the catalyst, reducing its activity.

In some embodiments, an inventory of particulate catalyst may be generally continuously cycled between the FCC reactor and the catalyst regenerator. In some FCC processes, hydrocarbon feedstock may contact catalyst in the FCC reactor, for example, at a temperature ranging from about 425 degrees C. to about 600 degrees C., (e.g., from about 460 degrees C. to about 560 degrees C.). As the hydrocarbons crack, carbonaceous hydrocarbons and/or coke may be deposited on the catalyst. The cracked products may be separated from the coked catalyst. The coked catalyst may be stripped of volatiles, for example, with steam, and thereafter may be regenerated. For example, in the catalyst regenerator, the coke may be burned from the catalyst using oxygen-containing gas, such as air. The coke burns off, restoring catalyst activity and heating the catalyst to, for example, as temperature ranging from about 500 degrees C. to about 900 degrees C. (e.g., from about 600 degrees C. to about 750 degrees C.). As described herein, flue gas formed by burning coke in the catalyst regenerator may thereafter be discharged into the atmosphere.

In some embodiments, the one or more FCC processing units may use zeolite-containing catalyst having relatively high activity and/or selectivity. Such catalysts may be relatively more effective when the amount of coke on the catalyst after regeneration is relatively low, such as, for example, less than about 0.1 wt % (e.g., less than about 0.05 wt %). To regenerate catalysts to such relatively low residual carbon levels, and to burn carbon monoxide (CO) relatively completely to form carbon dioxide ($CO_2$) within the catalyst regenerator (e.g., to conserve heat and/or minimize air pollution), high-efficiency regenerators and/or CO combustion promoters may be used. In some embodiments, FCC processing units may be operated in a complete CO combustion mode, for example, such that the mole ratio of $CO_2$-to-CO is at least 10. In some embodiments, the CO may be burned within the catalyst regenerator to conserve heat and/or minimize undesirable emissions. In some embodiments, CO may be burned in the catalyst regenerator by adding platinum catalyst.

In some embodiments, a desired product slate may be determined based at least in part on spectroscopic analysis of one or more of the unit materials (e.g., the FCC products), which may be used for monitoring and/or controlling one or more aspects of the FCC process, such as one or more processing parameters for operation of one or more of the FCC processing units.

In some embodiments, one or more spectroscopic analyzers may be used to determine one or more properties and/or one or more parameters associated with the hydrocarbon feedstock. The one or more properties and/or parameters may be used to monitor and/or control operation of one or more of the FCC processing units. The hydrocarbon feed properties and/or parameters may variables used for controlling the FCC process and may include, for example, but are not limited to, weight percent (wt. %) or volume percent (vol. %) of mono-aromatics, di-aromatics, tri-aromatics, benzothiophenes, di-benzothiophenes, paraffins, naphthenes, aromatics, and/or nitrogen content. Unit material properties and/or unit material parameters (e.g., intermediates and/or products of the FCC process and/or downstream processes) may include, for example, but are not limited to, amount of butane ($C_4$) free gasoline (volume), amount of total $C_4$ (volume), amount of dry gas (wt), amount of coke (wt), an amount of propylene (e.g., propylene yield), gasoline octane, amount of light fuel oil (LFO), amount of heavy fuel oil (HFO), amount of hydrogen sulfide ($H_2S$), amount of sulfur in the LFO, and/or the aniline point of the LFO.

As schematically shown in FIG. 1, the example fluid catalytic cracking (FCC) assembly 10 includes the example FCC reactor 12 and the example catalyst regenerator 14, and the example FCC control assembly 16 may be used to at least partially (e.g., semi-autonomously, autonomously, and/or fully) control an FCC process performed by the FCC processing assembly 10. As shown in FIG. 1, in some embodiments, the FCC control assembly 16 may include one or more spectroscopic analyzers 20 (e.g., 20A through 20N as shown), which may be used to receive (e.g., on-line), analyze, and generate one or more spectra indicative of properties and/or parameters of samples of the feed/charge 18 (e.g., the hydrocarbon feedstock) and/or indicative of properties of samples of one or more unit materials produced by one or more FCC processing units 22. In some embodiments, one or more of the spectroscopic analyzers 20 may be configured to receive more than a single stream of material for analysis. In some such embodiments, a multiplexer may be associated with the one or more spectroscopic analyzers 20 to facilitate analysis of two or streams of material by a single spectroscopic analyzer. In some embodiments, one or more of the spectroscopic analyzers 20A though 20N may be used and/or located online and/or in a laboratory setting. In some embodiments, the one or more unit materials may include one or more of intermediate materials or unit product materials, for example, including FCC effluent and/or other associated materials taken from any point or any stage of the FCC process. In some embodiments, two or more of the spectroscopic analyzers 20A through 20N may be calibrated to generate standardized spectral responses, for example, as described herein. For example, a first spectroscopic analyzer 20A and additional spectroscopic analyzers 20B through 20N may be calibrated to generate standardized spectral responses, for example, such that each of the first spectroscopic analyzer 20A and the additional spectroscopic analyzers 20B through 20N output a respective corrected material spectrum, including a plurality of signals indicative of a plurality of material properties of an analyzed material based at least in part on the corrected material spectrum, such that the plurality of material properties or parameters of the analyzed material outputted by the first spectroscopic analyzer 20A are substantially consistent with a plurality of material properties of the analyzed material outputted by the additional spectroscopic analyzers 20B through 20N. In some embodiments, one of more of the spectroscopic analyzers 20A through 20N may be located in a laboratory setting, for example, as schematically depicted in FIG. 1 with respect to the first spectroscopic analyzer 20A.

In some embodiments, the one or more hydrocarbon feed/charge 18 sample properties and/or the one or more unit material sample properties may include a content ratio indicative of relative amounts of one or more hydrocarbon classes present in one or more of the hydrocarbon feed/charge 18 sample and/or the unit material samples. Other hydrocarbon feed/charge 18 sample properties and/or unit material sample properties are contemplated. Although many embodiments described herein use more than one spectroscopic analyzer, it is contemplated that a single spectroscopic analyzer may be used for at least some embodiments of the FCC processes described herein. One or more of the spectroscopic analyzers 20A through 20N may include one or more near-infrared (NIR) spectroscopic analyzers, one or more mid-infrared (mid-IR) spectroscopic analyzers, one or more combined MR and mid-IR spectroscopic analyzers, and/or one or more Raman spectroscopic analyzers. In some embodiments, one or more of the spectroscopic analyzer(s) 20A through 20N may include a Fourier Transform near infrared (FTNIR) spectroscopic analyzer, a Fourier Transform infrared (FTIR) spectroscopic analyzer, or an infrared (IR) type spectroscopic analyzer. In some embodiments, one or more of the spectroscopic analyzers 20A through 20N may be ruggedized for use in an on-line analyzing process and/or in a laboratory setting, and in some embodiments, one or more of the spectroscopic analyzers 20A through 20N may be at least partially housed in a temperature-controlled and/or explosion-resistant cabinet. For example, some embodiments of the one or more spectroscopic analyzers 20A through 20N may be configured to withstand operating conditions, such as, for example, temperature, pressure, chemical compatibility, vibrations, etc., that may be present in an on-line environment and/or in a laboratory setting. For example, the one or more spectroscopic analyzers 20A through 20N may be designed to be operated in a particular environment of use and/or an environment that meets area classifications, such as, for example, a Class 1, Division 2 location. In some embodiments, a photometer with present optical filters moving successively into position, may be used as a type of spectroscopic analyzer.

As shown in FIG. 1, in some embodiments, the FCC processing assembly 10 also may include one or more FCC process controllers 24 in communication with one or more of the spectroscopic analyzers 20A through 20N and that control one or more aspects of the FCC process. For example, in some embodiments, the FCC process controller(s) 24 may be configured to predict (or determine) one or more hydrocarbon feedstock sample properties and/or parameters associated with samples of the hydrocarbon feed/charge 18, for example, based at least in part on hydrocarbon feedstock sample spectra generated by the one or more spectroscopic analyzers 20A through 20N (e.g., first spectroscopic analyzer 20A, as shown in FIG. 1). In some embodiments, the FCC process controller(s) 24 may be configured to predict (or determine) one or more unit material sample properties and/or parameters associated with the unit material samples based at least in part on the unit material sample spectra generated by the one or more spectroscopic analyzers 20A through 20N. For example, as described herein, each of the one or more spectroscopic analyzer(s) 20A through 20N may output a signal communicated to the one or more FCC process controller(s) 24, which may mathematically manipulate the signal (e.g., take a first or higher order derivative of the signal) received from the spectroscopic analyzer, and subject the manipulated signal to a defined model to generate material properties and/or parameters of interest, for example, as described herein. In some embodiments, such models may be derived from signals obtained from spectroscopic analyzer measurement of the one or more unit materials (e.g., the intermediates and/or the cracking products). In some examples, an analyzer controller in communication with a corresponding one or more of the spectroscopic analyzer(s) 20A through 20N may be configured to receive the signal output by the one or more corresponding spectroscopic analyzers and mathematically manipulate the signal, for example, prior to the one or more FCC process controller(s) 24 receiving the signal.

In some embodiments, the FCC process controller(s) 24 may be configured to prescriptively control, during the FCC process, via one or more FCC process controllers 24, based at least in part on the one or more hydrocarbon feedstock parameters, the one or more hydrocarbon feedstock sample properties, and/or the one or more unit material sample properties, (i) the one or more hydrocarbon feedstock parameters associated with the hydrocarbon feedstock 18 supplied to the one or more FCC processing units 22; (ii) one or more intermediates properties associated with the intermediate materials produced by one or more of the FCC processing units 22; (iii) operation of the one or more FCC processing units 22; (iv) one or more unit materials properties associated with the one or more unit materials; and/or (v) operation of one or more processing units positioned downstream relative to the one or more FCC processing units 22 such as, for example, a fractionator 26 configured to separate various hydrocarbon products of FCC effluent received from the FCC reactor 12. In some embodiments, the prescriptive control may result in causing the FCC process to produce one or more of: (a) one or more intermediate materials each having one or more properties within a selected range of one or more target properties of the one or more intermediate materials; (b) one or more unit materials each having one or more properties within a selected range of one or more target properties of the one or more unit materials; or (c) one or more downstream materials each having one or more properties within a selected range of one or more target properties of the one or more downstream materials. In some embodiments, this may result causing the FCC process to achieve material outputs that more accurately and responsively converge on one or more of the target properties. In some embodiments, the prescriptive control may result in optimizing one or more target properties of the one or more intermediate materials, one or more target properties of the one or more unit materials, and/or one or more target properties of one or more downstream materials produced by the one or more second processing units, for example, thereby to optimize the FCC process to achieve material outputs that more accurately and responsively converge on one or more of the target properties.

In some embodiments, the FCC processing assembly 10 further may include a sample conditioning assembly 28 configured to condition the hydrocarbon feed/charge 18, for example, prior to being supplied to the one or more spectroscopic analyzer(s) 20A through 20N. In some embodiments, the sample conditioning assembly 28 may be configured to filter samples of the hydrocarbon feed/charge 18, change (e.g., control) the temperature of the samples of the hydrocarbon feed/charge 18, dilute the samples of the hydrocarbon feed/charge 18 in solvent (e.g., on-line and/or in a laboratory setting), and/or degas the samples of the hydrocarbon feed/charge 18. In some embodiments, one or more sample conditioning procedures may be performed without using the sample conditioning assembly 28, for example, in a laboratory setting. In some embodiments, the sample conditioning assembly 28 also may be configured to condition samples of the unit materials, for example, prior to being supplied to the one or more spectroscopic analyzer(s) 20A through 20N, to filter the samples of the unit materials, to change (e.g., control) the temperature of the samples of the unit materials, dilute the samples of the unit materials in solvent, and/or degas the samples of the unit materials. With respect to diluting samples, for example, in some embodiments, this may include diluting samples of the hydrocarbon feed/charge 18 and/or the unit materials, such dilution may be used for analysis in a laboratory setting, and in some embodiments, the dilution may be performed in a laboratory setting. In some such embodiments, the resulting spectra of the diluted sample may be manipulated, for example, to back out account for the infrared absorption or the Raman scattering due to the presence of the solvent used. In some embodiments, sample conditioning by the sample conditioning assembly 28 may result in more accurate, more repeatable, and/or more consistent analysis of the hydrocarbon feed/charge 18 and/or the one or more unit materials, which may in turn result in improved and/or more efficient control and/or more accurate control of the FCC process. Example embodiments of a sample conditioning assembly 28 are described herein, for example, with respect to FIG. 3. In some embodiments, the one or more FCC process controller(s) 24 may be configured to control at least some aspects of operation of the sample conditioning assembly 28, for example, as described herein.

As shown in FIG. 1, in some embodiments, the one or more FCC process controller(s) 24 may be configured to prescriptively control one or more process parameters associated with operation of one or more of the FCC processing units 22. For example, the FCC process controller(s) 24 may be configured to generate one or more processing unit control signal(s) 30 indicative of parameters associated with operation of the FCC processing units 22, such as, for example, the rate of supply of the hydrocarbon feed/charge 18 the one or more FCC processing units 22; the pressure of the hydrocarbon feed/charge 18 supplied to the one or more FCC processing units 22; a preheating temperature of the hydrocarbon feed/charge 18 supplied to the one or more FCC processing units 22; the temperature in the FCC reactor 12 or one or more other FCC processing units 22; or a reactor pressure associated with a reaction mixture in the FCC reactor 12, wherein the reaction mixture may include the hydrocarbon feed/charge 18 and catalyst to promote catalytic cracking of the hydrocarbon feed/charge 18. For example, according to some embodiments, the assemblies and processes described herein may be used to produce propylene. In some such embodiments, the one or more process parameters may include, for example, residence time in the reactor, reaction temperature, catalyst-to-oil ratio, hydrocarbon partial pressure, and/or other process parameters associated with the production of propylene by an FCC processing assembly known to those skill in the art. Control of other parameters associated with operation of the FCC processing units 22 are contemplated. In some embodiments, controlling the one or more operating parameters of the one or more FCC processing units 22 may include controlling the one or more operating parameters against operating constraints associated with the one or more FCC processing units 22.

In some embodiments, a feedstock parameter associated with the hydrocarbon feed/charge 18 supplied to the one or more FCC processing units may include content, temperature, pressure, flow rate, API gravity, UOP K factor, distillation points, coker gas oil content, carbon residue content, nitrogen content, sulfur content, catalyst oil ratio, saturates content, thiophene content, single-ring aromatics content, dual-ring aromatics content, triple-ring aromatics content, and/or quad-ring aromatics content.

In some embodiments, one or more of the FCC process controller(s) 24 may be configured to prescriptively control at least a portion of the FCC process by, for example, operating an analytical cracking model, which may be executed by one or more computer processors. In some embodiments, the analytical cracking model may be configured to improve the accuracy of: predicting (or determining) one or more properties and/or one or more parameters associated with the hydrocarbon feed/charge 18 supplied to the one or more FCC processing units 22; predicting (or determining) one or more properties and/or one or more parameters associated with intermediate materials produced by the one or more FCC processing units 22; controlling the one or more properties and/or one or more parameters associated with the hydrocarbon feed/charge 18 supplied to the one or more FCC processing units 22; controlling the one or more properties and/or one or more parameters associated with the intermediate materials produced by the one or more FCC processing units 22; controlling one or more properties and/or one or more parameters associated with the FCC effluent produced by the one or more FCC processing units 22; the target properties of the unit product materials produced by the one or more FCC processing units 22; and/or the target properties of downstream materials produced by one or more of the downstream processing units, such as, for example, the fractionator 26 and/or processing units associated with operation of the fractionator 26.

In some embodiments, the analytical cracking model may include or be a machine-learning-trained model. In at least some such embodiments, the FCC process controller(s) 24 may be configured to: (a) provide, to the analytical cracking model, catalytic cracking processing data related to: (i) material data including one or more of: feedstock data indicative of one or more parameters and/or properties associated with the hydrocarbon feed/charge 18; unit material data indicative of one or more unit material properties associated with the one or more unit materials; and/or downstream material data indicative of one or more downstream material properties associated with one or more downstream materials produced by the one or more downstream processing units 36; and/or (ii) processing assembly data including: first processing unit data indicative of one or more operating parameters 32 associated with operation of the one or more processing units 34, such as, for example, the one or more FCC processing units 22; second processing unit data indicative of one or more operating parameters associated with operation of the one or more of the processing units 34 (collectively), such as, for example, the one or more downstream processing units 36; and/or conditioning assembly data indicative of operation of a sample conditioning assembly 28 configured to one or more of control a sample temperature of a material sample, remove particulates from the material sample, dilute the material sample in solvent, or degas the material sample; and/or (b) prescriptively controlling, based at least in part on the catalytic cracking processing data: one or more hydrocarbon feedstock parameters and/or properties associated with the hydrocarbon feed/charge 18; one or more first operating parameters associated with operation of the one or more FCC processing units 22; one or more properties associated with the one or more unit materials; content of the one or more unit materials; one or more second operating parameters associated with operation of the one or more downstream processing units 36 positioned downstream relative to the one or more FCC processing units 22; one or more properties associated with the one or more downstream materials produced by the one or more downstream processing units 36; content of the one or more downstream materials; and/or one or more sample conditioning assembly operating parameters associated with operation of the sample conditioning assembly 28. In some embodiments, the unit material properties and/or unit material parameters (e.g., intermediates and/or products of the FCC process and/or downstream processes) may include, for example, but are not limited to, amount of butane ($C_4$) free gasoline (volume), amount of total $C_4$ (volume), amount of dry gas (wt), amount of coke (wt), gasoline octane, amount of light fuel oil (LFO), amount of heavy fuel oil (HFO), amount of hydrogen sulfide ($H_2S$), amount of sulfur in the LFO, and/or the aniline point of the LFO. Other unit material properties and/or parameters are contemplated.

In some embodiments, the analytical cracking model may include one or more cracking algorithms. The cracking algorithms may be configured to determine, based at least in part on the catalytic cracking data, target material properties for one or more of the hydrocarbon feed/charge 18, the unit materials, or the downstream materials. In some embodiments, the cracking algorithms further may be configured to prescriptively control operation of one or more of the FCC processing units 22 and/or the one or more downstream processing units 36, for example, to produce one or more of unit materials having unit material properties within a first predetermined range of target unit material properties for the unit materials, or one or more of downstream materials having downstream material properties within a second predetermined range of target material properties for the downstream materials. Within range may include within a range above (but not below) the target unit material properties or the target material properties of the downstream materials, within a range below (but not above) the target unit material properties or the target material properties of the downstream materials, or within a range surrounding (on either or both sides of) the target unit material properties or the target material properties of the downstream materials. The cracking algorithms also may be configured to determine one or more of actual unit material properties for the unit materials produced by the one or more FCC processing units 24 or one or more of actual downstream material properties for the downstream materials produced by the one or more downstream processing units 36. The cracking algorithms, in some embodiments, further may be configured to determine one or more of unit material differences between the actual unit material properties and the target unit material properties or downstream material differences between the actual downstream material properties and the target downstream material properties. In some embodiments, the cracking algorithms further still may be configured to change, based at least in part on one or more of the unit material differences or the downstream material differences, the one or more cracking algorithms to reduce the one or more of the unit material differences or the downstream material differences. In some embodiments, the cracking algorithms may result in more responsively controlling the FCC processing assembly 10, the FCC processing unit(s) 22, and/or the downstream processing unit(s) 36 to achieve material outputs that more accurately and responsively converge on the target properties.

In some embodiments, the one or more FCC process controller(s) 24 may be configured to prescriptively control by one or more of (i) generating, based at least in part on the target unit material properties, one or more first processing unit control signals configured to control at least one first processing parameter associated with operation of the one or more FCC processing unit(s) 22 to produce one or more unit materials having unit material properties within the first preselected range of the target unit material properties; or (ii) generating, based at least in part on the target downstream material properties, a second processing unit control signal configured to control at least one second processing parameter associated with operation of the one or more downstream processing unit(s) 36 to produce one or more downstream materials having downstream material properties within the second preselected range of the target downstream material properties. In some embodiments, the FCC process controller(s) 24 still further may be configured to prescriptively control operation of the sample conditioning assembly 28, for example, by generating, based at least in part on the catalytic cracking data, a conditioning control signal configured to control at least one conditioning parameter related to operation of the sample conditioning assembly 28.

In some embodiments, the FCC process controller(s) 24 may be configured to predict the one or more hydrocarbon feed/charge 18 sample properties, for example, by mathematically manipulating a feedstock spectra signal indicative of the hydrocarbon feedstock sample spectra to provide a manipulated feedstock signal, and communicating the manipulated feedstock signal to an analytical property model configured to predict, based at least in part on the manipulated feedstock signal, the one or more hydrocarbon feedstock sample properties. In some examples, the FCC process controller(s) 24 may be configured to predict the one or more unit material sample properties by mathematically manipulating a unit material spectra signal indicative of the unit material sample spectra to provide a manipulated unit material signal, and communicating the manipulated unit material signal to an analytical property model configured to predict, based at least in part on the manipulated unit material signal, the one or more unit material sample properties. In some embodiments, the mathematical manipulation may be performed, for example, for an individual wavelength and/or a plurality of wavelengths over a range of wavelengths, and the mathematical manipulation may be based on, for example, a mathematical relationship, which may include one or more of a ratio, a correlation, an addition, a subtraction, a multiplication, a division, taking one or more derivatives, an equation, or a combination thereof, and/or other mathematically-derived relationships.

In some embodiments, the one or more FCC process controller(s) 24 may be configured to prescriptively control one or more aspects of the FCC process by, for example, generating, based at least in part on one or more of the hydrocarbon feed/charge 18 sample properties or one or more of the unit material sample properties, the one or more processing unit control signal(s) 30 to control on-line, during the FCC process, one or more of the processing parameter(s) 32 related to operation of one or more of the FCC processing unit(s) 22 and/or one or more of the downstream processing unit(s) 36. For example, in some embodiments, the one or more unit sample properties may include reaction effluent yield, and the prescriptive control may include controlling a riser outlet temperature based at least in part on the reaction effluent yield and/or riser lift velocity based at least in part on the reaction effluent yield. In some embodiments, the one or more unit material sample properties may include FCC product yield, and the prescriptive control may include, for example, controlling riser lift steam rate based at least in part on the FCC product yield. In some embodiments, the one or more unit material sample properties may include riser stripper effluent, and the prescriptive control may include, for example, controlling FCC catalyst stripping based at least in part on the riser stripper effluent.

In some embodiments, the one or more unit material sample properties may include one or more reaction effluent properties, and the FCC process controller(s) 24 may further be configured to on-line model, based at least in part on the one or more reaction effluent properties, operation of the one or more FCC processing unit(s) 22. In some embodiments, the one or more FCC process controller(s) 24 may be configured to prescriptively control, real-time for improvement or optimization of the FCC process. The FCC process controller(s) 24 may be configured, in at least some embodiments, to provide the one or more hydrocarbon feed/charge 18 sample properties and/or the one or more unit material sample properties to fluid catalytic cracking (FCC) simulation software, for example, to model FCC processing unit material yields and/or FCC unit material characteristics. For example, the one or more FCC process controller(s) 24 may be configured to determine, via the FCC simulation software, based at least in part on the one or more hydrocarbon feed/charge 18 sample properties and/or the one or more unit material sample properties, one or more processing unit control parameters to achieve the FCC processing unit material yields and/or the FCC unit material characteristics.

As shown in FIG. 1, the FCC reactor 12 may be configured to receive the hydrocarbon feed/charge 18 and a catalyst to promote catalytic cracking of the hydrocarbon feed/charge 18 into the FCC effluent 38, with the hydrocarbon feed/charge 18 and the catalyst providing a reaction mixture. In some such embodiments, the FCC control assembly 16 may include the one or more spectroscopic analyzers 20A through 20N, which may be configured to analyze reaction mixture samples taken from one or more locations of the FCC reactor 12 to obtain unit material samples of, for example, catalyst stripper vapor, reactor dilute vapor, riser vapor, and/or reactor effluent, for example, to determine respective catalyst stripper vapor yield, reactor dilute vapor yield, riser vapor yield, and/or reactor effluent yield.

In some embodiments, the unit sample properties may include one or more properties associated with reactor dilute vapors, and the FCC process controller(s) 24 may be configured to prescriptively control riser outlet conditions based at least in part on the reactor dilute vapors, and/or vapor quench based at least in part on the reactor dilute vapors. The one or more unit material properties may include one more unit material yields, and, in some embodiments, the FCC process controller(s) 24 may be configured to tune, based at least in part on the one or more unit material yields, a fluid catalytic cracking (FCC) simulation model, and/or benchmark, based at least in part on the one or more unit material yields, refinery linear program predicted yields.

As shown in FIG. 1, some embodiments of the FCC processing assembly 10 may include the FCC reactor 12, the catalyst regenerator 14, and the FCC control assembly 16 configured to enhance control of operation of at least some aspects of the FCC processing assembly 10 and related processes, such as the FCC process, as described herein. As shown in FIG. 1, the hydrocarbon feed/charge 18 may be supplied via a feed conduit 40, and a heater 42 may be provided and configured to preheat the feed/charge 18 prior to being supplied to the FCC reactor 12. The heater 42 may be any temperature control unit capable of heating the feed-charge 18 to a predetermined preheating temperature, such as, for example, a fossil-fuel-fired heater (e.g., a gas burner) and/or an electrically-powered heater. The heat flux supplied to the hydrocarbon feed/charge 18 may be controlled by, for example, the FCC process controller(s) 24, which may control a flow of fuel (e.g., via a control valve) and/or electrical power supplied to the heater 42. As shown in FIG. 1, in some embodiments, a sample of the hydrocarbon feed/charge 18 may be extracted upstream (before) the hydrocarbon feed/charge 18 is preheated, and the sample of the hydrocarbon feed/charge 18 may be supplied to the sample conditioning assembly 28 via a feed/charge sample conduit 44 for conditioning prior to be supplied to the one or more spectroscopic analyzer(s) 20A through 20N for analysis, for example, as described herein. In some embodiments, a fiber optic probe in communication with the one or more spectroscopic analyzer(s) 20A through 20N may be inserted directly into the feed conduit 40 to facilitate analysis of the hydrocarbon feed/charge 18 by one or more of the spectroscopic analyzer(s) 20A through 20N, which may prevent a need to extract the sample of the hydrocarbon feed/charge 18 for analysis via the feed/charge sample conduit 44. In some embodiments, water/steam 46 may be added to the preheated hydrocarbon feed/charge 18 via a water/steam conduit 48, for example, as shown in FIG. 1.

As shown in FIG. 1, some embodiments of the FCC processing assembly 10 may include a riser 50 for conveying the preheated hydrocarbon feed/charge 18 to the FCC reactor 12 and for combining catalyst 52, which may be received from the catalyst regenerator 14, with the hydrocarbon feed/charge 18 forming a reaction mixture 54, for example, to promote catalytic cracking of the hydrocarbon feed/charge 18 into the FCC effluent 38 in the FCC reactor 12. For example, the catalyst 52 may be supplied to a lower portion of the riser 50, for example, via a catalyst return line 56, as shown in FIG. 1. In some embodiments, the catalyst regenerator 14 may be configured to receive spent catalyst from the FCC reactor 12 via a catalyst stripper line 80 and at least partially recondition the spent catalyst, for example, by facilitating contact between the spent catalyst and air to burn-off carbon and produce flue gas that may exit the catalyst regenerator 14 via a regenerator cyclone 57 and a flue gas line 58. The reaction mixture 54 may be in the form of vaporized products, which ascend the riser 50 and may be recovered, for example, via a reactor cyclone 59 in the form of the FCC effluent 38. In some embodiments, the FCC processing unit(s) 22 may include a catalyst cooler 60, and the FCC process controller(s) 24 may be configured to control operation of the catalyst cooler 60.

As shown in FIG. 1, the FCC effluent 38 may be supplied to one or more downstream processing units 36, which may include, for example, the fractionator 26 and/or other associated downstream processing units 36. The fractionator 26 may be configured to separate various hydrocarbon products of the FCC effluent 38 received from the FCC reactor 12, such as, for example, hydrocarbon gases 60 (e.g., propane, butane, methane, and/or ethane), gasoline 62, light gas oil 64, and/or heavy gas oil 66. In some embodiments, at least a portion of the heavy gas oil 66 (e.g., naphtha) may be recycled and added to the hydrocarbon feed/charge 18 via a recycle line 67. In some embodiments, the FCC reactor 12 and/or the catalyst regenerator 14 may operate according to known FCC reactor and catalyst regenerator processes, except as described herein.

As shown in FIG. 1, the one or more spectroscopic analyzers 20A through 20B may be configured to receive material samples from one or more locations associated with the FCC processes and/or downstream processes. In some embodiments, the material samples, prior to being received by the one or more spectroscopic analyzers 20A through 20N for analysis, may be conditioned, for example, via the sample conditioning assembly 28, as described herein.

For example, the one or more spectroscopic analyzers 20A through 20N may be configured to receive (e.g., on-line and/or in a laboratory) a sample of the hydrocarbon feed/charge 18 to be supplied to the one or more FCC processing units 22 associated with the refining operation via the feed/charge sample conduit 44. The one or more spectroscopic analyzers 20A through 20N may be configured to analyze the sample of the hydrocarbon feed/charge 18 to provide hydrocarbon feedstock sample spectra.

In some embodiments, for example, as shown FIG. 1, the one or more spectroscopic analyzers 20A through 20N may be configured to receive on-line a sample of the one or more unit materials produced by the one or more FCC processing units 22. The one or more unit materials may include intermediate materials and/or unit product materials. The one or more spectroscopic analyzers 20A through 20N may be configured to analyze the samples of the unit materials to provide unit material sample spectra.

For example, as shown in FIG. 1, one or more of the spectroscopic analyzers 20A through 20N may be configured to receive on-line a sample of the FCC effluent 38 from the outlet of the FCC reactor 12, for example, via an effluent conduit 68, and the one or more spectroscopic analyzers 20A through 20N may be configured to analyze the FCC effluent 38 to generate one or more effluent sample spectra. In some embodiments, the one or more of the spectroscopic analyzers 20A through 20N may be configured to receive on-line a sample of the reaction mixture 54, for example, taken from one or more locations of the FCC reactor 12 and/or the riser 50 via a reaction mixture conduit 70, and analyze the reaction mixture 54 to generate one or more reaction mixture spectra. In some such embodiments, samples of the reaction mixture 54 may be taken from two or more locations of the FCC reactor 12 and/or riser 50, and respective samples of the reaction mixture 54 may be analyzed to generate two or more sets of reaction mixture spectra.

As shown in FIG. 1, one or more of the spectroscopic analyzers 20A through 20N may be configured to receive on-line two or more samples of the reaction mixture 54 taken from two or more respective different points along the height of the riser 50 via two or more riser sample conduits 72 (e.g., 72A, 72B, 72C, 72D, etc., as shown in FIG. 1), and respective samples of the reaction mixture 54 may be analyzed to generate two or more sets of reaction mixture spectra. In some embodiments, the one or more of the spectroscopic analyzers 20A through 20N may be configured to receive on-line a sample of the reaction mixture 54, for example, taken at the outlet of the riser 50 via a riser outlet conduit 74, and the sample of the reaction mixture 54 taken from the outlet of the riser 50 may be analyzed to generate reaction mixture outlet spectra.

In some embodiments, one or more of the spectroscopic analyzers 20A through 20N may be configured to analyze sample of the reaction mixture 54 taken at the outlet of the riser 50, and another one of the spectroscopic analyzers 20A through 20N may be configured to analyze the FCC effluent 38 taken at the outlet of the FCC reactor 12, the sample of the reaction mixture 54 and the sample of the FCC effluent 38 may be analyzed substantially concurrently. In some embodiments, one or more of the spectroscopic analyzers 20A through 20N may be configured to receive on-line two or more reaction mixture samples 54 taken from two or more respective different locations of the cross section of the riser 50 (e.g., form two or more respective different locations of the diameter), and the two or more samples of the reaction mixture 54 may be analyzed to generate two or more respective sets of reaction mixture spectra. In some embodiments, one or more of the spectroscopic analyzers 20A through 20N may be configured to receive on-line a sample of the reaction mixture 54 taken from the inlet of the riser 50 via a riser inlet conduit 76, and the sample taken from the inlet of the riser 50 may be analyzed to generate one or more riser inlet sample spectra.

As shown in FIG. 1, one or more of the spectroscopic analyzers 20A through 20N may be configured to receive on-line samples of the one or more downstream unit materials produced by one or more of the downstream processing units 36, such as the fractionator 26, and generate one or more downstream unit material sample spectra. For example, one or more of the spectroscopic analyzers 20A through 20N may be configured to receive on-line samples of one or more of a sample of the hydrocarbon gases 60 via a gas sample conduit 84, a sample of the gasoline 62 via a gasoline sample conduit 86, a sample of the light gas oil 64 via a light gas oil sample conduit 88, or a sample of the heavy gas oil 66 via a heavy gas oil sample conduit 90. The one or more spectroscopic analyzers 20A through 20N may be configured to analyze one or more of the downstream unit materials and generate one or more downstream material spectra indicative of one or more properties of the downstream unit materials, which may be used to predict (or determine) the one or more properties of the downstream unit materials.

As shown in FIG. 1, the analysis of the one or more spectroscopic analyzers 20A through 20N may be communicated to the one or more FCC process controller(s) 24. In some embodiments, the one or more FCC process controller(s) 24 may be configured to receive one or more signals indicative of the spectra associated with the feed/charge 18, the spectra associated with the reaction mixture 54, the spectra associated with the FCC effluent 38, and/or the spectra associated with unit materials produced by the one or more downstream processing units 36, compare one or more respective material properties associated therewith (e.g., hydrocarbon group type) against an optimum materials slate desired for improved or optimum efficiency. In some embodiments, such as comparison may be used to control supply of the hydrocarbon feed/charge 18 (e.g., flow rate, temperature, pressure, and/or content), and/or operation of one or more of the FCC processing units 22, operation of the sample conditioning assembly 28, and/or or operation of one or more of the downstream processing units (e.g., the fractionator 26). The FCC process controller(s) 24 may be configured to generate one or more processing unit control signal(s) 30, which may be communicated to one or more actuators (e.g., flow control valves and/or pumps), to one or more of the FCC processing units 22, and/or to one or more of the downstream processing units 36, to control one or more processing parameters 32 associated with the FCC process and/or associated processes. In some embodiments, the one or more processing control signal(s) 30 may be used to control the content, pressure, and/or temperature of the hydrocarbon feed/charge 18, and/or to control operation of the sample conditioning assembly 28, for example, as described herein.

As shown in FIG. 1, in some embodiments, the FCC processing assembly 10 may include a network 92 providing communication between components of the FCC processing assembly 10. The network 92 may be any type of communications network, such as, for example, a hard-wired may operate according to any known hard-wired communications protocols and/or wireless communications protocols, as will be understood by those skilled in the art.

In some embodiments, the FCC process controller(s) 24 may be configured to supply one or more hydrocarbon feedstock sample properties and/or one or more unit material sample properties to fluid catalytic cracking (FCC) simulation software to model FCC processing unit material yields and/or FCC unit material characteristics. In some examples, the FCC simulation software may be configured to determine, based at least in part on the one or more hydrocarbon feedstock sample properties and/or the one or more unit material sample properties, one or more processing unit control parameters to achieve the FCC processing unit material yields and/or the FCC unit material characteristics. In some embodiments, the FCC simulation software may be configured to determine one or more properties of the one or more downstream materials based at least in part on the one or more hydrocarbon feedstock properties and/or the one or more processing unit control parameters.

In some embodiments, the FCC simulation software may be configured to compare the one or more hydrocarbon feedstock properties to model hydrocarbon feedstock properties, and determine feedstock differences between the one or more hydrocarbon feedstock properties and the model hydrocarbon feedstock properties. Based at least in part on the feedstock differences, the FCC simulation software may be configured to determine the one or more processing unit control parameters to increase the efficiency of, improve, and/or optimize the FCC process.

Figure 2:
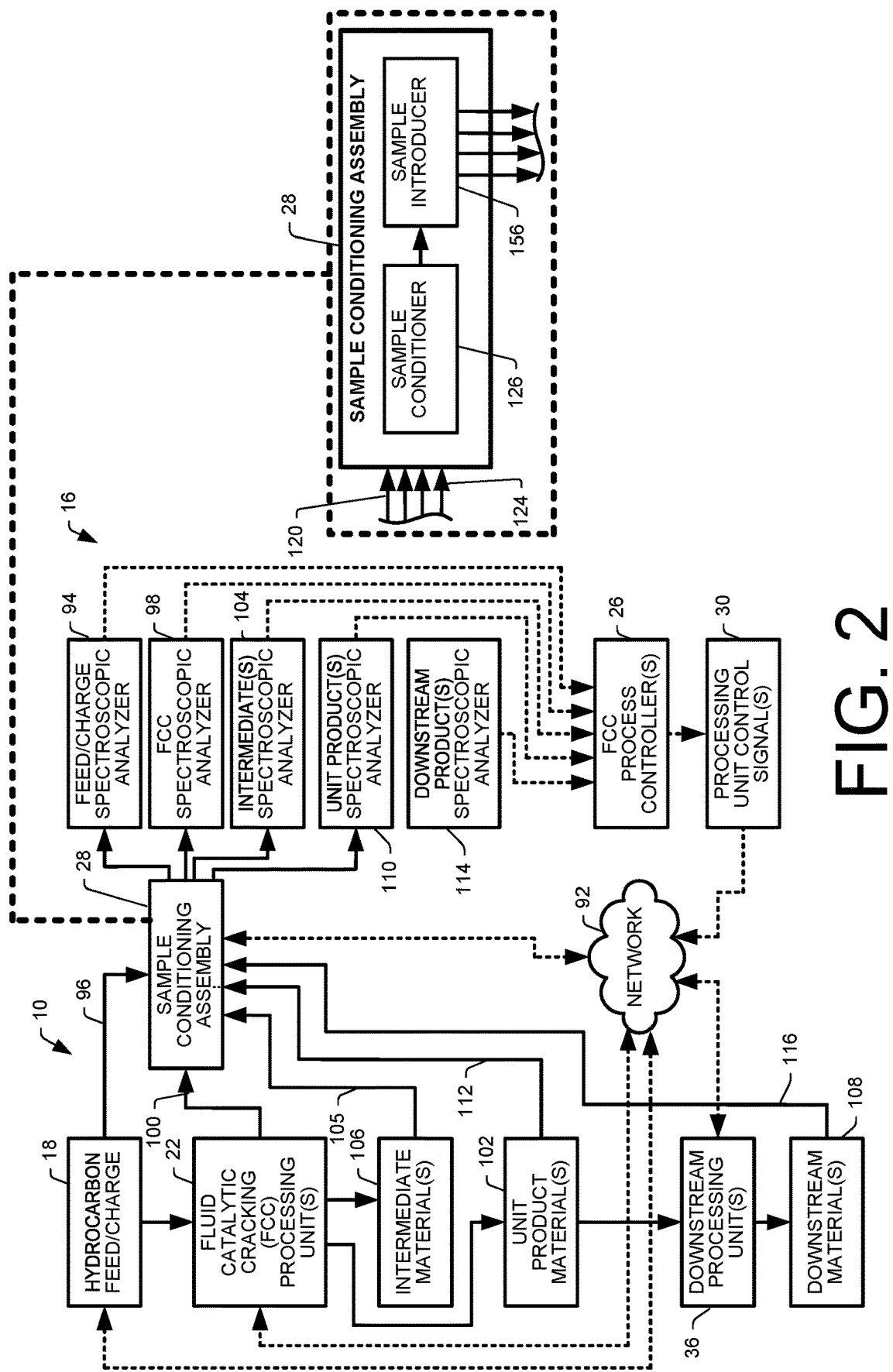
FIG. 2 is a schematic block diagram illustrating an example FCC processing assembly including an example FCC control assembly and an example sample conditioning assembly, according to embodiments of the disclosure.

FIG. 2 is a schematic block diagram illustrating an example FCC processing assembly 10 including an example FCC control assembly 16 and an example sample conditioning assembly 28, according to embodiments of the disclosure. As schematically shown in FIG. 2, the example FCC control assembly 16 may be used to at least partially (e.g., fully) control an FCC process performed by the FCC processing assembly 10. As shown in FIG. 2, in some embodiments, the FCC control assembly 16 may include a sample conditioning assembly 28 and one or more spectroscopic analyzers, such as, for example, a feed/charge spectroscopic analyzer 94 configured to receive (e.g., on-line and/or in a laboratory) via a feed sample conduit 96 a sample of the hydrocarbon feed/charge 18, an FCC spectroscopic analyzer 98 configured to receive on-line via an FCC sample conduit 100 a sample of one or more unit product materials 102 (e.g., samples of reaction mixture, and/or FCC effluent), an intermediates spectroscopic analyzer 104 configured to receive on-line via an intermediates sample conduit 105 a sample of one or more intermediate materials 106 (e.g., materials taken from points anywhere in the process between the hydrocarbon feed/charge 18 and downstream materials 108 produced by one or more downstream processing units 36), a unit products spectroscopic analyzer 110 configured to receive on-line via a unit products sample conduit 112 a sample of one or more unit product materials 102 produced by one or more of the FCC processing unit(s) 22, and/or a downstream products spectroscopic analyzer 114 configured to receive on-line via a downstream materials sample conduit 116 a sample of one or more of the downstream material(s) 108 produced by one or more of the downstream processing unit(s) 36. In some embodiments, one or more of the spectroscopic analyzers shown in FIG. 2 may substantially correspond to one or more of the spectroscopic analyzers 20A through 20N shown FIG. 1. In some embodiments, one or more of the spectroscopic analyzers shown in FIG. 2 may be configured to receive (e.g., on-line), analyze, and generate one or more spectra indicative of properties of the received samples.

As shown in FIG. 2, in some embodiments, the FCC processing assembly 10 also may include one or more FCC process controller(s) 24 in communication with one or more of the spectroscopic analyzers and control one or more aspects of the FCC process. For example, in some embodiments, the FCC process controller(s) 24 may be configured to predict one or more hydrocarbon feedstock sample properties associated with samples of the hydrocarbon feed/charge 18, for example, based at least in part on hydrocarbon feedstock sample spectra generated by the feed/charge spectroscopic analyzer 94. In some embodiments, the FCC process controller(s) 24 may be configured to predict (or determine) one or more unit material sample properties associated with the unit material samples based at least in part on the unit material sample spectra generated by the unit products spectroscopic analyzer 110. For example, as described herein, each of the one or more spectroscopic analyzer(s) shown in FIG. 2 may output a signal communicated to the one or more FCC process controller(s) 24, which may mathematically manipulate the signal (e.g., take a first or higher order derivative of the signal) received from the spectroscopic analyzer, and subject the manipulated signal to a defined model to generate material properties of interest, for example, as described herein. In some embodiments, such models may be derived from signals obtained from spectroscopic analyzer measurement of the one or more unit materials (e.g., the cracking products). In some examples, an analyzer controller in communication with a corresponding one or more of the spectroscopic analyzer(s) may be configured to receive the signal output by the one or more corresponding spectroscopic analyzers and mathematically manipulate the signal, for example, prior to the one or more FCC process controller(s) 24 receiving the signal.

In some embodiments, the FCC process controller(s) 24 may be configured to prescriptively control, based at least in part on the one or more hydrocarbon feedstock sample properties and the one or more unit material sample properties: (i) one or more feedstock parameters and/or properties associated with the hydrocarbon feed/charge 18 supplied to the one or more FCC processing units 22; (ii) content of the intermediate materials 106 produced by one or more of the FCC processing units 22; operation of the one or more FCC processing units 22; (iii) content of the one or more unit product materials 102; and/or operation of one or more downstream processing units 36 positioned downstream relative to the one or more FCC processing units 22, such as, for example, a fractionator 26 (see FIG. 1) configured to separate various hydrocarbon products of FCC effluent 38 received from the FCC reactor 12. In some embodiments, the prescriptive control may result in enhancing accuracy of target content of one or more of the intermediate materials 106, the unit product materials 102, or downstream materials 108 produced by the one or more downstream processing units 36 downstream from the one or more FCC processing units, thereby to more responsively control the FCC processing assembly 10 and/or the downstream processing unit(s) 36 to achieve material outputs that more accurately and responsively converge on target properties.

A shown in FIG. 2, the FCC processing assembly 10 further may include a sample conditioning assembly 28 configured to condition the hydrocarbon feed/charge 18, for example, prior to being supplied to the one or more spectroscopic analyzer(s). In some embodiments, the sample, conditioning assembly 28 may be configured to filter samples of the hydrocarbon feed/charge 18, change (e.g., control) the temperature of the samples of the hydrocarbon feed/charge 18, dilute the samples of the hydrocarbon feed/charge 18 in solvent (e.g., on-line and/or in a laboratory setting), and/or degas the samples of the hydrocarbon feed/charge 18. In some embodiments, the sample conditioning assembly 28 also may be configured to condition samples of one or more of the intermediate materials 106, the unit product materials 102, and/or the downstream materials 108, for example, prior to being supplied to the one or more spectroscopic analyzer(s), to filter the samples, to change (e.g., control) the temperature of the samples, dilute the samples in solvent, and/or to degas the samples. In some embodiments, the sample conditioning assembly 28 may result in more accurate, more repeatable, and/or more consistent analysis of the hydrocarbon feed/charge 18 and/or the one or more materials, which may in turn result in improved and/or more efficient control and/or more accurate control of the FCC process. and/or downstream processes. Example embodiments of a sample conditioning assembly 28 are described herein, for example, with respect to FIG. 3. In some embodiments, the one or more FCC process controller(s) 24 may be configured to control at least some aspects of operation of the sample conditioning assembly 28, for example, as described herein.

As shown in FIG. 2, in some embodiments, the one or more FCC process controller(s) 24 may be configured to prescriptively control one or more process parameters associated with operation of one or more of the FCC processing units 22. For example, the FCC process controller(s) 24 may be configured to generate one or more processing unit control signal(s) 30 indicative of parameters associated with operation of the FCC processing units 22, such as, for example, content of the hydrocarbon feed/charge 18, the rate of supply of the hydrocarbon feed/charge 18 the one or more FCC processing unit(s) 22; the pressure of the hydrocarbon feed/charge 18 supplied to the one or more FCC processing unit(s) 22; a preheating temperature of the hydrocarbon feed/charge 18 supplied to the one or more FCC processing unit(s) 22; the temperature in the FCC reactor 12 or one or more other FCC processing unit(s) 22; or a reactor pressure associated with a reaction mixture in the FCC reactor 12, wherein the reaction mixture may include the hydrocarbon feed/charge 18 and catalyst to promote catalytic cracking of the hydrocarbon feed/charge 18. Control of other parameters associated with operation of the FCC processing units 22 are contemplated.

In some embodiments, a feedstock parameter associated with the hydrocarbon feed/charge 18 supplied to the one or more FCC processing units may include content, temperature, pressure, flow rate, API gravity, UOP K factor, distillation points, coker gas oil content, carbon residue content, nitrogen content, sulfur content, catalyst oil ratio, saturates content, thiophene content, single-ring aromatics content, dual-ring aromatics content, triple-ring aromatics content, and/or quad-ring aromatics content.

In some embodiments, one or more of the FCC process controllers 24 may be configured to prescriptively control at least a portion of the FCC process by, for example, operating an analytical cracking model, which may be executed by one or more computer processors. In some embodiments, the analytical cracking model may be configured to improve the accuracy of: predicting one or more parameters and/or properties associated with the hydrocarbon feed/charge 18 supplied to the one or more FCC processing unit(s) 22; predicting one or more parameters and/or properties associated with intermediate materials produced by the one or more FCC processing unit(s) 22; controlling one or more parameters and/or properties associated with the hydrocarbon feed/charge 18 supplied to the one or more FCC processing unit(s) 22; controlling one or more parameters and/or properties associated with the intermediate materials produced by the one or more FCC processing unit(s) 22; controlling one or more parameters and/or properties associated with the FCC effluent produced by the one or more FCC processing unit(s) 22; the target content of the unit product materials produced by the one or more FCC processing unit(s) 22; and/or the target content of downstream materials produced by one or more of the downstream processing unit(s) 36, such as, for example, the fractionator 26 and/or processing units associated with operation of the fractionator 26.

As shown in FIG. 2, in some embodiments, the FCC processing assembly 10 may include a network 92 providing communication between components of the FCC processing assembly 10. The network 92 may be any type of communications network, such as, for example, a hard-wired may operate according to any known hard-wired and/or wireless communications protocols, as will be understood by those skilled in the art.

Figure 3:
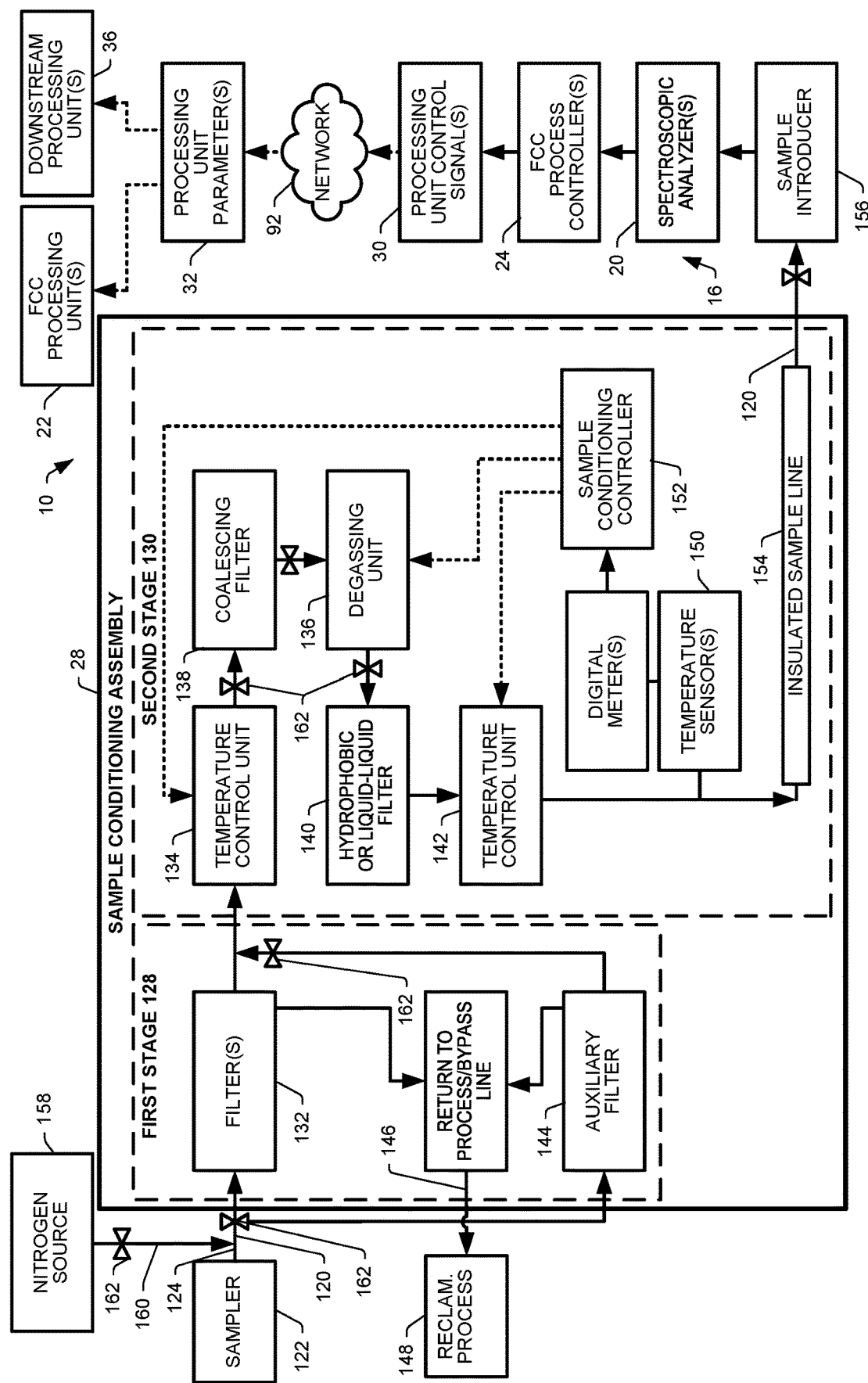
FIG. 3 is a schematic block diagram illustrating an example sample conditioning assembly, according to embodiments of the disclosure.

FIG. 3 is a schematic block diagram illustrating an example sample conditioning assembly 28, according to embodiments of the disclosure. In some embodiments, the sample conditioning assembly 28 may be configured to condition a sample (e.g., an at least partially continuous sample stream) of one or more materials associated with an FCC process and/or one more processes upstream and/or downstream relative to the FCC process, for example, to enhance analysis of the sample by one or more spectroscopic analyzer(s) 20 (e.g., one or more of the spectroscopic analyzer(s) 20A through 20N shown in FIG. 1) associated with the process or processes. As described herein, in some embodiments, operation of one or more components of the sample conditioning assembly 28 may be at least partially controlled (e.g., prescriptively controlled) via the one or more FCC process controller(s) 24, which may further enhance the analysis of the sample(s) by one or more spectroscopic analyzer(s) 20.

As shown in FIG. 3, in some embodiments, the sample conditioning assembly 28 may include a sampling circuit 120 positioned to direct samples (e.g., an on-line sample stream) from any point taken along the FCC process, an upstream process, and/or a downstream process, to provide the samples for analysis. In some embodiments, the sampling circuit 120 may include a sampler 122 including one or more of a sample probe, a sample supply pump, or a pressure adjuster to control a supply of the sample from a header 124 configured to provide a flow of the sample. The sample conditioning assembly 28 further may include a sample conditioner 126 in fluid association with the sampling circuit 120 and positioned to receive the sample via the sampling circuit 120. The sample conditioner 126 may be configured to condition the sample for analysis by the one or more spectroscopic analyzer(s) 20.

As shown in FIG. 3, in some embodiments, the sample conditioner 126 may include a first stage 128 and a second stage 130. For example, the first stage 128 of the sample conditioner 126 may include a first set of one or more filters 132 including filter media positioned to remove one or more of water, particulates, or other contaminants from the sample to provide a filtered sample (e.g., a filtered sample stream). In some embodiments including the second stage 130, the second stage 130 may include, for example, a first temperature control unit 134 in fluid communication with the first set of the one or more filters 132 and configured to receive the filtered sample and to change (e.g., control) the temperature of the filtered sample of the to provide a temperature-adjusted sample (e.g., a temperature-adjusted sample stream), such that the temperature of the temperature-adjusted sample is within a first preselected temperature range. For example, the first temperature control unit 134 may include a cooler or heat exchanger configured to reduce the temperature of the filtered sample. In some embodiments, the first preselected temperature range may be from about 45 degrees F. to about 50 degrees F., although other temperature ranges are contemplated.

In some embodiments, as shown in FG. 3, the second stage 130 also may include a degassing unit 136 configured to degas the temperature-adjusted sample to provide a degassed sample (e.g., a degassed sample stream). As shown in FIG. 3, some embodiments may include a second set of one or more filters 138 (e.g., one or more coalescing filters) in fluid communication with the first temperature control unit 134 and configured to remove one or more of water, particulates, or other contaminants from the degassed sample. In some embodiments, the second stage 130 further may include a third set of one or more filters 140 (e.g., one or more hydrophobic and/or liquid-to-liquid filters) configured to further filter the sample. The second stage 130 further may include a second temperature control unit 142 in fluid communication with one or more of the degassing unit 136 or the second set of the one or more filters 138 and configured to change (e.g., control) the temperature of the degassed sample to provide a temperature-adjusted degassed sample (e.g., a temperature-adjusted degassed sample stream), such that the temperature-adjusted degassed sample has a temperature within a second preselected temperature range to feed to the one or more spectroscopic analyzers for more accurate, more consistent, and/or more repeatable analysis (e.g., for more accurate property measurements). In some embodiments, the second temperature control unit 142 may include a heater or heat exchanger configured to increase the temperature of the degassed sample. In some embodiments, the second preselected temperature range may be from about 70 degrees F. to about 75 degrees F., although other temperature ranges are contemplated.

As shown in FIG. 3, some embodiments of the sample conditioning assembly 28 may include an auxiliary filter 144 in fluid communication with the sampling circuit 120 and connected in parallel relative to the first set of the one or more filters 132. The auxiliary filter 144 may be configured to receive the sample and remove one or more of water, particulates, or other contaminants from the sample, for example, to output a filtered sample when the first set of the one or more filters 132 are not in use, for example, during maintenance or service. In some embodiments, the sample conditioning assembly 28 may include a bypass conduit 146 configured to facilitate passage of one or more of water, particulates, or contaminates removed from the sample to one or more of, for example, a process, a sample recovery assembly, or a pump, for example, as depicted in FIG. 3 as a reclamation process 148.

As shown in FIG. 3, the sample conditioning assembly 28 may include one or more temperature sensors 150 associated with the sample conditioning assembly 28 and configured to generate one or more temperature signals indicative of the temperature of one or more of the filtered sample, the temperature-adjusted sample, the degassed sample, or the temperature-adjusted degassed sample. The sample conditioning assembly 28 further may include a sample conditioning controller 152 in communication with the one or more temperature sensors 150 and configured to receive the one or more temperature signals and communicate the one or more temperature signals to the FCC process controller(s) 24, which may use the one or more temperature signals to control an aspect of the FCC process and/or operation of the first temperature control unit 134 and/or the second temperature control unit 142.

As shown in FIG. 3, some embodiments may include an insulated sample line 154 in flow communication with, for example, the second temperature control unit 142. Some such embodiments further may include a sample introducer 156 in flow communication with the second temperature control unit 142 via the insulated sample line 154, and the sample introducer 156 may be configured to provide fluid flow from the second temperature control unit 142 to the one or more spectroscopic analyzer(s) 20 to supply the temperature-adjusted degassed sample to the one or more spectroscopic analyzer(s) 20, for example, after at least partially conditioning the sample. Some embodiments further may include an optical fiber cable connected to the second temperature control unit 142 and the sample introducer 156, and the optical fiber cable may be configured to substantially maintain the temperature of the temperature-adjusted degassed sample within the second preselected temperature range, for example, until the sample reaches the one or more spectroscopic analyzer(s) 20.

As shown in FIG. 3, some embodiments of the sample conditioning assembly 28 may include a nitrogen source 158 in selective fluid communication via a nitrogen conduit 160 with the first stage 128 of the sample conditioning assembly 28. The nitrogen source 158 may be used to flush portions of the sample conditioning assembly 28, for example, between receipt of different samples, to improve the accuracy of analysis of the sample by the one or more spectroscopic analyzer(s) 20. In some embodiments, the nitrogen source 158 may be used to flush particulates, fluid, and/or contaminates from the sample conditioning assembly 28.

As shown in FIG. 3, the sample conditioning assembly 28 may include one or more flow control devices 162, such as valves configured to control the flow of samples to, within, and/or at exit of the sample conditioning assembly 28. In some embodiments, the flow control devices 162 may include one or more pumps, one or more flow regulators, etc., configured to control the flow of samples to, within, and/or at exit of the sample conditioning assembly 28. In some embodiments, one or more actuators (e.g., electrical, hydraulic, and/or pneumatic actuators) may be connected to one or more of the flow control devices 162, and operation of the one or more actuators may be controlled via the sample conditioning controller 152 and/or one or more of the FCC process controller(s) 24 to control flow of the samples to, within, and/or at exit of the sample conditioning assembly 28.

Figure 4A:
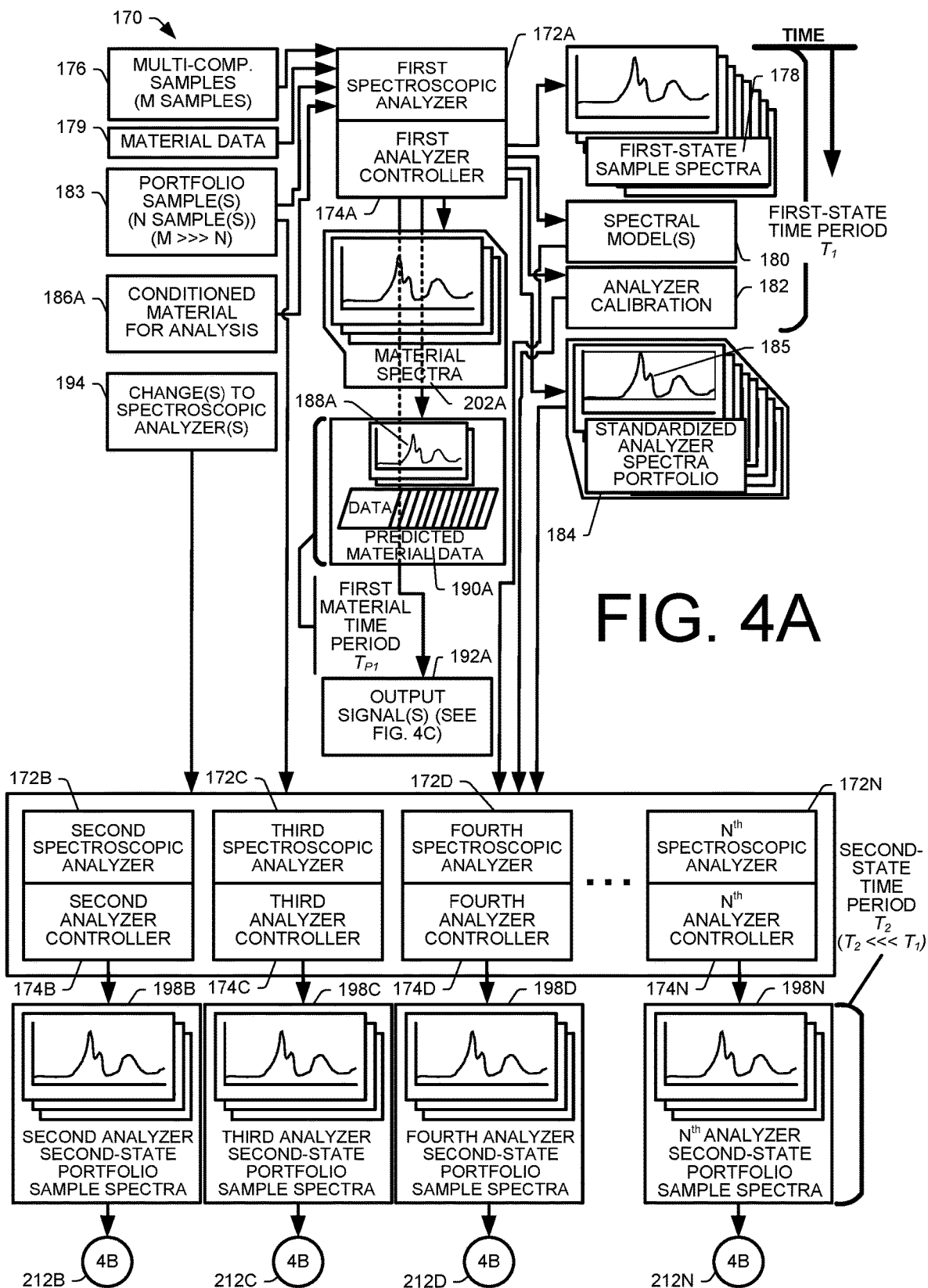
FIG. 4A is a block diagram of a spectroscopic analyzer assembly including a first standardized spectroscopic analyzer and a first analyzer controller configured to standardize a plurality of spectroscopic analyzers and showing example inputs and example outputs in relation to an example timeline, according to embodiments of the disclosure.
Figure 4B:
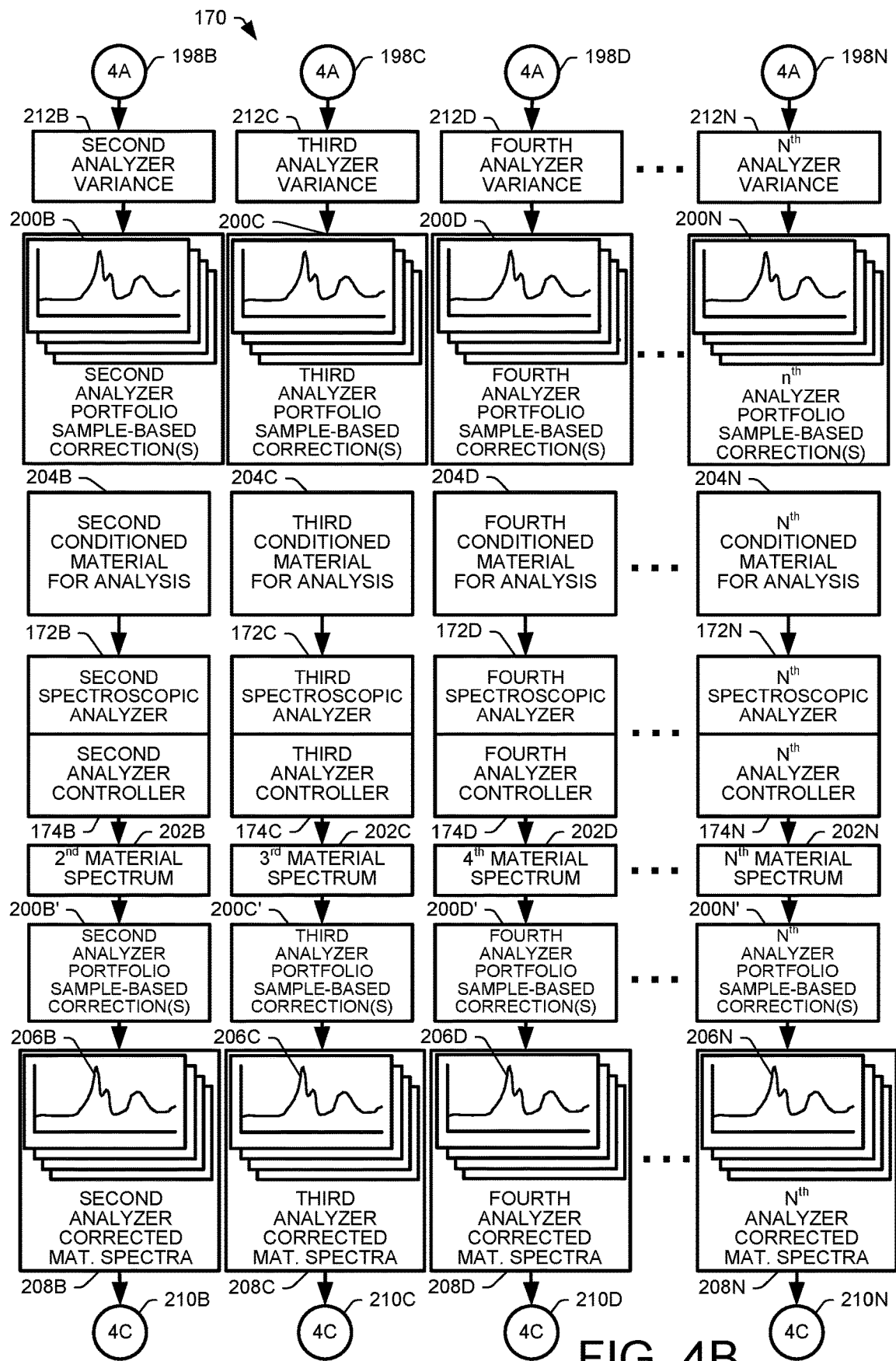
FIG. 4B is a continuation of the block diagram shown in FIG. 4A showing the plurality of example standardized spectroscopic analyzers outputting respective analyzer portfolio sample-based corrections based at least in part on respective variances, and analyzing conditioned materials for outputting respective corrected material spectra, according to embodiments of the disclosure.
Figure 4C:
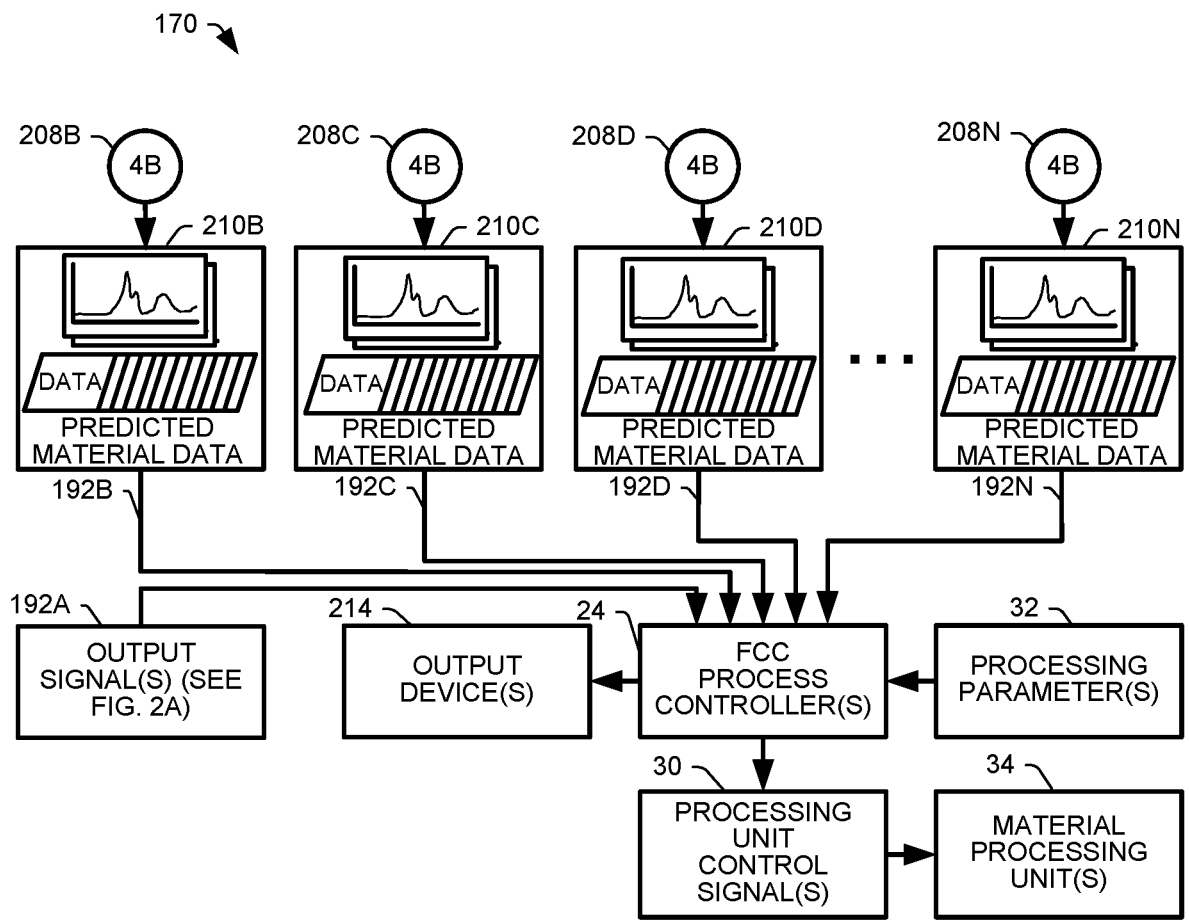
FIG. 4C is a continuation of the block diagrams shown in FIGS. 4A and 4B showing respective corrected material spectra output by the plurality of standardized spectroscopic analyzers used to output predicted (or determined) material data for the materials for use in an example FCC process, according to embodiments of the disclosure.
Figure 5A:
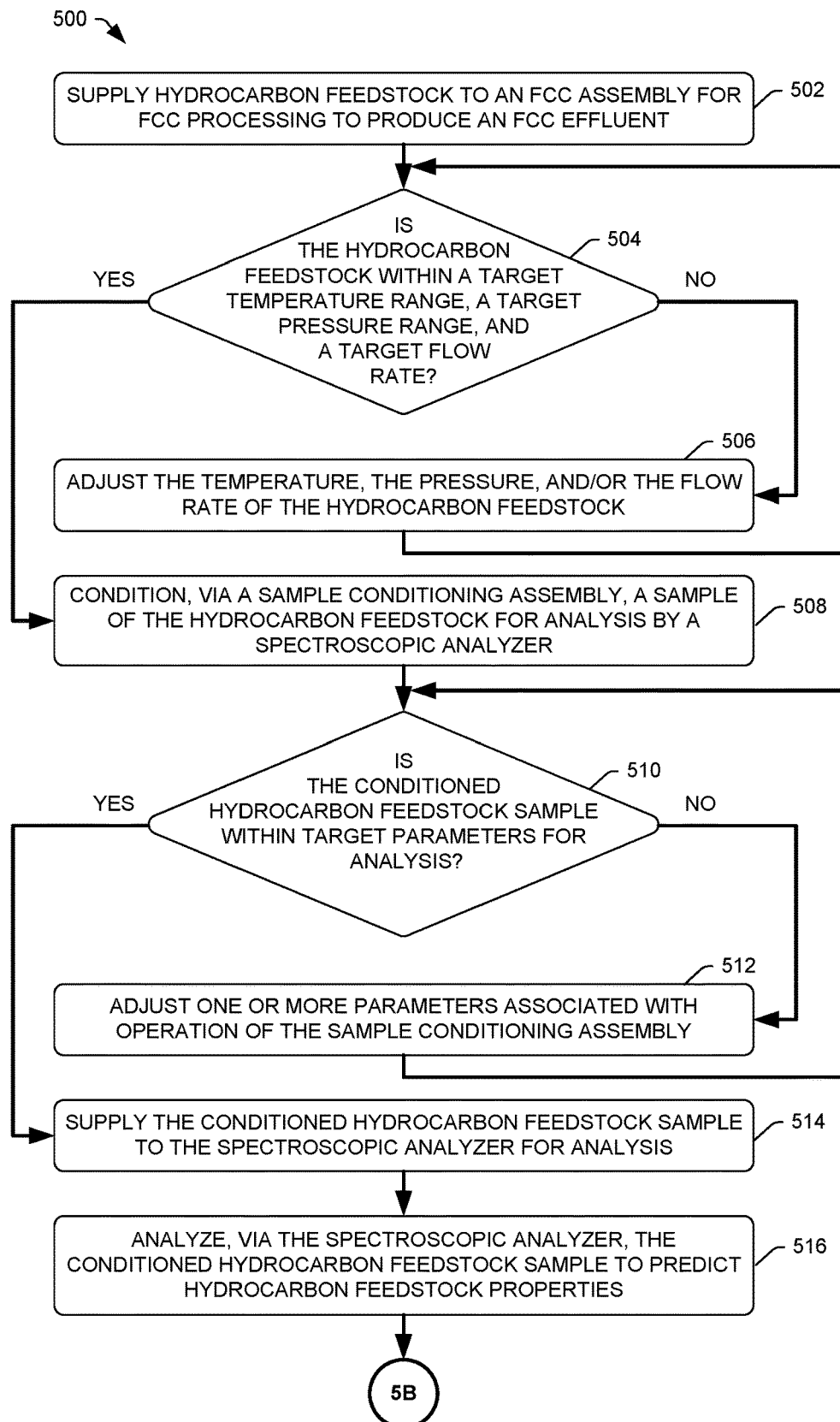
FIG. 5A is a block diagram of an example method to enhance a fluid catalytic cracking (FCC) process associated with a refining operation, during the FCC process, according to embodiments of the disclosure.
Figure 5B:
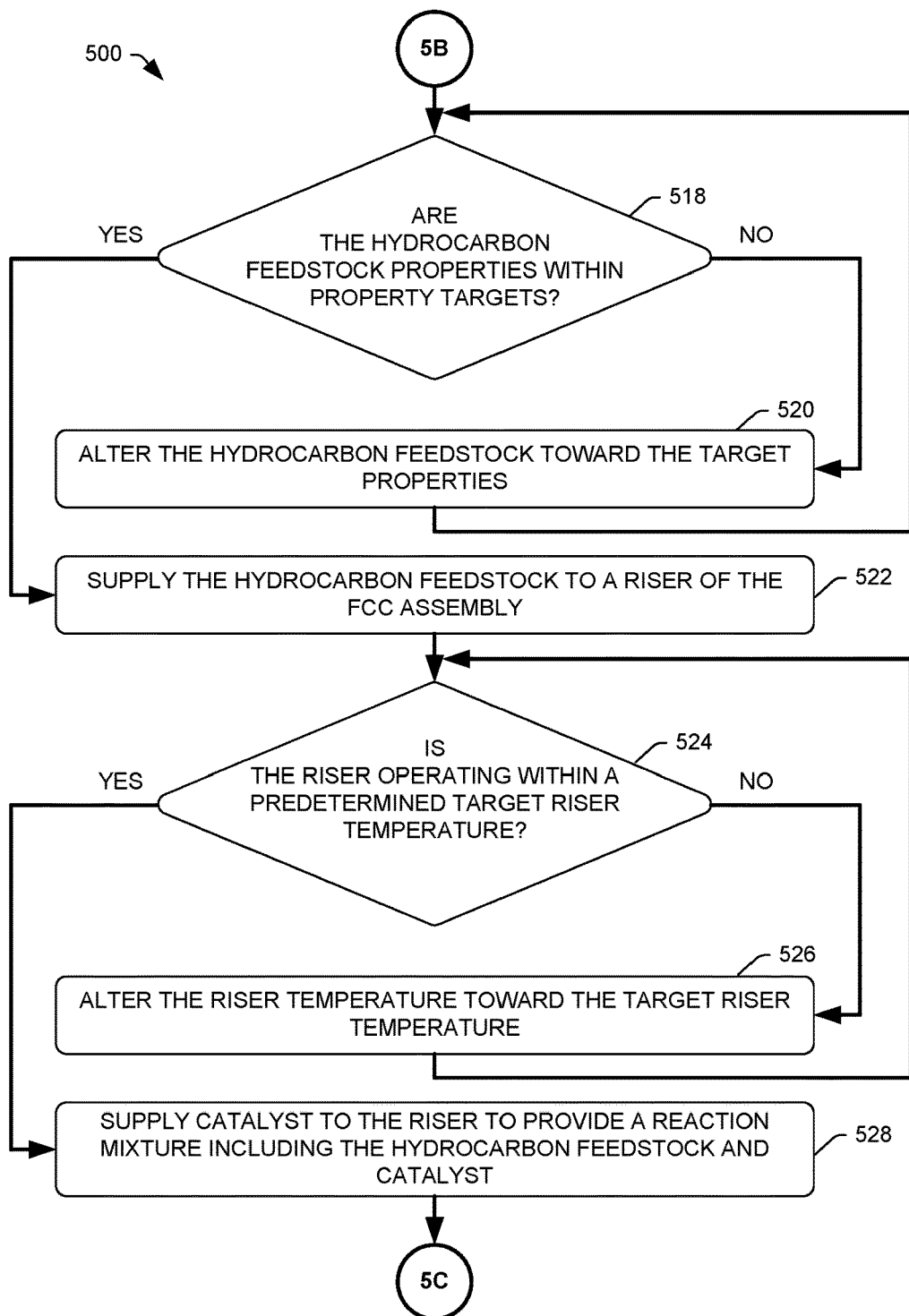
FIG. 5B is a continuation of the block diagram shown in FIG. 5A, according to embodiments of the disclosure.
Figure 5C:
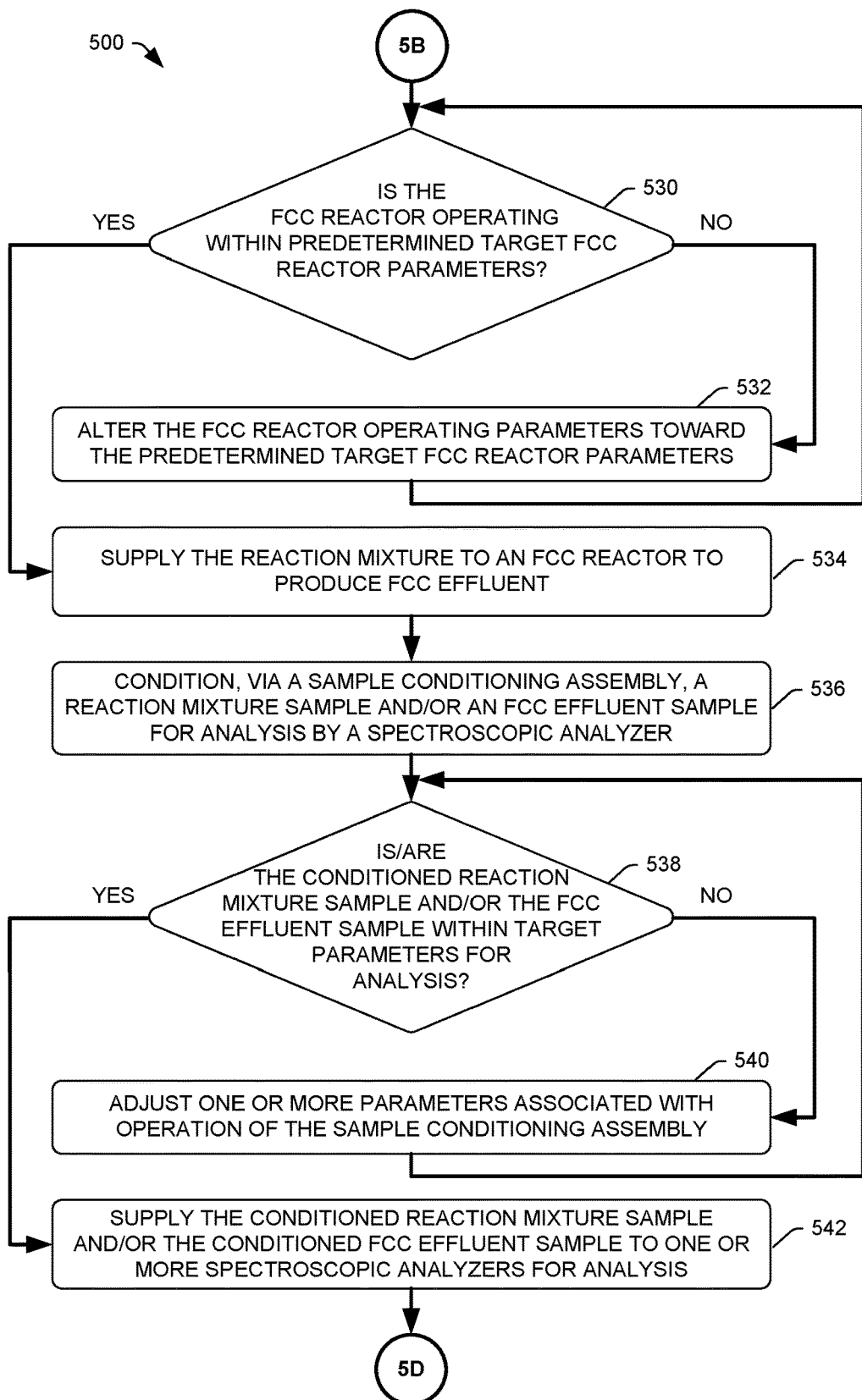
FIG. 5C is a continuation of the block diagram shown in FIG. 5A and FIG. 5B, according to embodiments of the disclosure.
Figure 5D:
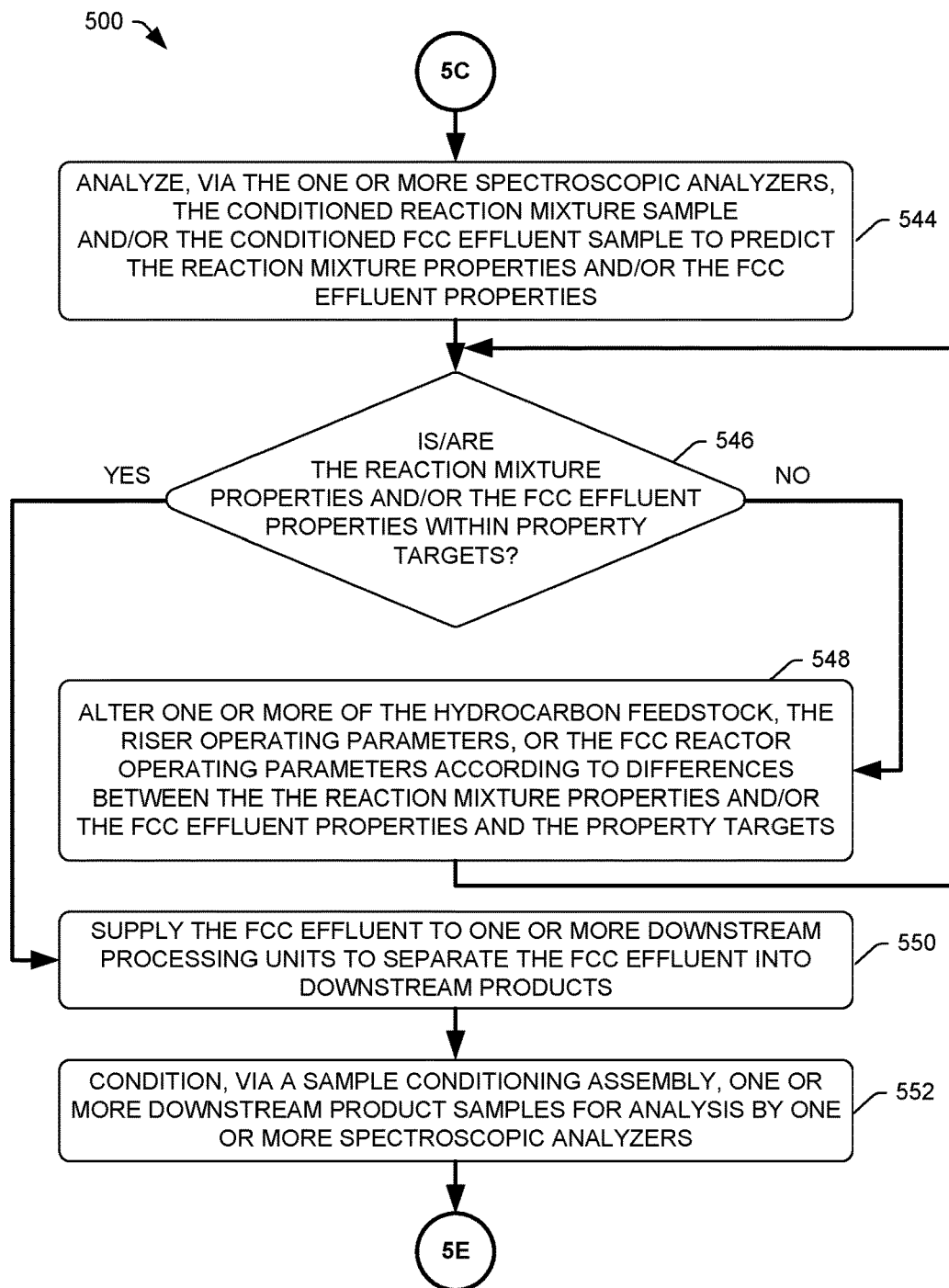
FIG. 5D is a continuation of the block diagram shown in FIG. 5A, FIG. 5B, and FIG. 5C, according to embodiments of the disclosure.
Figure 5E:
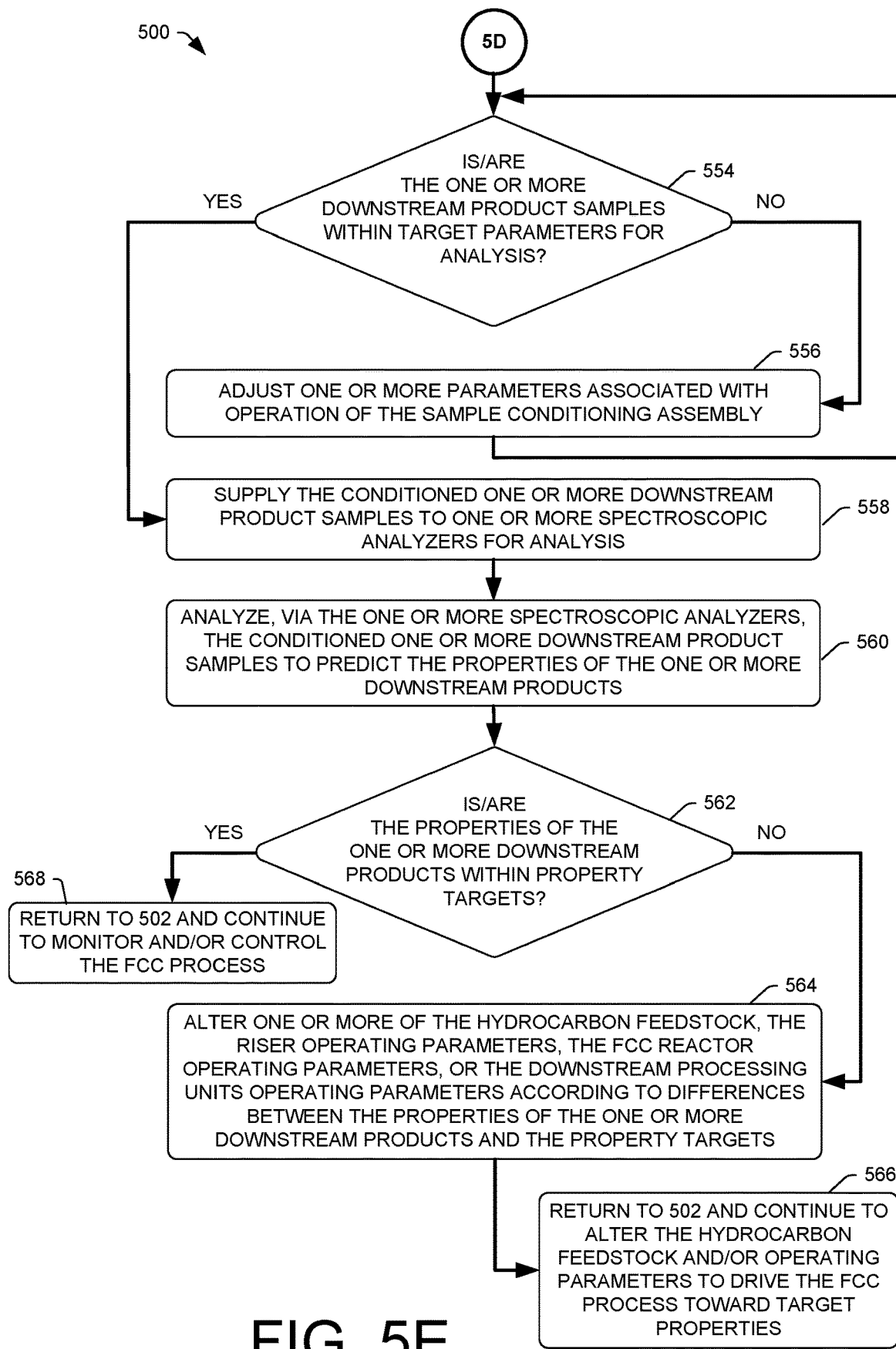
FIG. 5E is a continuation of the block diagram shown in FIG. 5A, FIG. 5B, FIG. 5C, and FIG. 5D, according to embodiments of the disclosure.

FIG. 4A. FIG. 4B, and FIG. 4C are a block diagram of a spectroscopic analyzer assembly 170 including a first standardized spectroscopic analyzer 172A and a first analyzer controller 174A configured to standardize a plurality of spectroscopic analyzers and showing example inputs and example outputs in relation to an example timeline, according to embodiments of the disclosure. FIG. 4B shows the plurality of example standardized spectroscopic analyzers 172A through 172N (collectively 172) and/or the analyzer controllers 174A through 174N (collectively 174) analyzing conditioned materials to output predicted (or determined) material data for the materials for use in example processes, such as the FCC process and related processes described herein, according to embodiments of the disclosure. According to some embodiments, the spectroscopic analyzers 172A through 172N and the analyzer controllers 174A through 174N shown in FIGS. 4A through 4C may substantially correspond the spectroscopic analyzer(s) 20A through 20N shown in FIG. 1 and/or the spectroscopic analyzers(s) shown in FIG. 2. In some embodiments, the spectroscopic analyzers 172 and/or the analyzer controllers 174 may analyze unconditioned material samples, semi-conditioned material samples, and/or conditioned material samples to output predicted (or determined) material data for the material samples for use in example processes, such as the processes described herein.

FIG. 4B is a continuation of the block diagram shown in FIG. 4A showing the plurality of example standardized spectroscopic analyzers 172 outputting respective analyzer portfolio sample-based corrections based at least in part on respective variances, and analyzing conditioned materials for outputting respective corrected material spectra, according to embodiments of the disclosure. FIG. 4C is a continuation of the block diagrams shown in FIGS. 4A and 4B showing respective corrected material spectra output by the plurality of standardized spectroscopic analyzers 172 used to output predicted (or determined) material data for the materials for use in an example FCC process, according to embodiments of the disclosure.

Spectroscopic analyzers may be used to non-destructively predict (or determine) properties associated with materials. For example, a sample of material may be fed to a spectroscopic analyzer for analysis, and a beam of electromagnetic radiation may be transmitted into the material sample, resulting in the spectroscopic analyzer measuring a spectral response representative of the chemical composition of the sample material, which may be used to predict (or determine) properties of the sample material via the use of modeling. The spectral response may include a spectrum related to the absorbance, transmission, transflectance, reflectance, or scattering intensity caused by the material sample over a range of wavelengths, wavenumbers, or frequencies of the electromagnetic radiation.

Applicant has recognized that over time the results of analysis using a spectroscopic analyzer may change, for example, due to changes or degradation of the components of the spectroscopic analyzer, such as its lamp, laser, detector, or grating. Changing or servicing components of the spectroscopic analyzer may alter its spectral responses relative to the spectral responses outputted prior to the changes, necessitating recalibration. Further, for some applications (e.g., as described herein), more than one spectroscopic analyzer may be used in association with analysis of materials at, for example, a production facility (e.g., a refinery), and it may be desirable for two or more of the spectroscopic analyzers to generate results that are reproducible and consistent with one another to enhance control of the production process, such as an FCC process and/or related upstream processes and/or downstream processes. Due to the complex nature, sensitivity, and principle of operation of spectroscopic analyzers, however, two spectroscopic analyzers may not be likely to provide equivalent results within the variability of the primary test method with which calibration models were made without additional activity (e.g., extensive testing), even when analyzing the same sample of material. This may result in a lack of reproducibility or consistency of results across different spectroscopic analyzers, potentially rendering comparisons between the results outputted by two or more spectroscopic analyzers of little value, unless the spectroscopic analyzers have been calibrated to achieve the same spectral responses.

In some embodiments, methods and assemblies described herein may be used for determining and using standardized spectral responses for calibration (or recalibration) of spectroscopic analyzers. For example, in some embodiments, the methods and assemblies may be used to calibrate or recalibrate a spectroscopic analyzer when the spectroscopic analyzer changes from a first state to a second state, for example, the second state being defined as a period of time after a change to the spectroscopic analyzer causing a need to calibrate the spectroscopic analyzer. In some embodiments, the recalibration may result in the spectroscopic analyzer outputting a standardized spectrum, for example, such that the spectroscopic analyzer outputs a corrected material spectrum for an analyzed material, including one or more of an absorption-corrected spectrum, a transmittance-corrected spectrum, a transflectance-corrected spectrum, a reflectance-corrected spectrum, or an intensity-corrected spectrum and defining the standardized spectrum. In some embodiments, the corrected material spectrum, output when the calibrated or recalibrated spectroscopic analyzer is in the second state, may include a plurality of signals indicative of a plurality of material properties of an analyzed material (e.g., a sample of the material) based at least in part on the corrected material spectrum, the plurality of material properties of the material being substantially consistent with a plurality of material properties of the material outputted by the spectroscopic analyzer in the first state. This may enhance the accuracy, reproducibility, and/or consistency of results outputted by the second-state recalibrated spectroscopic analyzer prior to recalibration relative to results outputted by the first-state spectroscopic analyzer.

In some embodiments, using calibration of a first spectroscopic analyzer to calibrate one or more additional spectroscopic analyzers may include using standardized analyzer spectra for calibration of a spectroscopic analyzer, for example, such that each of the one or more spectroscopic analyzers outputs a corrected material spectrum, including a plurality of signals indicative of a plurality of material properties of an analyzed material based at least in part on the corrected material spectrum, such that the plurality of material properties of the material are substantially consistent with a plurality of material properties of the material outputted by the first spectroscopic analyzer. In some embodiments, this may result in achieving desired levels of accuracy, reproducibility, and/or consistent results from a plurality of spectroscopic analyzers, potentially rendering comparisons between the results outputted by two or more of the spectroscopic analyzers more valuable, for example, when incorporated into a complex process including a plurality of different material altering processes, such as, for example, an FCC process and/or related upstream processes and/or downstream processes.

According to some embodiments, a method for determining and using standardized analyzer spectral responses to enhance a process for calibration of a plurality of spectroscopic analyzers, such that for a given material each of the plurality of spectroscopic analyzers outputs a plurality of signals indicative of a plurality of material properties of the material, the plurality of material properties of the material output by each of the plurality of spectroscopic analyzers being substantially consistent with one another, may include transferring one or more spectral models to each of the plurality of spectroscopic analyzers. Each of the one or more spectral models may be indicative of relationships between a spectrum or spectra and one or more of the plurality of material properties of one or more materials. The method also may include analyzing, via the first spectroscopic analyzer when in a first state, a selected one or more first-state portfolio samples to output a standardized analyzer spectra portfolio for the selected one or more first-state portfolio samples. The standardized analyzer spectra portfolio may include a first-state portfolio sample spectrum for each of the first-state portfolio samples. The method further may include analyzing, via each of a remainder of the plurality of spectroscopic analyzers when in a second state a selected one or more second-state portfolio samples to output second-state portfolio sample spectra for the selected one or more second-state portfolio samples. Each of the second-state portfolio sample spectra may be associated with a corresponding second-state portfolio sample. The analysis of the selected one or more second-state portfolio samples may occur during a second-state time period. The multi-component samples may include a significantly greater number of samples than a number of samples included in the second-state portfolio samples, and the second-state time period for analyzing the second-state portfolio samples may be significantly less than the first-state time period. The method also may include comparing one or more of the second-state portfolio sample spectra for the selected plurality of portfolio samples to the first-state sample spectra of a selected plurality of corresponding first-state multi-component samples. The method still further may include determining, based at least in part on the comparison, for the one or more of the selected plurality of portfolio samples of the second-state portfolio sample spectra, a variance at one or more of a plurality of wavelengths or over a range of wavelengths between the second-state portfolio sample spectra output by each of the remainder of the plurality of spectroscopic analyzers when in the second state and the first-state sample spectra corresponding to the selected one or more first-state multi-component material samples output by the first spectroscopic analyzer in the first state.

In some embodiments, the method still further may include analyzing, via one or more of the remainder of the plurality of spectroscopic analyzers when in the second state, a material received from a material source to output a material spectrum. The method also may include transforming, based at least in part on the standardized analyzer spectra portfolio, the material spectrum to output a corrected material spectrum for the material when in the second state, the corrected material spectrum including one or more of an absorption-corrected spectrum, transmittance-corrected spectrum, a transflectance-corrected spectrum, a reflectance-corrected spectrum, or an intensity-corrected spectrum and defining a standardized spectrum, for example, and/or a mathematical treatment of the material spectrum, such as, for example, a second derivative of the material spectrum.

In the example embodiments shown in FIGS. 4A, 4B, and 4C, the spectroscopic analyzer assembly 170 may include a first spectroscopic analyzer 172A and a first analyzer controller 174A configured to determine and use standardized analyzer spectral responses to standardize spectral responses of one or more (e.g., each) of the plurality of spectroscopic analyzers (e.g., a second spectroscopic analyzer 172B, a third spectroscopic analyzer 172C, and a fourth spectroscopic analyzer 172D through an $N^{th}$ spectroscopic analyzer 172N), such that for a given material one or more of the plurality of spectroscopic analyzers outputs a plurality of signals indicative of a plurality of material properties of the material, the plurality of material properties of the material output by each of the plurality of spectroscopic analyzers being substantially consistent with one another. In some embodiments, the spectroscopic analyzer assembly 170 may further include a plurality of analyzer controllers (e.g., a second analyzer controller 174B, a third analyzer controller 174C, and a fourth analyzer controller 174D through an $N^{th}$ analyzer controller 174N), each associated with a corresponding spectroscopic analyzer.

In some embodiments, each of the analyzer controllers 174 may be in communication with a respective one of the spectroscopic analyzers 172. For example, the analyzer controllers 174 may each be physically connected to the respective spectroscopic analyzer 172. In some such embodiments, the spectroscopic analyzers 172 may each include a housing and at least a portion of the respective analyzer controller 174 may be contained in the housing. In some embodiments, the respective analyzer controllers 174 may be in communication with the respective spectroscopic analyzers 172 via a hard-wired and/or wireless communications link. In some embodiments, the respective analyzer controllers 174 may be physically separated from the respective spectroscopic analyzers 172 and may be in communication with the respective spectroscopic analyzers 172 via a hard-wired communications link and/or a wireless communications link. In some embodiments, physical separation may include being spaced from one another, but within the same building, within the same facility (e.g., located at a common manufacturing facility, such as a refinery), or being spaced from one another geographically (e.g., anywhere in the world). In some physically separated embodiments, both the spectroscopic analyzer 172 and/or the respective analyzer controller 174 may be linked to a common communications network, such as a hard-wired communications network and/or a wireless communications network. Such communications links may operate according to any known hard-wired and/or wireless communications protocols as will be understood by those skilled in the art. Although FIG. 4A schematically depicts each of the analyzer controllers 174A through 174N being separate analyzer controllers, in some embodiments, one or more of the analyzer controllers 174A through 174N may be part of a common analyzer controller configured to control one or more the spectroscopic analyzers 172A through 172N.

In some embodiments, using the standardized analyzer spectra may include transferring one or more spectral models of the first spectroscopic analyzer 172A when in the first state to one or more of the second through $N^{th}$ spectroscopic analyzers 172b through 172N with respective analyzer controllers 174B through 174N after a change to the second through $N^{th}$ spectroscopic analyzers 172B through 172N, such that, when in the second state, analysis by the second through $N^{th}$ spectroscopic analyzers 172B through 172N of multi-component materials results in generation of second through $N^{th}$ material spectra 208B through 208N (FIGS. 4B and 4C) that are consistent with a first-state material spectrum outputted by the first spectroscopic analyzer 172A, when in the first state, resulting from analysis of the first multi-component material 32A. Thus, in some embodiments, the first spectroscopic analyzer 172A and one or more of the second through $N^{th}$ spectroscopic analyzers 172B through 172N will be capable of generating the substantially same spectrum after an event causing the need to calibrate (or recalibrate) one or more of the second through $N^{th}$ spectroscopic analyzers 172B through 172N (e.g., a change to one or more of the second through $N^{th}$ spectroscopic analyzers 172B through 172N, such as maintenance and/or component replacement). In some embodiments, this may improve one or more of the accuracy, reproducibility, or consistency of results outputted by the one or more of the second through $N^{th}$ spectroscopic analyzers 172B through 172 N after a change in state from the first state to the second state. For example, one or more of the second through $N^{th}$ spectroscopic analyzers 172B through 172N with one or more of the respective second through $N^{th}$ analyzer controllers 174B through 174N may be configured to analyze a multi-component material and output plurality of signals indicative of a plurality of material properties of the material based at least in part on a corrected material spectrum, such that the plurality of material properties of the material predicted (or determined) by one or more of the second through $N^{th}$ spectroscopic analyzers 172B through 172N and/or one or more of the second through $N^{th}$ analyzer controllers 174B through 174N are substantially consistent with (e.g., substantially the same as) a plurality of material properties outputted by the first spectroscopic analyzer 172A with first analyzer controller 174A in the first state. This may result in standardizing the one or more second through $N^{th}$ spectroscopic analyzers 172B through 172N with the corresponding one or more of the second through $N^{th}$ analyzer controllers 174B through 174N based at least in part on the first spectroscopic analyzer 172A with the first analyzer controller 174A.

As shown in FIG. 4A, in some embodiments, the first analyzer controller 174A may be configured to determine standardized analyzer spectra for calibration of the plurality of spectroscopic analyzer 172B through 172N when one or more of the spectroscopic analyzers 172B through 172N changes from a first state to a second state. For example, the first analyzer controller 174A, while in the first state and during a first-state time period $T_1$, may be configured to analyze a plurality of different multi-component samples 176 and, based at least in part on the multi-component samples 176, output first-state sample spectra 178 of the different multi-component samples 176. In some embodiments, each of the first-state sample spectra 178 may be collected and stored, for example, in a database. In some embodiments, each of the first-state sample spectra 178 may be associated with a corresponding different multi-component sample 176 and may be indicative of a plurality of different multi-component sample properties. In some embodiments, the first-state sample spectra 178, in combination with material data 179 associated with each of the multi-component samples 176, may be used to output (e.g., develop) one or more spectral model(s) 180, which, in turn, may be used to calibrate the first spectroscopic analyzer 172A with the first analyzer controller 174A, resulting in an analyzer calibration 182. The material data 179 may include any data related to one or more properties associated with one or more of the respective multi-component samples 176. The one or more spectral model(s) 180 may be indicative of relationships (e.g., correlations) between a spectrum or spectra of the first-state sample spectra 178 and one or more properties associated with one or more of respective multi-component samples 176, and the relationships may be used to provide the analyzer calibration 182. In some embodiments, the one or more spectral model(s) 180 may represent a univariate or multivariate regression (e.g., a least-squares regression, a multiple linear regression (MLR), a partial least squares regression (PLS), a principal component regression (PCR)), such as a regression of material data (e.g., one or more properties of the multi-component sample) against a corresponding spectrum of the first-state sample spectra 178. In some embodiments, the one or more spectral model(s) 180 may represent topological modeling by use of nearest neighbor positioning to calculate properties, based on the material data (e.g., one or more properties of the multi-component sample) against a corresponding spectrum of the first-state sample spectra 178, as also will be understood by those skilled in the art. This may facilitate prediction of one or more properties of a material analyzed by the spectroscopic analyzers 172A through 172N, once calibrated, based at least in part on a spectrum associated with the material.

In some embodiments, the plurality of different multi-component samples 176 may include a relatively large number of samples. For example, in some embodiments, in order to calibrate the first spectroscopic analyzer 172A with the first analyzer controller 174A to a desired level of accuracy and/or reproducibility, it may be necessary to analyze hundreds or thousands of multi-component samples 176 that have corresponding material data 179. Due to the relatively large number of multi-component samples 176 used for calibration, the first-state time period $T_1$, which may generally correspond to the time period during which the multi-component samples 176 are analyzed, may take a significant amount of time to complete. For example, in some embodiments, in order to calibrate the first spectroscopic analyzer 172A with the first analyzer controller 174A to a desired level of accuracy and/or reproducibility, due to the relatively large number of samples analyzed, the first-state time period $T_1$ may take dozens of hours or longer to complete.

Following calibration of the first spectroscopic analyzer 172A with the first analyzer controller 174A, the spectral responses of the first spectroscopic analyzer 172A with the first analyzer controller 174A may be standardized, for example, by analyzing one or more first-state portfolio sample(s) 183 to output a standardized analyzer spectra portfolio 184 including one or more first-state portfolio sample spectra 185. For example, the first spectroscopic analyzer 172A with the first analyzer controller 174A, when in the first state, may be used to analyze one or more first-state portfolio sample(s) 183 to output a first-state portfolio spectrum 185 for each of the one or more first-state portfolio sample(s) 183. In some embodiments, the respective first-state portfolio sample spectrum 185 associated with a respective first-state portfolio sample 183 may be stored to develop the standardized analyzer spectra portfolio 184, which may be used to reduce a variance between a second-state portfolio sample spectrum (outputted during a second state) and a corresponding first-state portfolio sample spectrum 185 of the standardized analyzer spectra portfolio 184.

As shown in FIG. 4A, following calibration and/or standardization of the first spectroscopic analyzer 172A with the first analyzer controller 174A, the first spectroscopic analyzer 172A with the first analyzer controller 174A may be used to analyze multi-component materials to predict properties of the multi-component materials analyzed. For example, in some embodiments, the first spectroscopic analyzer 172A with the first analyzer controller 174A may be used as part of a manufacturing process, for example, as described herein with respect to FIGS. 1, 2, and 3. For example, the first spectroscopic analyzer 172A with the first analyzer controller 174A may be used to analyze multi-component materials, and the corresponding material properties predicted (or determined) from the analyses may be used to assist with at least partial control of the manufacturing process or processes.

For example, as shown in FIG. 4A, a manufacturing process may result in generating conditioned materials for analysis 186A (e.g., fluids, such as gases and/or liquids) during the manufacturing process, and multi-component materials associated with the manufacturing process may be diverted for analysis by the first spectroscopic analyzer 172A with the first analyzer controller 174A. In some embodiments, for example, as shown in FIG. 4A, the multi-component material may be conditioned via a sample conditioning assembly to output conditioned material for analysis 186A by the first spectroscopic analyzer 172A with the first analyzer controller 174a, for example, as described previously herein with respect to FIG. 3. In some embodiments, the material conditioning may include one or more of filtering particulates and/or fluid contaminants from the multi-component material, controlling the temperature of the multi-component material (e.g., reducing or increasing the temperature to be within a desired range of temperatures), or controlling the pressure of the multi-component material (e.g., reducing or increasing the pressure to be within a desired range of pressures). In some embodiments, the spectroscopic analyzers 172 and/or the analyzer controllers 174 may analyze unconditioned materials and/or semi-conditioned materials to output predicted (or determined) material data for the materials for use in example processes.

Upon analysis of the multi-component materials, which may be a feed to a processing unit and/or an output from a processing unit, the first spectroscopic analyzer 172A with the first analyzer controller 174A, using the analyzer calibration 182, may output a plurality of material spectra 188A and, based at least in part on the material spectra 188A, predict a plurality of material properties associated with the multi-component materials. In some embodiments, the material spectra 188A and the associated predicted or determined material properties may be stored in a database as predicted (or determined) material data 190A. It is contemplated that additional material data associated with the multi-component materials analyzed may also be included in the database to supplement the predicted or determined material properties. For example, the database may define a library including material data including correlations between the plurality of material spectra and the plurality of different material properties of the corresponding material.

In some embodiments, the analysis of the multi-component materials may occur during a first material time period $T_1$, as shown in FIG. 4A. As shown in FIG. 42A, in some embodiments, the first analyzer controller 174A (and/or one or more of the plurality of analyzer controllers 174B through 174N, as explained herein) may also be configured to output one or more output signals 192A indicative of the multi-component material properties. The output signal(s) 192A may be used to at least partially control a manufacturing process, for example, as described with respect to FIGS. 1, 2, and 3 (e.g., output signals 192A through 192N). Although the output signals 192A through 192N are shown as individually being communicated to the FCC process controller(s) 24 (FIG. 4C) independently of one another, in some examples, two or more of the output signals 192A through 192N may be combined prior to being communicated to the FCC process controller(s) 24. For example, two or more (e.g., all) of the output signals 192A through 192N may be received at a single receiver, which in turn, communicates the two or more of the combined signals to the FCC process controller(s) 24. In some examples, at least some of the output signal(s) 192A through 192N may be communicated to one or more output device(s) 214 (FIG. 4C), either independently of communication to the FCC process controller(s) 24 or via the FCC process controller(s) 24, for example, following receipt of the output signals 192A through 192N by the FCC process controller(s) 24. The output device(s) 214 may include display devices, such as, for example, a computer monitor and/or portable output devices, such as a laptop computer, a smartphone, a tablet computing device, etc., as will be understood by those skilled in the art. Such communication may be enabled by a communications link, such as a hard-wired and/or wireless communications link, for example, via one or more communications networks (e.g., the network 92 described herein).

As referenced above, in some embodiments, the first analyzer controller 174A may be configured to use the first-state-portfolio sample spectra 185 of the standardized analyzer spectra portfolio 184 to calibrate or recalibrate one or more of the plurality of spectroscopic analyzers 172A through 172N with the respective analyzer controllers 174A through 174N. For example, as shown in FIG. 4A, such change(s) 194 to the plurality of spectroscopic analyzers 172B through 172N that might necessitate recalibration may include, but are not limited to, for example, maintenance performed on the plurality of spectroscopic analyzers 172B through 172N, replacement of one or more components of the plurality of spectroscopic analyzers 172B through 172N, cleaning of one or more components of the plurality of spectroscopic analyzers 172B through 172N, re-orienting one or more components of the plurality of spectroscopic analyzers 172B through 172N, a change in path length (e.g., relative to the path length for prior calibration), or preparing the plurality of spectroscopic analyzers 172B through 172N for use, for example, prior to a first use and/or calibration (or recalibration) of the plurality of spectroscopic analyzers 172B through 172N specific to the materials to which they are intended to analyze.

In some embodiments, using respective portfolio sample-based correction(s) 200B through 200N (see FIG. 4B) based at least in part on the standardized analyzer spectra portfolio 184 to calibrate or recalibrate the plurality of spectroscopic analyzers 172B through 172N may result in the plurality of spectroscopic analyzers 172B through 172N with the respective analyzer controllers 174B through 174N outputting analyzed material spectra and/or predicting corresponding material properties in a manner substantially consistent with a plurality of material properties of the material outputted by the first spectroscopic analyzer 172A with the first analyzer controller 174A in the first state, for example, in a state prior to the change(s) 194 to the plurality of spectroscopic analyzers 172B through 172N.

For example, as shown in FIG. 4A, in some embodiments, the plurality of analyzer controllers 174B through 174N may be configured to analyze, via the respective spectroscopic analyzers 172B through 172N, when in the second state, a selected plurality of portfolio sample(s) 183 to output second-state portfolio sample spectra 198 for the selected plurality of different second-state portfolio sample(s) 196. In some embodiments, the portfolio sample(s) 183 may be the first-state portfolio sample(s) 183 and/or the second-state portfolio sample(s) 196. In some embodiments, each of the second-state portfolio sample spectra 196A through 196N may be associated with a corresponding different portfolio sample 183. As shown in FIG. 4A, in some embodiments, the portfolio sample(s) 183 may include a number of samples significantly lower than the number of samples of the plurality of multi-component samples 176. For example, in some embodiments, in order to calibrate or recalibrate the plurality of spectroscopic analyzers 172B through 172N with the respective analyzer controllers 174B through 174N after the change(s) 194 to achieve a desired level of accuracy and/or reproducibility, for example, an accuracy and/or reproducibility substantially equal to or better than the level of accuracy and/or reproducibility of the first spectroscopic analyzer 172A with the first analyzer controller 174A, in some embodiments, it may only be necessary to analyze as few as ten or fewer of the portfolio sample(s) 183, as explained in more detail herein.

As shown in FIG. 4A, in some embodiments, because it may be necessary to only analyze substantially fewer portfolio sample(s) 183 to achieve results substantially consistent with the results achieved prior to the change(s) 194, a second-state time period $T_2$ during which the portfolio sample(s) 183 or the portfolio sample(s) 196 are analyzed may be significantly less than the first-state time period $T_1$ during which the multi-component samples 176 are analyzed for the output (e.g., the development) of spectral model(s) 180 and analyzer calibration 182. For example, as noted above, in some embodiments, the first-state time period $T_1$ may exceed 100 hours, as compared with the second-state time period $T_2$, which may be less than 20 hours (e.g., less than 16 hours, less than 10 hours, less than 8 hours, less than 4 hours, or less than 2 hours) for each of the plurality of spectroscopic analyzers 172B through 172N.

Thus, in some embodiments, the plurality of spectroscopic analyzers 172B through 172N with the respective analyzer controllers 174B through 174N may be configured to be calibrated or recalibrated to achieve substantially the same accuracy and/or reproducibility of analysis as the first spectroscopic analyzer 172A with first analyzer controller 174A, while using significantly fewer samples to calibrate or recalibrate each of the plurality of spectroscopic analyzers 172B through 172N with the respective analyzer controllers 174B through 174N, as compared to the number of multi-component samples 176 used to calibrate or recalibrate the first spectroscopic analyzer 172A with the first analyzer controller 174A for the development of spectral model(s) 180 and analyzer calibration 182, thus requiring significantly less time for calibration or recalibration. In some embodiments, the calibrated or recalibrated plurality of spectroscopic analyzers 172B through 172N and/or the plurality of analyzer controllers 174B through 174N, calibrated or recalibrated in such a manner, may be capable of generating substantially the same spectra following calibration or recalibration as outputted by the first spectroscopic analyzer 172A with the first analyzer controller 174A, which may result in improved accuracy and/or reproducibility by the first spectroscopic analyzer 172A and each of the plurality of spectroscopic analyzers 172B through 172N. Such accuracy and/or reproducibility may provide the ability to compare analysis results outputted by either the first spectroscopic analyzer 172A or the plurality of spectroscopic analyzers 172B through 172N, which may result in the first spectroscopic analyzer 172A and the plurality of spectroscopic analyzers 172B through 172N being relatively more useful, for example, when incorporated into a manufacturing process involving the processing of multi-component materials received from material sources, such as shown in FIGS. 1 and 2, for example, a petroleum refining-related process, such as an FCC process, a pharmaceutical manufacturing process, or other processes involving the processing of materials.

As shown in FIG. 4A, in some embodiments, each of the plurality of analyzer controllers 174B through 174N also may be configured to compare one or more of the respective second-state portfolio sample spectra 198A through 198B from the portfolio samples to the first-state portfolio sample spectra 185. Based at least in part on the comparison, the plurality of analyzer controllers 174B through 174N further may be configured to determine for one or more of the respective second-state portfolio sample spectra 198A through 198N, a variance 212 (e.g., respective variances 212B through 212N) over a range of wavelengths, wavenumbers, and/or frequencies between the respective second-state portfolio sample spectra 189A through 198N outputted by each of the respective spectroscopic analyzers 172B through 172N and the first-state portfolio sample spectra 185 of the standardized analyzer spectra portfolio 184 outputted by the first spectroscopic analyzer 172A. For example, in some embodiments, the plurality of analyzer controllers 174B through 174N may be configured to determine a difference in magnitude between each of the second-state portfolio sample spectra 198 and the first-state portfolio sample spectra 185 for each of a plurality of wavelengths, wavenumbers, and/or frequencies over one or more ranges of wavelengths, wavenumbers, and/or frequencies, respectively.

In some embodiments, each of the plurality of analyzer controllers 174B through 174N may be configured to determine respective variances 212B through 212N by determining a mean average variance, one or more ratios of variances at respective individual wavelengths, or a combination thereof, for a plurality of wavelengths, wavenumbers, and/or frequencies over a range of wavelengths, wavenumbers, and/or frequencies, respectively. In some embodiments, each of the plurality of analyzer controllers 174B through 174N may be configured to determine a relationship for a plurality of wavelengths, wavenumbers, and/or frequencies over the range of wavelengths, wavenumbers, and/or frequencies, respectively, between the respective second-state portfolio sample spectra 198B through 198N and the first-state portfolio sample spectra 185, and the relationship may include one or more of a ratio, an addition, a subtraction, a multiplication, a division, one or more derivatives, or an equation.

As shown in FIGS. 4A and 4B, in some embodiments, each of the plurality of analyzer controllers 174B through 174N still further may be configured to reduce the respective variance 212B through 212N (FIG. 4B) between the respective second-state portfolio sample spectra 198B through 198N and the first-state portfolio sample spectra 185. For example, each of the plurality of analyzer controllers 174B through 174N may be configured to use respective analyzer portfolio sample-based correction(s) 200B through 200N based at least in part on the previously outputted standardized analyzer spectra portfolio 184 to reduce the respective variances 212B through 212N between the respective second-state portfolio sample spectra 198B through 198N and the first-state portfolio sample spectra 185, so that each of the respective ones of the plurality of spectroscopic analyzers 172B through 172N and/or the respective ones of the plurality of analyzer controllers 174B through 174N is able to output, when in the second state following the change(s) 194 (e.g., during initial set-up or after maintenance), a plurality of signals indicative of a plurality of material properties of an analyzed multi-component material, such that the plurality of material properties of the multi-component material are substantially consistent with a plurality of material properties of the multi-component material that were, or would be, outputted by the first spectroscopic analyzer 172A with the first analyzer controller 174A in the first state. For example, as shown in FIG. 4B, the plurality of spectroscopic analyzers 172B through 172N with the respective analyzer controllers 174B through 174N may be configured to output respective portfolio sample-based correction(s) 200B through 200N, which reduce or substantially eliminate the respective variance 212B through 212N between the second-state portfolio sample spectra 198B through 198N and the respective first-state portfolio sample spectra 185 (FIG. 4A), which, in turn, may reduce or substantially eliminate the respective variance between second-state multi-component material spectra 202 and first-state multicomponent spectra 178, for example, should the same sample be analyzed in both the first and second states.

As shown in FIG. 4B, in some embodiments, following the change(s) 194 to the plurality of spectroscopic analyzers 172B through 172N and/or the plurality of analyzer controllers 174B through 174N and the calibration or recalibration in the second state, the plurality of spectroscopic analyzers 172B through 172N may be used to analyze a plurality of multi-component materials. For example, as shown in FIG. 4B, a manufacturing process may include a plurality of material sources for respective multi-component materials (e.g., fluids, such as gases and/or liquids) of the manufacturing process (e.g., an FCC process and/or a related upstream process and/or downstream process), and multi-component materials associated with the manufacturing process may be diverted for analysis by one or more of the plurality of spectroscopic analyzers 172B through 172N with the respective analyzer controllers 174B through 174N. In some embodiments, for example, as shown in FIG. 4B, the multi-component materials may be conditioned via material conditioning (e.g., as described herein) to output conditioned materials for analysis 204B through 204N by the respective spectroscopic analyzers 172B through 172N with the respective analyzer controllers 174B through 174N. In some embodiments, material conditioning may include one or more of filtering particulates and/or fluid contaminants from the multi-component material, controlling the temperature of the multi-component material (e.g., reducing or increasing the temperature to be within a desired range of temperatures), or controlling the pressure of the multi-component material (e.g., reducing or increasing the pressure to be within a desired range of pressures). In some embodiments, the manufacturing processes, the material sources, the material conditioning, and/or the conditioned materials for analysis 204B through 204N, may substantially correspond to the previously-discussed FCC process, material source(s), material conditioning, and/or the conditioned material for analysis (see, e.g., FIGS. 1-3).

In some embodiments, each of the plurality of spectroscopic analyzers 172B through 172N with each of the respective analyzer controllers 174B through 174N may be configured to analyze, when in the second state, the multi-component materials received from the respective material sources and output a material spectrum corresponding to the respective multi-component materials, for example, as described previously herein with respect to FIGS. 1 and 2. As shown in FIG. 4B, the plurality of spectroscopic analyzers 172B through 172N with the respective analyzer controllers 174B through 174N also may be configured to use the second through $N^{th}$ material spectrum 202B through 202N to output respective corrected material spectra 206B through 206N, based at least in part on the standardized analyzer spectra portfolio 184, the respective portfolio sample-based correction(s) 2003 through 200N', for each of the respective multi-component materials. In some embodiments, each of the corrected material spectra 206B through 206N may include one or more of an absorption-corrected spectrum, a transmittance-corrected spectrum, a transflectance-corrected spectrum, a reflectance-corrected spectrum, or an intensity-corrected spectrum, for example, and/or a mathematical treatment of the material spectrum, such as, for example, a second derivative of the material spectrum. For example, based at least in part on the respective corrected material spectra 206B through 206N, the respective analyzer controllers 174B through 174N may be configured to output a plurality of signals indicative of a plurality of material properties of the respective multi-component materials, and the plurality of material properties may be substantially consistent with (e.g., substantially the same as) a plurality of material properties of the multi-component materials that would be outputted by the first spectroscopic analyzer 172A with the first analyzer controller 174A. Thus, in some such embodiments, the respective corrected material spectra 206B through 206N may result in standardized spectra, such that the corrected material spectra 208B through 208N have been standardized based at least in part on the standardized analyzer spectra portfolio 184, so that the respective corrected material spectra 208B through 208N are the substantially the same material spectra that would be outputted by the first spectroscopic analyzer 172A with the first analyzer controller 174A.

In some embodiments, this may render it possible to directly compare the results of analysis by the plurality of spectroscopic analyzers 172B through 172N with the respective analyzer controllers 174B through 174N with results of analysis by the first spectroscopic analyzer 172A with the first analyzer controller 174A. In some embodiments, this may render it possible to directly compare the results of analysis by each of the plurality of spectroscopic analyzers 172B through 172N with each of the respective analyzer controllers 174B through 174N with one another. In addition, as noted above, in some embodiments, using the portfolio sample-based correction(s) 200B through 200N to calibrate or recalibrate of the plurality of spectroscopic analyzers 172B through 172N with the respective analyzer controllers 174B through 174N to achieve the standardization may require the analysis of significantly fewer samples (e.g., the second-state portfolio samples 198) as compared to the original calibration of the first spectroscopic analyzer 172A with first analyzer controller 174A during the first state. This may also significantly reduce the time required to calibrate or recalibrate each of the plurality of spectroscopic analyzers 172B through 172N with each of the respective analyzer controllers 174B through 174N.

Upon analysis of the multi-component materials from the material source(s), which may be feed(s) to one or more processing units and/or an output(s) from one or more processing units, the plurality of spectroscopic analyzers 172B through 172N with the respective analyzer controllers 174B through 174N may establish a plurality of corrected material spectra 208B through 208N and, based at least in part on the corrected material spectra 208B through 208N, predict a plurality of material properties associated with the multi-component materials. In some embodiments, the corrected material spectra 208B through 208N and the associated predicted or determined material properties may be stored in a database as respective predicted (or determined) material data 210B through 210N. It is contemplated that additional material data associated with the multi-component materials analyzed may also be included in the database to supplement the predicted or determined material properties. For example, the database may define a library including material data and/or including correlations between the plurality of material spectra and the plurality of different material properties of the corresponding materials.

As shown in FIG. 4C, in some embodiments, the plurality of analyzer controllers 174B through 174N may also be configured to output one or more output signals 192B through 192N indicative of the respective multi-component material properties. The output signal(s) 192B through 192N may be used to at least partially control a manufacturing process. For example, as shown in FIG. 4C, the output signal(s) 192B through 192N may be communicated to one or more FCC process controllers 24 (see also FIG. 1) configured, based at least in part on the output signal(s) 192B through 192N, to output one or more processing unit control signals 30 (see also FIG. 1) for at least partially controlling operation of one or more material processing unit(s) 34 configured to process a multi-component material. In some embodiments, the FCC process controller(s) 24 also may be configured to receive one or more processing parameter(s) 32 and based at least partially on the output signal(s) 192A through 192N and/or the processing parameter(s) 32, output the one or more processing unit control signal(s) 30 to at least partially control operation of the one or more material processing unit(s) 34, for example, as described herein with respect to FIGS. 1 and 2. In some examples, at least some of the output signal(s) 192A through 192N may be communicated to one or more output devices 214, such as, for example, printers, display devices, such as a computer monitor and/or portable output devices, such as a laptop computer, a smartphone, a tablet computing device, a printer, etc., as will be understood by those skilled in the art. Such communication may be enabled by one or more communications links, such as a hard-wired and/or wireless communications link, for example, via one or more communication networks.

In some embodiments, as explained herein, using the portfolio sample-based correction(s) 200B through 200N to calibrate or recalibrate the plurality of spectroscopic analyzers 172B through 172N may result in the plurality of spectroscopic analyzers 172B through 172N with the respective analyzer controllers 174B through 174N generating analyzed material spectra and/or predicting corresponding material properties in a manner substantially consistent with a plurality of material properties outputted by the first spectroscopic analyzer 172A with the first analyzer controller 174A.

Although not shown in FIGS. 4A and 4B, in some embodiments, the plurality of analyzer controllers 174B through 174N, based at least in part on the respective portfolio sample-based correction(s) 200B through 200N, may be configured to output one or more gain signals for controlling one or more analyzer sources, analyzer detectors, and/or detector responses, such that the plurality of spectroscopic analyzers 172B through 172N with the respective analyzer controllers 174B through 174N, when analyzing a multi-component material, output a corrected material spectrum or spectra that are standardized according to the standardized analyzer spectra portfolio 184. Thus, in some embodiments, rather than generating a material spectrum when analyzing a multi-component material, and thereafter correcting the material spectrum based at least in part on the variance and the portfolio sample-based correction(s) 200 developed to reduce the variance to output a corrected material spectrum, the plurality of spectroscopic analyzers 172B through 172N with the respective analyzer controllers 174B through 174N may be configured to output a respective corrected material spectrum 206B through 206N by adjusting the detector gain, for example, without prior generation of a material spectrum, which is thereafter corrected. Rather, in some embodiments, based at least in part on the respective variance(s) 212B through 212N, the plurality of spectroscopic analyzers 172B through 172N with the plurality of analyzer controllers 174B through 174N may be configured to adjust the gain associated with the respective analyzer sources, detectors, and/or detector responses, so that the plurality of spectroscopic analyzers 172B through 172N with the respective analyzer controllers 174B through 174N output corrected material spectra 208B through 208N that reduces or substantially eliminates the respective variance(s) 212B through 212N.

FIG. 5A, FIG. 5B, FIG. 5C, FIG. 5D, and FIG. 5E are a block diagram of an example method 500 to enhance or optimize a fluid catalytic cracking (FCC) process associated with a refining operation, during the FCC process, according to embodiments of the disclosure. The example method 500 is illustrated as a collection of blocks in a logical flow graph, which represent a sequence of operations. In the context of software, where applicable, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described blocks may be combined in any order and/or in parallel to implement the method.

FIG. 5A through FIG. 5E are a block diagram of the example method 500 to enhance or optimize a fluid catalytic cracking (FCC) process associated with a refining operation, during the FCC process, according to embodiments of the disclosure. At 502 (FIG. 5A), the example method 500 may include supplying hydrocarbon feedstock to an FCC processing assembly for FCC processing to produce an FCC effluent, for example, as described herein.

At 504, the example process 500 may include determining whether the hydrocarbon feedstock is within a target temperature range, a target pressure range, and/or a target flow rate, for example, as described herein.

If, at 504, it is determined that the temperature, pressure, or target flow rate is not within one or more of the target ranges, at 506, the example method 500 may include adjusting the temperature, the pressure, and/or the flow rate of the hydrocarbon feedstock to be within the target ranges and returning to 504 to repeat the determination.

If, at 504, it is determined that the temperature, pressure, or target flow rate are within the target ranges, at 508, the example method 500 may include conditioning, via a sample conditioning assembly, a sample of the hydrocarbon feedstock for analysis by a spectroscopic analyzer, for example, as described herein.

At 510, the example method 500 may include determining whether the conditioned hydrocarbon feedstock sample is within target parameters for analysis. This may include determining whether water, particulates, and/or other contaminates have been removed from the conditioned hydrocarbon feedstock sample, and/or whether the conditioned sample is within a desired predetermined temperature range for improving the accuracy of the analysis by the spectroscopic analyzer(s).

If, at 510, it is determined that the conditioned hydrocarbon feedstock sample is not within target parameters for analysis, the example method 500, at 512, may include adjusting one or more parameters associated with operation of the sample conditioning assembly, such that the conditioned hydrocarbon feedstock sample is within the target parameters and returning to 510 to repeat the determination.

If, at 510, it is determined that the conditioned hydrocarbon feedstock sample is within target parameters for analysis, the example method 500, at 514, may include supplying the conditioned hydrocarbon feedstock sample to the spectroscopic analyzer(s) for analysis, for example, as described herein.

The example method 500, at 516, may include analyzing, via the spectroscopic analyzer(s), the conditioned hydrocarbon feedstock sample to predict (or determine) hydrocarbon feedstock properties (and/or parameters), for example, as described herein.

At 518 (FIG. 5B), the example method 500 may include determining whether the hydrocarbon feedstock properties are within desired ranges of property targets for the hydrocarbon feedstock.

If, at 518, it is determined that the hydrocarbon feedstock properties are not within the desired ranges of the property targets for the hydrocarbon feedstock, the example method 500, at 520, may include altering the hydrocarbon feedstock toward the target properties to be within the desired ranges of property targets for the hydrocarbon feedstock and returning to 518 to repeat the determination.

If, at 518, it is determined that the hydrocarbon feedstock properties are within the desired ranges of the property targets for the hydrocarbon feedstock, the example method 500, at 522, may include supplying the hydrocarbon feedstock to a riser of the FCC processing assembly, for example, as described herein.

At 524, the example method 500 may include determining whether the riser is operating within a desired range of a predetermined target riser temperature.

If, at 524, it is determined that the riser is not operating within the desired range of the predetermined target riser temperature, the example method 500, at 526, may include altering the riser temperature toward the target riser temperature and returning to 524 to repeat the determination.

If, at 524, it is determined that the riser is operating within the desired range of the predetermined target riser temperature, the example method 500, at 528, may include supplying catalyst to the riser to provide a reaction mixture including the hydrocarbon feedstock and catalyst, for example, as described herein.

At 530 (FIG. 5C), the example method 500 may include determining whether the FCC reactor is operating within desired ranges of predetermined target FCC reactor parameters.

If, at 530, it is determined that the FCC reactor is not operating within the desired ranges of the predetermined target FCC reactor parameters, the example method 500, at 532, may include altering the FCC reactor operating parameters toward the predetermined target FCC reactor parameters and returning to 530 to repeat the determination.

If, at 530, it is determined that the FCC reactor is operating within the desired ranges of the predetermined target FCC reactor parameters, the example method 500, at 534, may include supplying the reaction mixture to an FCC reactor to produce FCC effluent, for example, as described herein.

At 536, the example method 500 may include conditioning, via a sample conditioning assembly, a reaction mixture sample and/or an FCC effluent sample for analysis by one or more spectroscopic analyzers. In some embodiments, the one or more spectroscopic analyzers may be calibrated to generate standardized spectral responses, for example, as described herein.

At 538, the example method 500 may include determining whether the conditioned reaction mixture sample and/or the FCC effluent sample is/are within desired ranges of target parameters for analysis. This may include determining whether water, particulates, and other contaminates have been removed from the conditioned reaction mixture sample and/or the FCC effluent sample, and/or whether the conditioned sample is within a predetermined temperature range for improving the accuracy of the analysis by the spectroscopic analyzer.

If, at 538, it is determined that the conditioned reaction mixture sample and/or the FCC effluent sample is/are not within the desired ranges of the target parameters for analysis, the example method 500, at 540, may include adjusting one or more parameters associated with operation of the sample conditioning assembly such that the conditioned reaction mixture sample and/or the FCC effluent sample is/are within the target parameters and returning to 538 to repeat the determination.

If, at 538, it is determined that the conditioned reaction mixture sample and/or the FCC effluent sample is/are within the desired ranges of the target parameters for analysis, the example method 500, at 542, may include supplying the conditioned reaction mixture sample and/or the FCC effluent sample to the one or more spectroscopic analyzers for analysis, for example, as described herein.

At 544 (FIG. 5D), the example method 500 may include analyzing, via the one or more spectroscopic analyzers, the conditioned reaction mixture sample and/or the conditioned FCC effluent sample to predict (or determine) the reaction mixture properties (and/or parameters) and/or the FCC effluent properties (and/or parameters), for example, as described herein. In some embodiments, the one or more spectroscopic analyzers may be calibrated to generate standardized spectral responses, for example, as described herein.

At 546, the example method may include determining whether the reaction mixture properties and/or the FCC effluent properties is/are within desired ranges of respective property targets.

If, at 546, it is determined that the reaction mixture properties and/or the FCC effluent properties is/are not within the desired ranges of the respective property targets, the example method 500, at 548, may include altering one or more of the hydrocarbon feedstock, the riser operating parameters, or the FCC reactor operating parameters according to differences between the reaction mixture properties and/or the FCC effluent properties and the property targets, and returning to 546 to repeat the determination.

If, at 546, it is determined that the reaction mixture properties and/or the FCC effluent properties is/are within the desired ranges of the respective property targets, the example method 500, at 550, may include supplying the FCC effluent to one or more downstream processing units to separate the FCC effluent into downstream products, for example, as described herein.

At 552, the example method 500 may include conditioning, via a sample conditioning assembly, one or more downstream product samples for analysis by one or more spectroscopic analyzers, for example, as described herein.

At 554 (FIG. 5E), the example method 500 may include determining whether the conditioned one or more downstream product samples is/are within desired ranges of target parameters for analysis. This may include determining whether water, particulates, and other contaminates have been removed from the conditioned one or more downstream product samples, and/or whether the conditioned samples is/are within a desired predetermined temperature range for improving the accuracy of the analysis by the spectroscopic analyzer.

If, at 554, it is determined that the conditioned one or more downstream product samples is/are not within the desired ranges of the target parameters for analysis, the example method 500, at 556, may include adjusting one or more parameters associated with operation of the sample conditioning assembly such that the conditioned one or more downstream product samples is/are within the desired ranges of the target parameters, and returning to 554 to repeat the determination.

If, at 554, it is determined that the conditioned one or more downstream product samples is/are within the desired ranges of the target parameters for analysis, the example method 500, at 558, may include supplying the conditioned one or more downstream product samples to the one or more spectroscopic analyzers for analysis, for example, as described herein.

At 560, the example method 500 may include analyzing, via the one or more spectroscopic analyzers, the conditioned one or more downstream product samples to predict the properties (and/or parameters) of the one or more downstream products, for example, as described herein. In some embodiments, the one or more spectroscopic analyzers may be calibrated to generate standardized spectral responses, for example, as described herein.

At 562, the example method 500 may include determining whether the properties of the one or more downstream products are within desired ranges of property targets.

If, at 562, it is determined that the properties of the one or more downstream products are not within the desired ranges of the property targets, the example method 500, at 564, may include altering one or more of the hydrocarbon feedstock, the riser operating parameters, the FCC reactor operating parameters, or the downstream processing units operating parameters according to differences between the properties of the one or more downstream products and the property targets, for example, as described herein. Thereafter, at 566, the example method may include returning to 502 and continuing to alter the hydrocarbon feedstock and/or operating parameters to drive the FCC process toward target properties.

If, at 562, it is determined that the properties of the one or more downstream products are within the desired ranges of the property targets, the example method 500, at 566, may include returning to 502 and continuing to monitor and/or control the FCC process according to the method 500.

In some embodiments, the example method 500 may result in causing the FCC process to produce one or more of: intermediate materials having one or more properties within a selected range of one or more target properties of the intermediate materials, unit materials having one or more properties within a selected range of one or more target properties of the unit materials, or downstream materials having one or more properties within a selected range of one or more target properties of the downstream materials. In some embodiments, this may cause the FCC process to achieve material outputs that more accurately and responsively converge on one or more of the target properties. In some embodiments, the example method may result in optimizing one or more of: (a) one or more target properties of the one or more intermediate materials, (b) one or more target properties of the one or more unit materials, (c) or one or more target properties of one or more downstream materials produced by the one or more second processing units, thereby to optimize the FCC process to achieve material outputs that more accurately and responsively converge on one or more of the target properties.

Example 1

Different hydrocarbon feedstocks will result in different yields from an FCC process. If an FCC processing unit is operating against a constraint or constraints, the FCC process may need to adjust to avoid exceeding equipment limitations. Typical process parameters or process variables for an FCC process may include feed rate, reactor temperature, feed preheat, and/or pressure. Process responses from each of the process parameters or variables may be non-linear. The optimum set of conditions to increase process and/or economic efficiency in view of unit constraints may depending on, for example, feed quality. Table 1 below provides example feed properties, process conditions, equipment constraints, and product yields, that may be adjusted to increase or optimize process and/or economic efficiency, for four test conditions: normal FCC process operation, new feed with multivariable optimization, new feed with only feed rate varied, and new feed with only real-time optimization.

TABLE 1

|  | Normal Operation | New Feed w/Multi-variable Optimization | New Feed w/Only Rate Varied | New Feed w/Only RTO Varied |
|---|---|---|---|---|
| Feed Properties/ Params. | | | | |
| API | 24.6 | 21.8 | 21.8 | 21.8 |
| UOP K | 11.69 | 11.77 | 11.77 | 11.77 |
| Concarbon (%) | 0.15 | 0.59 | 0.59 | 0.59 |
| Nitrogen (ppm) | 1150 | 162 | 162 | 162 |
| Sulfur (%) | 0.34 | 0.55 | 0.55 | 0.55 |
| 1-Ring Aromatics (%) | 35 | 29 | 29 | 29 |
| 2-Ring Aromatics (%) | 34 | 26 | 26 | 26 |
| 3-Ring Aromatics (%) | 17 | 25 | 25 | 25 |
| 4-Ring Aromatics (%) | 14 | 20 | 20 | 20 |
| Process Parameters | | | | |
| Feed Rate (% capacity) | 100 | 95.3 | 83.8 | 100 |
| Reactor Temp. (F.) | 1010 | 992 | 1006 | 986 |
| Reactor Pressure (psig) | 34.7 | 33.6 | 32.3 | 34.2 |

TABLE 1-continued

|  | Normal Operation | New Feed w/Multi-variable Optimization | New Feed w/Only Rate Varied | New Feed w/Only RTO Varied |
|---|---|---|---|---|
| Equipment Constraints | | | | |
| Wet Gas Compressor (%) | 100 | 100 | 100 | 100 |
| Main Air Blower (%) | 100 | 90 | 84 | 94 |
| Yields | | | | |
| Conversion (lv %) | 77.55 | 74.33 | 76.83 | 73.59 |

The results in Table 1 show that the application of real-time optimization using spectroscopic analyzers may facilitate the FCC process to automatically adjust processing conditions, for example, to maximize processing as feedstock quality changes. Without determining feedstock quality using spectroscopic analyzers and real-time optimization, the FCC process may operate at a non-optimum condition until a model optimizer is run and the results implemented. In some embodiments, advanced process control and on-line material analysis by spectroscopic analyzers may be used to manipulate multiple FCC processing variables (e.g., one or more of the variables shown in Table 1 and/or any variables and/or parameters described herein) to push the FCC processing unit against unit operational constraints, for example, to improve or maximize economic and/or processing efficiency associated with the FCC process. In some embodiments, on-line real-time optimization may be used to choose a set of operating conditions to improve or maximize economic and/or processing efficiency.

Example 2

FIG. 6A is a table illustrating spectroscopic analysis data associated with an example FCC process including samples of hydrotreater charges and products, and FCC feeds used to control relative amounts of each hydrocarbon class shown in weight percent, according to embodiments of the disclosure. FIG. 6B is a table illustrating minimum and maximum amounts for a calibration set shown in weight percent for example hydrocarbon classes related to the data shown in FIG. 6A, according to embodiments of the disclosure. Two hundred-fifty samples, including hydrotreater charges and products, and FCC feeds were used to create a PLS model for predicting weight percent for each hydrocarbon class. The samples were analyzed using an on-line spectroscopic analyzer for example, as described herein, according to some embodiments. Wavelengths ranging from about 1140 nanometers to about 2300 nanometers, and/or one or more bands within the range were chosen for each group, and a results summary appears in FIG. 6B. In some embodiments, wavelengths for near-infrared (NIR) analysis may range from about 780 nanometers to about 2500 nanometers, and/or one or more wavelength bands within the range may be analyzed; wavenumbers for Raman analysis may range from about 200 wavenumbers ($cm^{-1}$) to about 3700 wavenumbers ($cm^{-1}$), and/or one or more wavenumber bands within the range may be analyzed; wavenumbers for mid-infrared (MIR) analysis may range from about 200 wavenumbers ($cm^{-1}$) to about 4000 wavenumbers ($cm^{-1}$), and/or one or more wavenumber bands within the range may be analyzed; and wavelengths for combination NIR analysis and MIR analysis may range from about 780 nanometers (about 12820 wavenumbers) to about 25000 nanometers (about 400 wavenumbers), and/or one or more wavelength bands within the range may be analyzed.

Example 3

Figure 7:
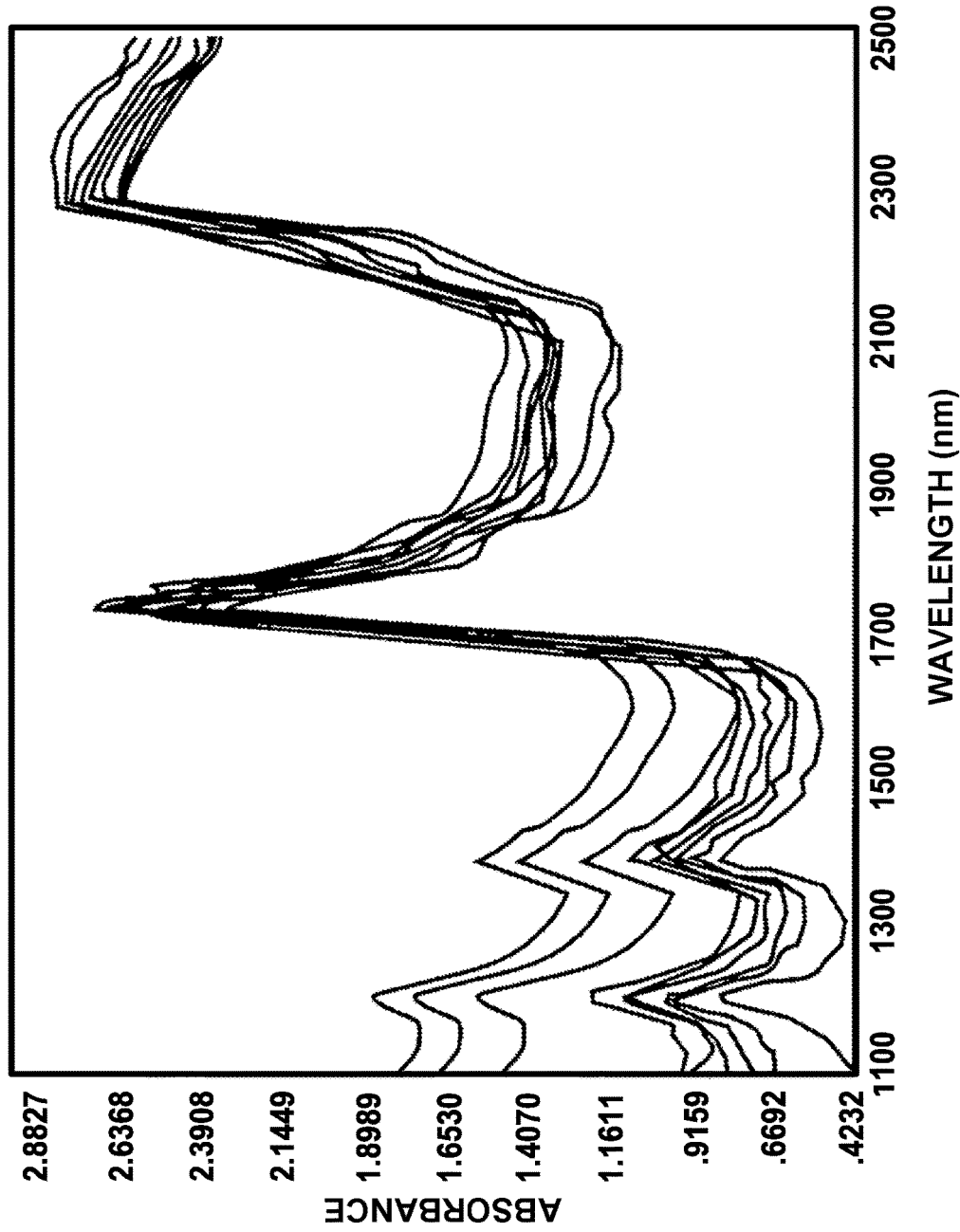
FIG. 7 illustrates example near-infrared (NIR) absorption spectra for example FCC feed samples, according to embodiments of the disclosure.
Figure 8:
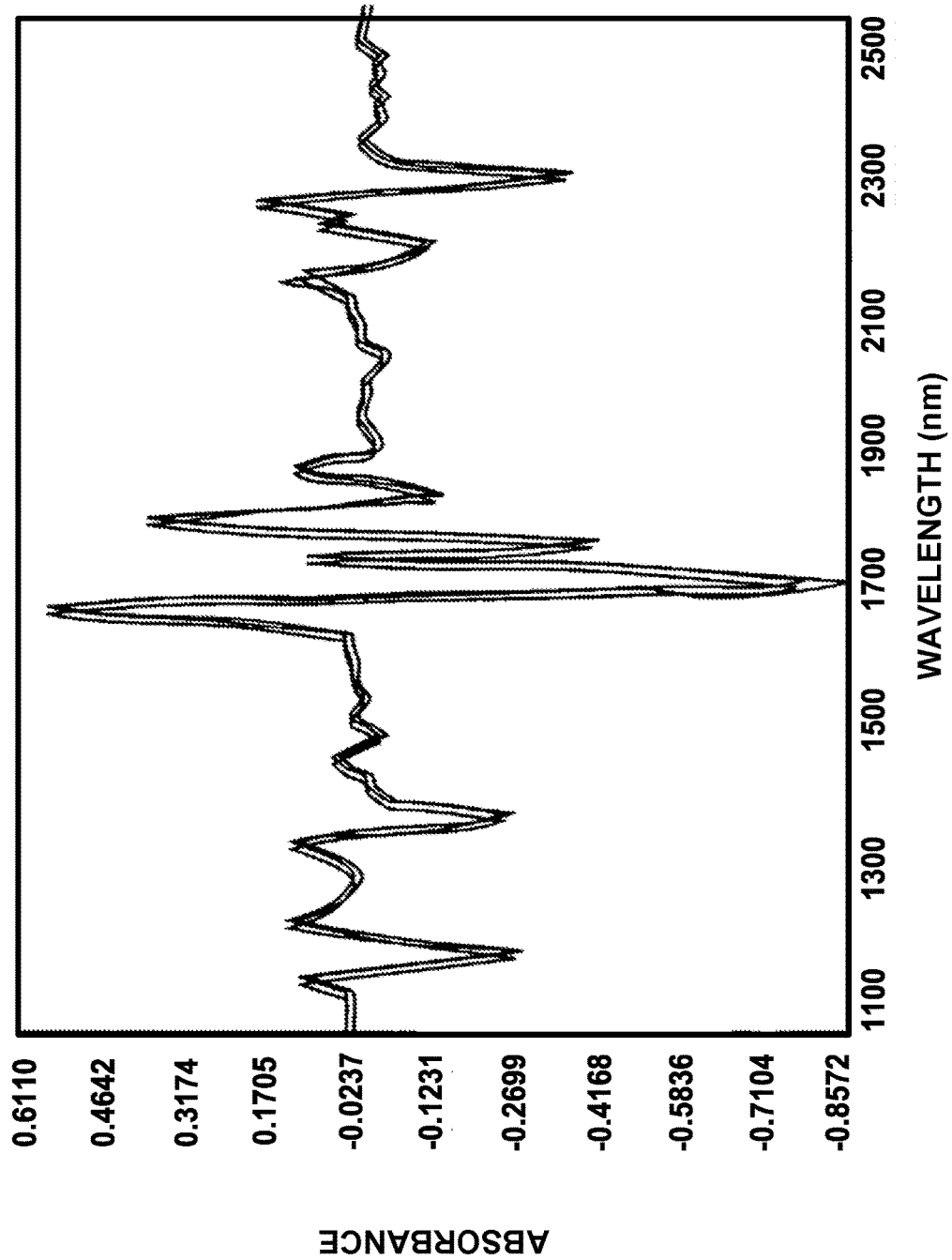
FIG. 8 illustrates example NIR absorption second derivative spectra derived from the example NIR absorption spectra shown in FIG. 7, according to embodiments of the disclosure.

Example 3 is illustrated in FIG. 7 and FIG. 8. FIG. 7 shows example near-infrared (NIR) absorption spectra for example FCC hydrocarbon feed samples, according to embodiments of the disclosure. As described herein, in some embodiments, the spectra may be collected on-line, for example, during the FCC process, and the resulting spectra may be used to predict or determine one or more hydrocarbon feed properties and/or one or more hydrocarbon feed parameters, which may be used to monitor and/or at least partially control the FCC process during the FCC process (e.g., in real-time), for example, as described herein. FIG. 8 illustrates example NIR absorption second derivative spectra derived from the example NIR absorption spectra shown in FIG. 7, according to embodiments of the disclosure. In some embodiments, the second derivative spectra may be used to predict or determine one or more hydrocarbon feed properties and/or one or more hydrocarbon feed parameters, which may be used to monitor and/or at least partially control the FCC process during the FCC process (e.g., in real-time), for example, as described herein. First derivative spectra and/or higher order derivative spectra may provide potential advantages when predicting or determining properties and/or parameters, as compared to spectra, such as the example spectra shown in FIG. 7.

Example 4

Example 4 is illustrated in FIG. 9A and FIG. 9B. FIG. 9A is a table showing NIR regression statistics for each of a plurality of example material properties and/or material parameters, according to embodiments of the disclosure. FIG. 9B is a table showing NIR regression statistics for each of a plurality of example properties, including hydrocarbon group types, according to embodiments of the disclosure.

Example 5

Figure 10:
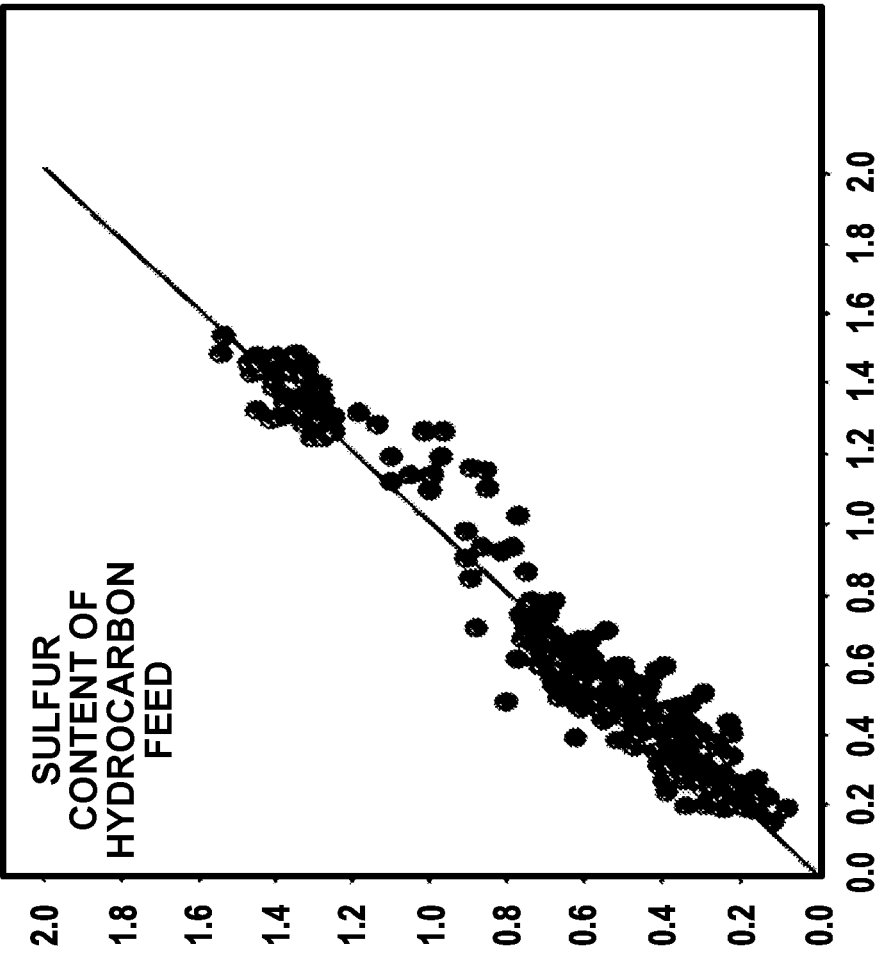
FIG. 10 is a correlation plot showing predicted sulfur content of an example hydrocarbon feed based on analysis by an on-line NIR spectroscopic analyzer versus results obtained from a laboratory analysis, according to embodiments of the disclosure.
Figure 11:
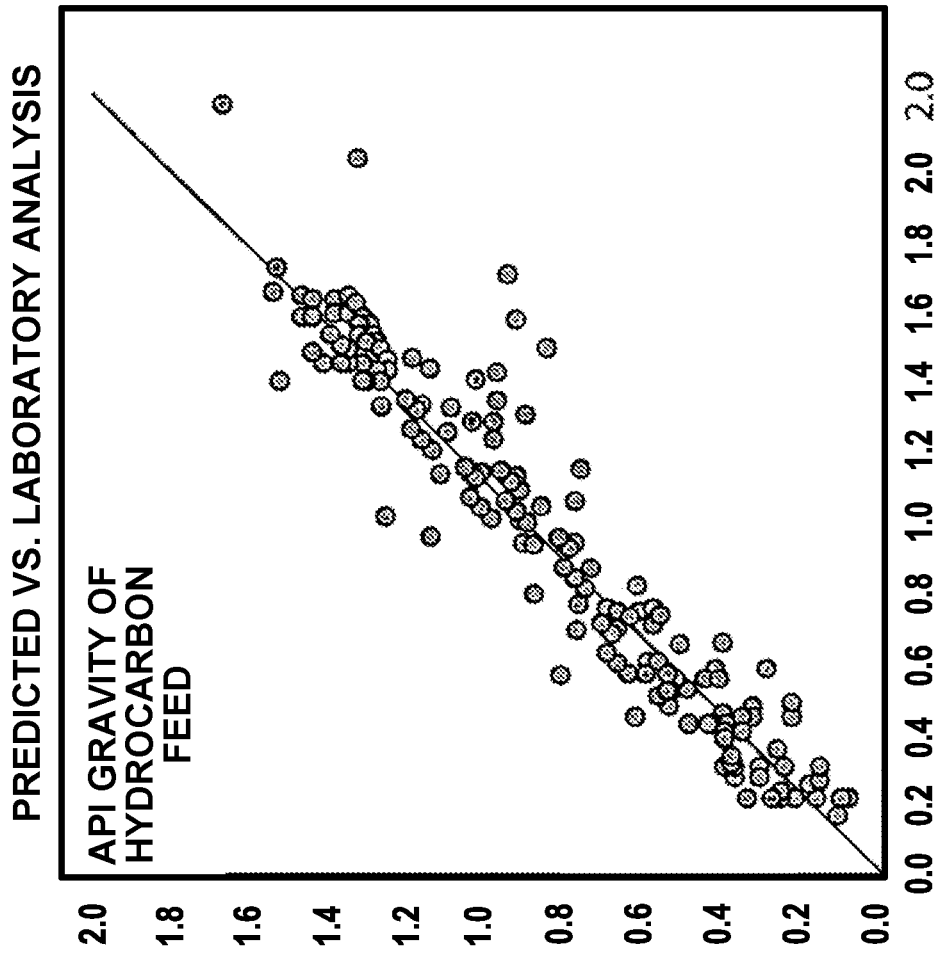
FIG. 11 is a correlation plot showing predicted API gravity of an example hydrocarbon feed based on analysis by an on-line NIR spectroscopic analyzer versus results obtained from a laboratory analysis, according to embodiments of the disclosure.
Figure 12:
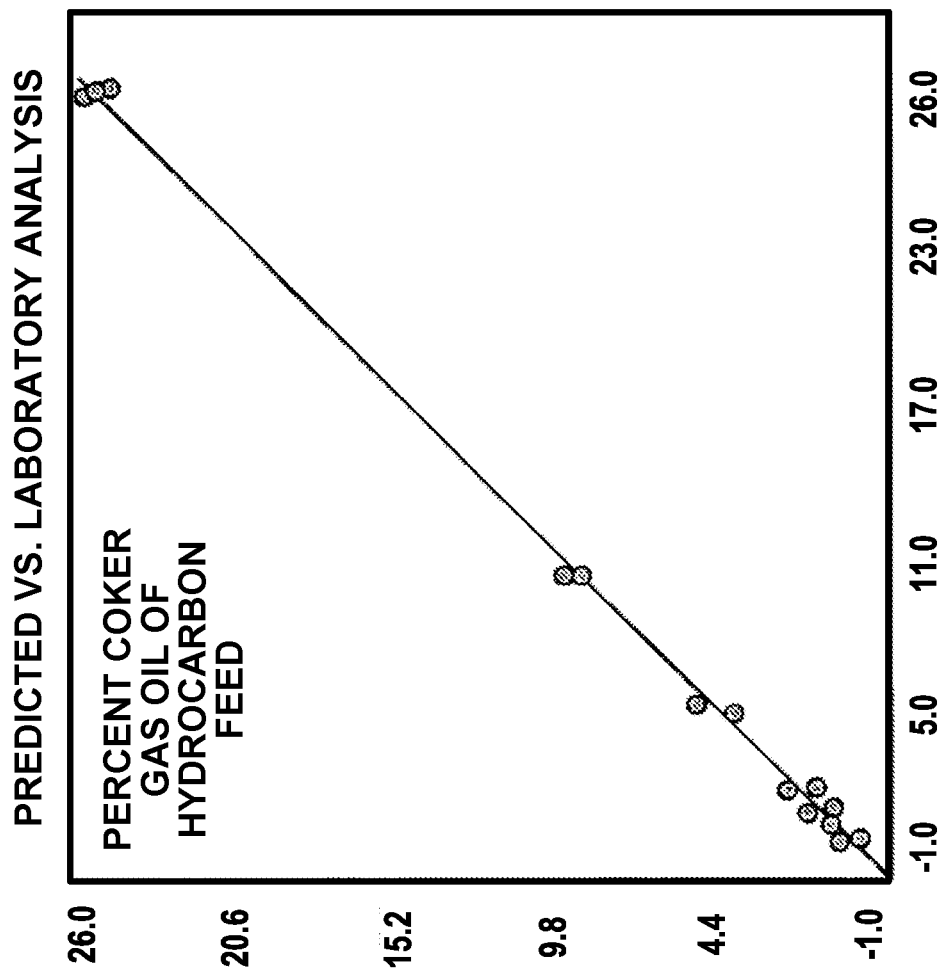
FIG. 12 is a correlation plot showing predicted percent coker gas oil of an example hydrocarbon feed based on analysis by an on-line NIR spectroscopic analyzer versus results obtained from a laboratory analysis, according to embodiments of the disclosure.

Example 5 is illustrated in FIG. 10, FIG. 11, and FIG. 12. FIG. 10 is a correlation plot showing predicted or determined sulfur content of an example hydrocarbon feed based on analysis by an on-line NIR spectroscopic analyzer versus results obtained from a laboratory analysis using traditional laboratory analysis methods, according to embodiments of the disclosure. The laboratory analysis may include one or more of the laboratory analysis techniques described herein, as well as others, including primary test methods. FIG. 11 is a correlation plot showing predicted or determined API gravity of an example hydrocarbon feed based on analysis by an on-line NIR spectroscopic analyzer versus results obtained from a laboratory analysis, according to embodiments of the disclosure. FIG. 12 is a correlation plot showing predicted or determined percent coker gas oil of an example hydrocarbon feed based on analysis by an on-line NIR spectroscopic analyzer versus results obtained from a laboratory analysis, according to embodiments of the disclosure. FIGS. 10-12 show strong respective correlations between the predicted or determined results based on spectroscopic analyzer analysis and processing and the laboratory analysis for the example three material properties and/or material parameters associated with the hydrocarbon feed samples shown in FIGS. 10-12.

FIGS. 10-12 show that hydrocarbon feed properties and/or parameters may be predicted or determined by hydrocarbon group types, which may affect FCC processes and/or products. The properties and/or parameters may be related to the weighting of certain components in the composition of the hydrocarbon feed, such as, for example, mono-aromatics, di-aromatics, tri-aromatics, benzothiophenes, and/or dibenzothiophenes. One or more of the hydrocarbon group types may be determined by the techniques illustrated by the Tables shown in FIG. 6A and FIG. 6B, and/or from changes in specific spectroscopic analyzer wavelength ranges, wavenumber ranges, and/or frequency ranges, such as, for example, in specific infrared absorption bands. In some embodiments, the content of these components in the hydrocarbon feed may be correlated to FCC product properties according to the methods described herein, and this may be used for monitoring, controlling, and/or optimizing operation of one or more of the FCC processing units and/or related FCC processes.

Example 6

Figure 13A:
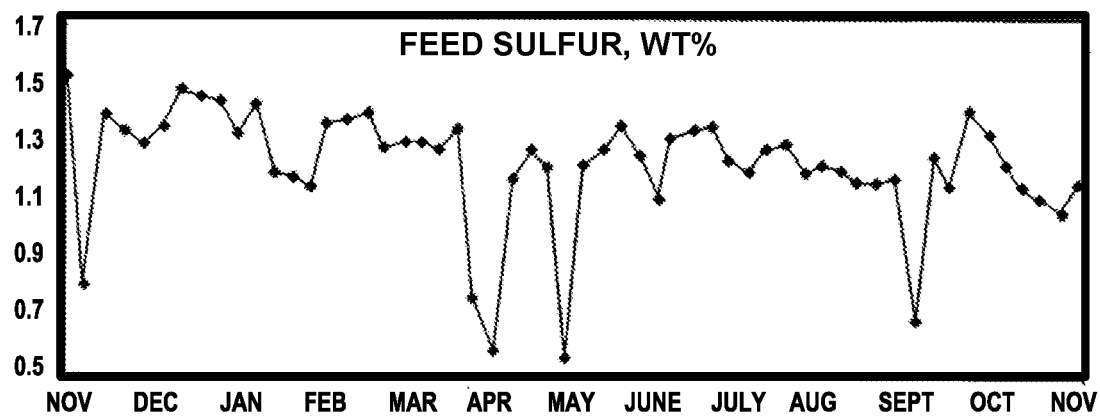
FIG. 13A is a graph showing example hydrocarbon feed sulfur content determined off-line over time, according to embodiments of the disclosure.
Figure 13B:
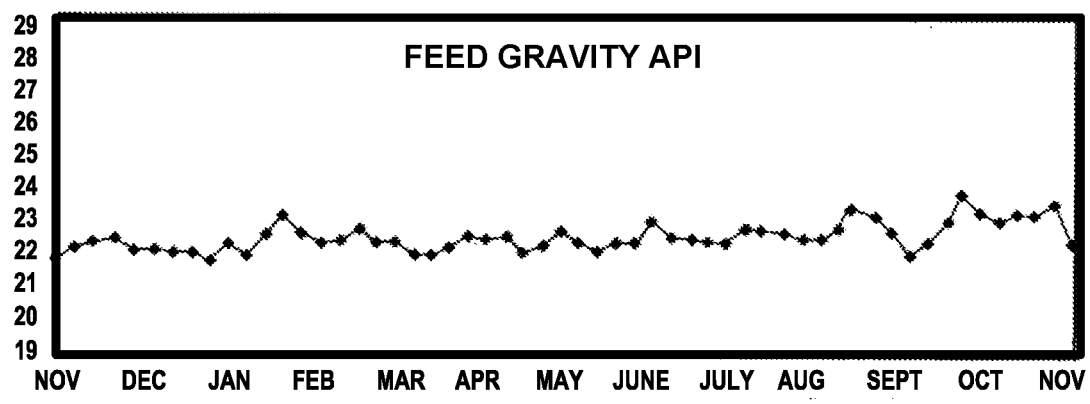
FIG. 13B is a graph showing example hydrocarbon feed API gravity determined off-line over time, according to embodiments of the disclosure.
Figure 13C:
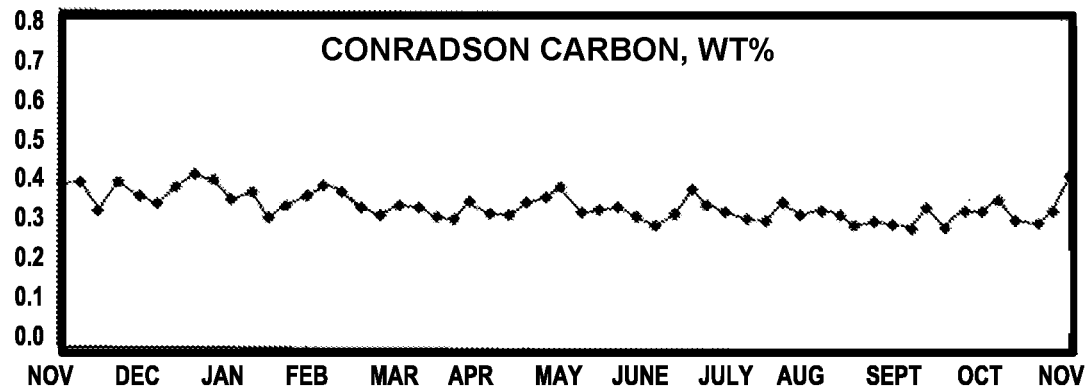
FIG. 13C is a graph showing example hydrocarbon feed Conradson carbon determined off-line over time, according to embodiments of the disclosure.
Figure 14A:
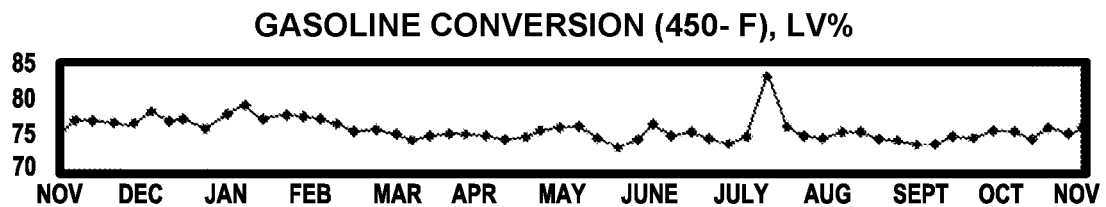
FIG. 14A is a graph showing example gasoline conversions determined off-line over time, according to embodiments of the disclosure.
Figure 14B:
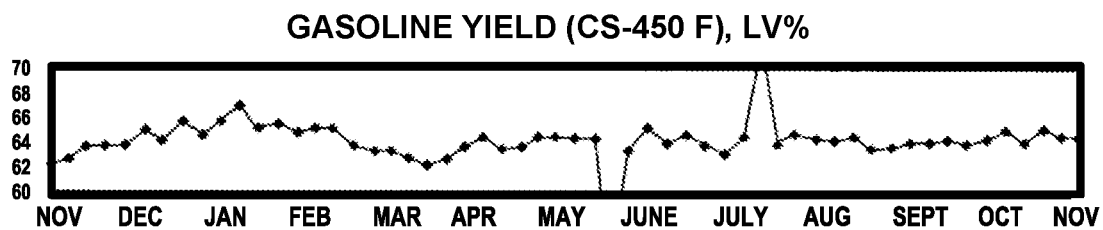
FIG. 14B is a graph showing example gasoline yields determined off-line over time, according to embodiments of the disclosure.
Figure 14C:
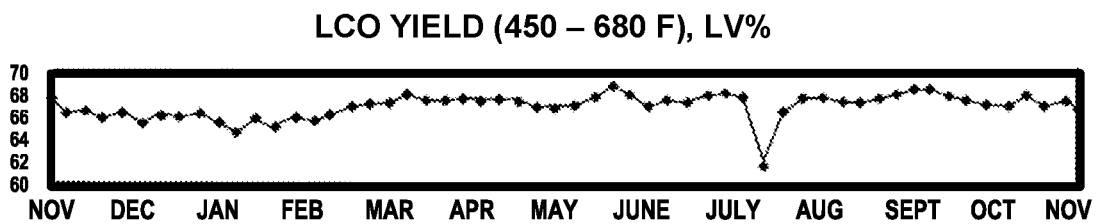
FIG. 14C is a graph showing example light cycle oil (LCO) yields determined off-line over time, according to embodiments of the disclosure.
Figure 14D:
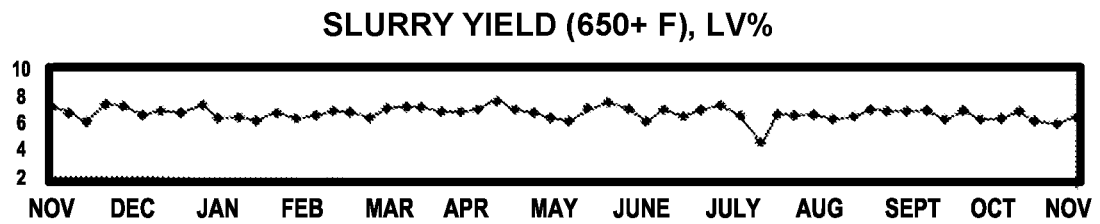
FIG. 14D is a graph showing example slurry yields determined off-line over time, according to embodiments of the disclosure.

Example 6 is illustrated by FIG. 13A, FIG. 13B, FIG. 13C, FIG. 14A, FIG. 14B, FIG. 14C, and FIG. 14. FIG. 13A is a graph showing example hydrocarbon feed sulfur content determined off-line over time. FIG. 13B is a graph showing example hydrocarbon feed API gravity determined off-line over time. FIG. 13C is a graph showing example hydrocarbon feed Conradson carbon determined off-line over time. FIG. 14A is a graph showing example gasoline conversions determined off-line over time. FIG. 14B is a graph showing example gasoline yields determined off-line over time. FIG. 14C is a graph showing example light cycle oil (LCO) yields determined off-line over time. FIG. 14D is a graph showing example slurry yields determined off-line over time.

FIG. 13A through FIG. 13C, and FIG. 14A through FIG. 14D are graphs of FCC processing unit monitoring plots that track hydrocarbon feedstock quality and FCC product yields. The graphs, as shown, are not based on information obtained during the FCC process, and thus, the information may not be used to control the FCC process and/or the FCC processing units while the FCC process is proceeding. Rather, the graphs merely show weekly or monthly trends, and thus, they do not facilitate monitor, control, and/or optimization of operation of one or more of the FCC processing units and/or related FCC processes.

In some embodiments, the use of one or more spectroscopic analyzers as described herein may facilitate collection of such data on-line, for example, during an associated FCC process to provide real-time data, which may be used as described herein to monitor, control, and/or optimize operation of one or more of the FCC processing units and/or related FCC processes, for example, without waiting for laboratory analysis, which may delay appropriate process and/or processing unit operation changes.

It should be appreciated that at least some subject matter presented herein may be implemented as a computer process, a computer-controlled apparatus, a computing system, or an article of manufacture, such as a computer-readable storage medium. While the subject matter described herein is presented in the general context of program modules that execute on one or more computing devices, those skilled in the art will recognize that other implementations may be performed in combination with other types of program modules. Generally, program modules include routines, programs, components, data structures, and other types of structures that perform particular tasks or implement particular abstract data types.

Those skilled in the art will also appreciate that aspects of the subject matter described herein may be practiced on or in conjunction with other computer system configurations beyond those described herein, including multiprocessor systems, microprocessor-based or programmable consumer electronics, minicomputers, mainframe computers, handheld computers, mobile telephone devices, tablet computing devices, special-purposed hardware devices, network appliances, and the like.

Figure 15:
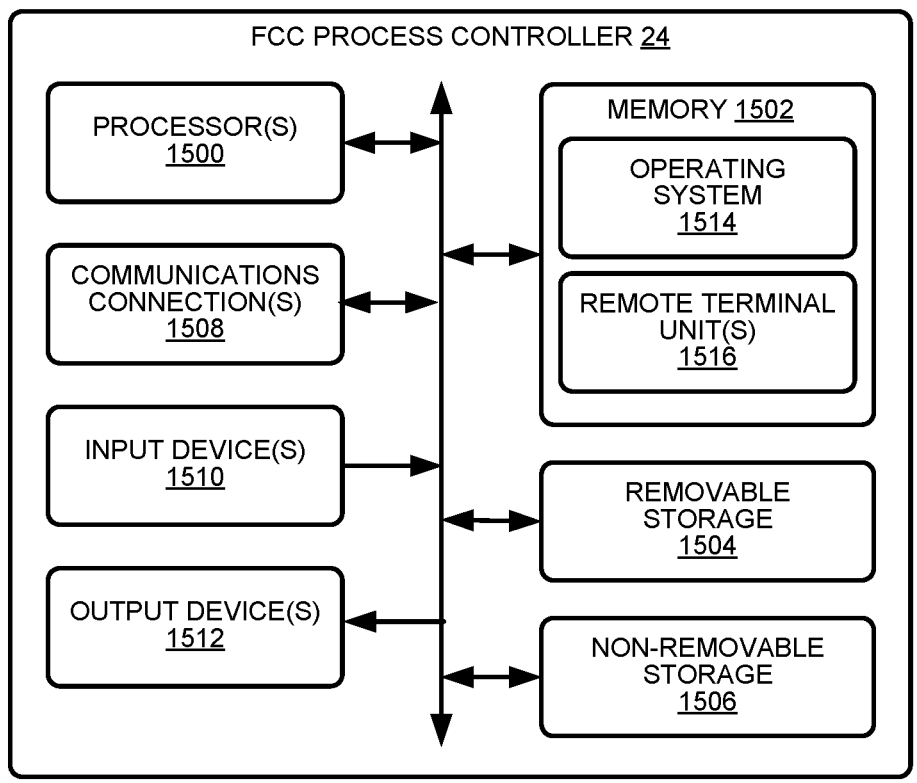
FIG. 15 is a schematic diagram of an example fluid catalytic cracking (FCC) process controller configured to at least partially control an FCC processing assembly, according to embodiments of the disclosure.

FIG. 15 is a schematic diagram of an example FCC process controller 24 configured to at least partially control an FCC processing assembly 10, according to embodiments of the disclosure, for example, as described herein. The FCC process controller 24 may include one or more processor(s) 1500 configured to execute certain operational aspects associated with implementing certain systems and methods described herein. The processor(s) 1500 may communicate with a memory 1502. The processor(s) 1500 may be implemented and operated using appropriate hardware, software, firmware, or combinations thereof. Software or firmware implementations may include computer-executable or machine-executable instructions written in any suitable programming language to perform the various functions described. In some examples, instructions associated with a function block language may be stored in the memory 1502 and executed by the processor(s) 1500.

The memory 1502 may be used to store program instructions that are loadable and executable by the processor(s) 1500, as well as to store data generated during the execution of these programs. Depending on the configuration and type of the FCC process controller 24, the memory 1502 may be volatile (such as random access memory (RAM)) and/or non-volatile (such as read-only memory (ROM), flash memory, etc.). In some examples, the memory devices may include additional removable storage 1504 and/or non-removable storage 1506 including, but not limited to, magnetic storage, optical disks, and/or tape storage. The disk drives and their associated computer-readable media may provide non-volatile storage of computer-readable instructions, data structures, program modules, and other data for the devices. In some implementations, the memory 1502 may include multiple different types of memory, such as static random access memory (SRAM), dynamic random access memory (DRAM), or ROM.

The memory 1502, the removable storage 1504, and the non-removable storage 1506 are all examples of computer-readable storage media. For example, computer-readable storage media may include volatile and non-volatile, removable and non-removable media implemented in any method or technology for storage of information such as computer-readable instructions, data structures, program modules or other data. Additional types of computer storage media that may be present may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile discs (DVD) or other optical storage, magnetic cassettes, magnetic tapes, magnetic disk storage or other magnetic storage devices, or any other medium which may be used to store the desired information and which may be accessed by the devices. Combinations of any of the above should also be included within the scope of computer-readable media.

The FCC process controller 24 may also include one or more communication connection(s) 1508 that may facilitate a control device (not shown) to communicate with devices or equipment capable of communicating with the FCC process controller 24. The FCC process controller 24 may also include a computer system (not shown). Connections may also be established via various data communication channels or ports, such as USB or COM ports to receive cables connecting the FCC process controller 24 to various other devices on a network. In some examples, the FCC process controller 24 may include Ethernet drivers that enable the FCC process controller 24 to communicate with other devices on the network. According to various examples, communication connections 1508 may be established via a wired and/or wireless connection on the network.

The FCC process controller 24 may also include one or more input devices 1510, such as a keyboard, mouse, pen, voice input device, gesture input device, and/or touch input device. It may further include one or more output devices 1512, such as a display, printer, and/or speakers. In some examples, computer-readable communication media may include computer-readable instructions, program modules, or other data transmitted within a data signal, such as a carrier wave or other transmission. As used herein, however, computer-readable storage media may not include computer-readable communication media.

Turning to the contents of the memory 1502, the memory 1502 may include, but is not limited to, an operating system (OS) 1514 and one or more application programs or services for implementing the features and embodiments disclosed herein. Such applications or services may include remote terminal units 1516 for executing certain systems and methods for controlling operation of the FCC processing assembly 10 (e.g., semi- or fully-autonomously controlling operation of the FCC processing assembly 10), for example, upon receipt of one or more control signals generated by the FCC process controller 24. In some embodiments, one or more remote terminal unit(s) 1516 may be located in the vicinity of the FCC processing assembly 10. The remote terminal unit(s) 1516 may reside in the memory 1502 or may be independent of the FCC process controller 24. In some examples, the remote terminal unit(s) 1516 may be implemented by software that may be provided in configurable control block language and may be stored in non-volatile memory. When executed by the processor(s) 1500, the remote terminal unit(s) 1516 may implement the various functionalities and features associated with the FCC process controller 24 described herein.

As desired, embodiments of the disclosure may include an FCC process controller 24 with more or fewer components than are illustrated in FIG. 15. Additionally, certain components of the example FCC process controller 24 shown in FIG. 15 may be combined in various embodiments of the disclosure. The FCC process controller 24 of FIG. 15 is provided by way of example only.

References are made to block diagrams of systems, methods, apparatuses, and computer program products according to example embodiments. It will be understood that at least some of the blocks of the block diagrams, and combinations of blocks in the block diagrams, may be implemented at least partially by computer program instructions. These computer program instructions may be loaded onto a general purpose computer, special purpose computer, special purpose hardware-based computer, or other programmable data processing apparatus to produce a machine, such that the instructions which execute on the computer or other programmable data processing apparatus create means for implementing the functionality of at least some of the blocks of the block diagrams, or combinations of blocks in the block diagrams discussed.

These computer program instructions may also be stored in a non-transitory computer-readable memory that can direct a computer or other programmable data processing apparatus to function in a particular manner, such that the instructions stored in the computer-readable memory produce an article of manufacture including instruction means that implement the function specified in the block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide task, acts, actions, or operations for implementing the functions specified in the block or blocks.

One or more components of the systems and one or more elements of the methods described herein may be implemented through an application program running on an operating system of a computer. They may also be practiced with other computer system configurations, including handheld devices, multiprocessor systems, microprocessor-based or programmable consumer electronics, mini-computers, mainframe computers, and the like.

Application programs that are components of the systems and methods described herein may include routines, programs, components, data structures, etc. that may implement certain abstract data types and perform certain tasks or actions. In a distributed computing environment, the application program (in whole or in part) may be located in local memory or in other storage. In addition, or alternatively, the application program (in whole or in part) may be located in remote memory or in storage to allow for circumstances where tasks can be performed by remote processing devices linked through a communications network.

This application is a continuation of U.S. Non-Provisional patent application Ser. No. 18/052,780, filed Nov. 4, 2022, titled "ASSEMBLIES AND METHODS FOR ENHANCING FLUID CATALYTIC CRACKING (FCC) PROCESSES DURING THE FCC PROCESS USING SPECTROSCOPIC ANALYZERS," which is a continuation-in-part of U.S. Non-Provisional application Ser. No. 17/652,431, filed Feb. 24, 2022, titled "METHODS AND ASSEMBLIES FOR DETERMINING AND USING STANDARDIZED SPECTRAL RESPONSES FOR CALIBRATION OF SPECTROSCOPIC ANALYZERS," which claims priority to and the benefit of U.S. Provisional Application No. 63/153,452, filed Feb. 25, 2021, titled "METHODS AND ASSEMBLIES FOR DETERMINING AND USING STANDARDIZED SPECTRAL RESPONSES FOR CALIBRATION OF SPECTROSCOPIC ANALYZERS," and U.S. Provisional Application No. 63/268,456, filed Feb. 24, 2022, titled "ASSEMBLIES AND METHODS FOR ENHANCING CONTROL OF FLUID CATALYTIC CRACKING (FCC) PROCESSES USING SPECTROSCOPIC ANALYZERS," the disclosures of which are incorporated herein by reference in their entireties; and further claims priority to and the benefit of U.S. Provisional Application No. 63/268,456, filed Feb. 24, 2022, titled "ASSEMBLIES AND METHODS FOR ENHANCING CONTROL OF FLUID CATALYTIC CRACKING (FCC) PROCESSES USING SPECTROSCOPIC ANALYZERS"; U.S. Provisional Application No. 63/268,827, filed Mar. 3, 2022, titled "ASSEMBLIES AND METHODS FOR OPTIMIZING FLUID CATALYTIC CRACKING (FCC) PROCESSES DURING THE FCC PROCESS USING SPECTROSCOPIC ANALYZERS"; and U.S. Provisional Application No. 63/268,875, filed Mar. 4, 2022, titled "ASSEMBLIES AND METHODS FOR ENHANCING CONTROL OF HYDROTREATING AND FLUID CATALYTIC CRACKING (FCC) PROCESSES USING SPECTROSCOPIC ANALYZERS," the disclosures of all three of which are incorporated herein by reference in their entireties.

Having now described some illustrative embodiments of the disclosure, it should be apparent to those skilled in the art that the foregoing is merely illustrative and not limiting, having been presented by way of example only. Numerous modifications and other embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives. Those skilled in the art should appreciate that the parameters and configurations described herein are exemplary and that actual parameters and/or configurations will depend on the specific application in which the systems, methods, and/or aspects or techniques of the disclosure are used. Those skilled in the art should also recognize or be able to ascertain, using no more than routine experimentation, equivalents to the specific embodiments of the disclosure. It is, therefore, to be understood that the embodiments described herein are presented by way of example only and that, within the scope of any appended claims and equivalents thereto, the disclosure may be practiced other than as specifically described.

Furthermore, the scope of the present disclosure shall be construed to cover various modifications, combinations, additions, alterations, etc., above and to the above-described embodiments, which shall be considered to be within the scope of this disclosure. Accordingly, various features and characteristics as discussed herein may be selectively interchanged and applied to other illustrated and non-illustrated embodiment, and numerous variations, modifications, and additions further may be made thereto without departing from the spirit and scope of the present disclosure as set forth in the appended claims.

What is claimed is:

1. A method to enhance a fluid catalytic cracking (FCC) process associated with a refining operation, during the FCC process, the method comprising:

supplying a hydrocarbon feedstock to one or more first processing units associated with the refining operation, the hydrocarbon feedstock having one or more hydrocarbon feedstock parameters and the one or more first processing units comprising an FCC processing unit;

operating the one or more first processing units, thereby to produce one or more corresponding unit materials, the one or more corresponding unit materials comprising one or more of intermediate materials or unit product materials comprising FCC effluent;

analyzing a hydrocarbon feedstock sample of the hydrocarbon feedstock via a first spectroscopic analyzer, thereby to provide hydrocarbon feedstock sample spectra;

analyzing a unit material sample of the one or more corresponding unit materials via one or more of the first spectroscopic analyzer or a second spectroscopic analyzer, thereby to provide unit material sample spectra, the one or more of the first spectroscopic analyzer or the second spectroscopic analyzer calibrated to generate standardized spectral responses;
predicting one or more hydrocarbon feedstock sample properties associated with the hydrocarbon feedstock sample based at least in part on the hydrocarbon feedstock sample spectra;
predicting one or more unit material sample properties associated with the unit material sample based at least in part on the unit material sample spectra; and
prescriptively controlling, during the FCC process, via one or more FCC process controllers based at least in part on the one or more hydrocarbon feedstock parameters, the one or more hydrocarbon feedstock sample properties, and the one or more unit material sample properties, one or more of:
 (i) the one or more hydrocarbon feedstock parameters associated with the hydrocarbon feedstock supplied to the one or more first processing units,
 (ii) one or more intermediates properties associated with the intermediate materials produced by one or more of the first processing units,
 (iii) operation of the one or more first processing units, one or more unit materials properties associated with the one or more unit materials, or
 (iv) operation of one or more second processing units positioned downstream relative to the one or more first processing units,
so that the prescriptively controlling during the FCC process causes the FCC process to produce one or more of:
  (a) one or more intermediate materials each having one or more properties within a selected range of one or more target properties of the one or more intermediate materials,
  (b) one or more unit materials each having one or more properties within a selected range of one or more target properties of the one or more unit materials, or
  (c) one or more downstream materials each having one or more properties within a selected range of one or more target properties of the one or more downstream materials,
   thereby to cause the FCC process to achieve material outputs that more accurately and responsively converge on one or more of the target properties.

2. The method of claim 1, the method further comprising one or more of:
 (i) conditioning a hydrocarbon feedstock sample to one or more of filter the hydrocarbon feedstock sample, change a temperature of the hydrocarbon feedstock sample, or degas the hydrocarbon feedstock sample; or
 (ii) conditioning a unit material sample to one or more of filter the unit material sample, change a temperature of the unit material sample, dilute the unit material sample in solvent, or degas the unit material sample, and
 wherein one or more of:
 (i) the conditioning the hydrocarbon feedstock sample comprises directing the hydrocarbon feedstock sample to a sample conditioning assembly configured to one or more of:
  (a) control a sample temperature of the hydrocarbon feedstock sample to maintain a hydrocarbon feedstock sample temperature within a first preselected temperature range,
  (b) remove particulates from the hydrocarbon feedstock sample, or
  (c) degas the hydrocarbon feedstock sample, or
 (ii) conditioning the unit material sample comprises directing the unit material sample to a sample conditioning assembly configured to one or more of:
  (a) control a unit material sample temperature of the unit material sample, thereby to maintain a unit material sample temperature within a second preselected temperature range,
  (b) remove particulates from the unit sample material,
  (c) dilute the unit material sample in solvent, or
  (d) degas the unit material sample.

3. The method of claim 1, wherein
the analyzing the unit material sample via one or more of the first spectroscopic analyzer or the second spectroscopic analyzer comprises analyzing the unit material sample via the second spectroscopic analyzer, and wherein
the second spectroscopic analyzer generates spectral responses standardized with respect to the first spectroscopic analyzer.

4. The method of claim 3, wherein the first spectroscopic analyzer and the second spectroscopic analyzer generate standardized spectral responses such that each of the first spectroscopic analyzer and the second spectroscopic analyzer output a respective corrected material spectrum, including a plurality of signals indicative of a plurality of material properties of an analyzed material based at least in part on the corrected material spectrum, and such that the plurality of material properties of the analyzed material outputted by the first spectroscopic analyzer is substantially consistent with a plurality of material properties of the analyzed material outputted by the second spectroscopic analyzer.

5. The method of claim 1, wherein:
the FCC processing unit comprises a reactor positioned to receive the hydrocarbon feedstock and a catalyst, thereby to promote catalytic cracking of the hydrocarbon feedstock into the FCC effluent, and
the method further comprises analyzing, via one or more of the first spectroscopic analyzer or the second spectroscopic analyzer, the FCC effluent at an outlet of the reactor.

6. The method of claim 1, wherein prescriptively controlling operation of the one or more first processing units comprises controlling one or more operating parameters of the one or more first processing units, wherein the one or more feedstock parameters associated with the hydrocarbon feedstock supplied to the one or more first processing units comprises one or more of API gravity, UOP K factor, distillation points, coker gas oil content, carbon residue content, nitrogen content, sulfur content, catalyst oil ratio, saturates content, thiophene content, single-ring aromatics content, dual-ring aromatics content, triple-ring aromatics content, or quad-ring aromatics content, and wherein the one or more hydrocarbon feedstock sample properties and the one or more unit material sample properties comprises a content ratio indicative of relative amounts of one or more hydrocarbon classes present in one or more of the hydrocarbon feedstock sample or the unit material sample.

7. The method of claim 6, wherein controlling the one or more operating parameters of the one or more first processing units comprises controlling the one or more operating parameters against operating constraints associated with the one or more first processing units.

8. The method of claim 1, wherein the FCC processing unit comprises a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and the method further comprises analyzing, via one or more spectroscopic analyzers, a reaction mixture sample taken from one or more locations of the reactor, the one or more spectroscopic analyzers calibrated, so as to generate standardized spectral responses.

9. The method of claim 8, wherein the analyzing the reaction mixture sample taken from the one or more locations of the reactor comprises analyzing the reaction mixture sample taken from the one or more locations of the reactor via respective spectroscopic analyzers, the respective spectroscopic analyzers calibrated so as to generate standardized spectral responses.

10. The method of claim 8, wherein the FCC processing unit comprises a riser associated with the reactor, and the method further comprises analyzing, via one of more spectroscopic analyzers, two or more reaction mixture samples taken from two or more different points along a height of the riser, the one or more spectroscopic analyzers calibrated so as to generate standardized spectral responses.

11. The method of claim 8, wherein the FCC processing unit comprises a riser associated with the reactor, and the method further comprises analyzing, via the second spectroscopic analyzer, a reaction mixture sample at an outlet of the riser.

12. The method of claim 1, wherein:
the FCC processing unit comprises:
   a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and
   a riser associated with the reactor, and
the method further comprises:
   analyzing, via a spectroscopic analyzer, a reaction mixture sample at an outlet of the riser; and
   analyzing, via the second spectroscopic analyzer, the FCC effluent at an outlet of the reactor, the analyzing the reaction mixture sample at the outlet of the riser and the analyzing the FCC effluent at the outlet of the reactor occurring substantially concurrently.

13. The method of claim 1, wherein the FCC processing unit comprises a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and the method further comprises analyzing, via one or more spectroscopic analyzers, two or more reaction mixture samples taken from two or more different locations of a cross section of the riser, the one or more spectroscopic analyzers calibrated so as to generate standardized spectral responses.

14. The method of claim 1, wherein:
the FCC processing unit comprises:
   a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and
   a catalyst stripper bed associated with the reactor and positioned to receive at least a portion of the catalyst after the catalytic cracking, and
the method further comprises analyzing, via one or more spectroscopic analyzers, the at least a portion of the catalyst.

15. The method of claim 1, wherein the prescriptively controlling comprises controlling one or more process parameters, the one or more process parameters comprising one or more of:
   (i) the one or more hydrocarbon feedstock parameters associated with the hydrocarbon feedstock,
   (ii) a rate of supply of the hydrocarbon feedstock to the one or more first processing units,
   (iii) a pressure of the hydrocarbon feedstock supplied to the one or more first processing units,
   (iv) a preheating temperature of the hydrocarbon feedstock supplied to the one or more first processing units,
   (v) a reactor temperature in a reactor of the one or more first processing units,
   (vi) a reactor pressure associated with a reaction mixture in the reactor, the reaction mixture comprising the hydrocarbon feedstock and a catalyst to promote catalytic cracking the hydrocarbon feedstock,
   (vii) the one or more unit materials properties associated with the one or more unit materials produced by the one or more first processing units, or
   (viii) one or more downstream properties associated with the one or more downstream materials produced by the one or more second processing units.

16. The method of claim 1, wherein the one or more unit materials properties associated with the one or more unit materials comprises one or more of an amount of butane free gasoline, an amount of total butane, an amount of dry gas, an amount of coke, an amount of gasoline, octane rating, an amount of light fuel oil, an amount of heavy fuel oil, an amount of hydrogen sulfide, an amount of sulfur in light fuel oil, or an aniline point of light fuel oil, wherein the analyzing the unit material sample comprises analyzing the unit material sample via a second spectroscopic analyzer, and wherein one or more of the first spectroscopic analyzer or the second spectroscopic analyzer comprises: one or more of (a) one or more near-infrared (NIR) spectroscopic analyzers, (b) one or more mid-infrared (mid-IR) spectroscopic analyzers, (c) one or more combined NIR and mid-IR spectroscopic analyzers, (d) or one or more Raman spectroscopic analyzers.

17. The method of claim 1, wherein the prescriptively controlling comprises operating an analytical cracking model configured to improve an accuracy of one or more of:
   (i) predicting the one or more hydrocarbon feedstock parameters,
   (ii) predicting the one or more intermediates properties associated with the intermediate materials produced by the one or more first processing units,
   (iii) controlling the one or more hydrocarbon feedstock parameters of the hydrocarbon feedstock supplied to the one or more first processing units,
   (iv) controlling the one or more properties associated with the intermediate materials produced by the one or more first processing units,
   (v) controlling the one or more effluent properties associated with FCC effluent produced by the one or more first processing units,
   (vi) the one or more target properties of the unit materials produced by one or more of the first processing units, or
   (vii) the one or more target properties of the downstream materials produced by one or more of the second processing units.

18. The method of claim 17, wherein the analytical cracking model comprises a machine-learning-trained model, and the method further comprises:
(a) supplying, to the analytical cracking model, catalytic cracking processing data related to one or more of:
  (i) material data comprising one or more of:
   feedstock data indicative of one or more hydrocarbon feedstock properties associated with the hydrocarbon feedstock,
   unit material data indicative of one or more unit material properties associated with the one or more unit materials, or
   downstream material data indicative of one or more downstream material properties associated with one or more downstream materials produced by the one or more second processing units, or
  (ii) processing assembly data comprising one or more of:
   first processing unit data indicative of one or more operating parameters associated with operation of the one or more first processing units,
   second processing unit data indicative of one or more operating parameters associated with operation of the one or more second processing units, or
   conditioning assembly data indicative of operation of a sample conditioning assembly configured to one or more of control a sample temperature of a material sample, remove particulates from the material sample, dilute the material sample in solvent, or degas the material sample; and
(b) prescriptively controlling, based at least in part on the catalytic cracking processing data, one or more of:
  (i) one or more hydrocarbon feedstock parameters associated with the hydrocarbon feedstock,
  (ii) one or more first operating parameters associated with operation of the one or more first processing units,
  (iii) the one or more unit material properties associated with the one or more unit materials,
  (iv) the one or more intermediates properties associated with the one or more intermediate materials,
  (v) one or more second operating parameters associated with operation of the one or more second processing units positioned downstream relative to the one or more first processing units,
  (vi) one or more downstream properties associated with the one or more downstream materials produced by the one or more second processing units, or
  (vii) one or more sample conditioning assembly operating parameters associated with operation of a sample conditioning assembly.

19. The method of claim 18, further comprising updating the analytical cracking model based at least in part on catalytic cracking processing data, and wherein the analytical cracking model comprises one or more cracking algorithms configured to:
(i) determine, based at least in part on the catalytic cracking data, one or more target properties of the hydrocarbon feedstock, the one or more target properties of the one or more unit materials, or the one or more target properties of the one or more downstream materials,
(ii) prescriptively control operation of one or more of the first processing units or the one or more second processing units, thereby to produce one or more of unit materials having unit material properties within a first predetermined range of target unit material properties for the unit materials or one or more of downstream materials having downstream material properties within a second predetermined range of target material properties for the downstream materials,
(iii) determine one or more of actual unit material properties for the unit materials produced by the one or more first processing units or one or more of actual downstream material properties for the downstream materials produced by the one or more second processing units,
(iv) determine one or more of unit material differences between the actual unit material properties and the target unit material properties or downstream material differences between the actual downstream material properties and the target downstream material properties, and
(v) change, based at least in part on one or more of the unit material differences or the downstream material differences, the one or more cracking algorithms, thereby to reduce the one or more of the unit material differences or the downstream material differences.

20. The method of claim 19, wherein the prescriptively controlling further comprises one or more of:
(i) generating, based at least in part on the target unit material properties, a first processing unit control signal configured to control at least one first processing parameter associated with operation of the one or more first processing units to produce one or more unit materials having unit material properties within the first preselected range of the target unit material properties, or
(ii) generating, based at least in part on the target downstream material properties, a second processing unit control signal configured to control at least one second processing parameter associated with operation of the one or more second processing units to produce one or more downstream materials having downstream material properties within the second preselected range of the target downstream material properties.

21. The method of claim 1, wherein one or more of:
(i) predicting the one or more hydrocarbon feedstock sample properties comprises mathematically manipulating a feedstock spectra signal indicative of the hydrocarbon feedstock sample spectra, thereby to provide a manipulated feedstock signal and communicating the manipulated feedstock signal an analytical property model configured to predict, based at least in part on the manipulated feedstock signal, the one or more hydrocarbon feedstock sample properties, or
(ii) predicting the one or more unit material sample properties comprises mathematically manipulating a unit material spectra signal indicative of the unit material sample spectra, thereby to provide a manipulated unit material signal and communicating the manipulated unit material signal to an analytical property model configured to predict, based at least in part on the manipulated unit material signal, the one or more unit material sample properties.

22. The method of claim 1, wherein the FCC processing unit comprises a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and the method further comprises analyzing, via one or more spectroscopic analyzers, reaction mixture samples taken from one or more locations of the reactor, thereby to obtain unit material samples of one or more of catalyst stripper vapor, reactor dilute vapor, riser vapor, or reactor effluent to determine one or more of respective catalyst stripper vapor yield, reactor dilute vapor yield, riser vapor yield, or reactor effluent yield.

23. A fluid catalytic cracking (FCC) control assembly to enhance a fluid catalytic cracking (FCC) process associated with a refining operation, during the FCC process, the FCC control assembly comprising:
(i) a first spectroscopic analyzer positioned to:
receive on-line a hydrocarbon feedstock sample of a hydrocarbon feedstock positioned to be supplied to one or more first processing units associated with the refining operation, the hydrocarbon feedstock having one or more hydrocarbon feedstock parameters and the one or more first processing units comprising an FCC processing unit, and
analyze the hydrocarbon feedstock sample, thereby to provide hydrocarbon feedstock sample spectra;
(ii) a second spectroscopic analyzer positioned to:
receive on-line a unit material sample of one more unit materials produced by the one or more first processing units, the one or more unit materials comprising one or more of intermediate materials or unit product materials comprising FCC effluent, the first spectroscopic analyzer and the second spectroscopic analyzer calibrated so as to generate standardized spectral responses, and
analyze the unit material sample to provide unit material sample spectra; and
(iii) an FCC process controller in communication with the first spectroscopic analyzer and the second spectroscopic analyzer, the FCC process controller configured to:
predict one or more hydrocarbon feedstock sample properties associated with the hydrocarbon feedstock sample based at least in part on the hydrocarbon feedstock sample spectra,
predict one or more unit material sample properties associated with the unit material sample based at least in part on the unit material sample spectra, and
prescriptively control, during the FCC process, based at least in part on the one or more hydrocarbon feedstock parameters, the one or more hydrocarbon feedstock sample properties, and the one or more unit material sample properties, one or more of:
(a) the one or more hydrocarbon feedstock parameters associated with the hydrocarbon feedstock supplied to the one or more first processing units,
(b) one or more intermediates properties associated with the intermediate materials produced by one or more of the first processing units,
(c) operation of the one or more first processing units,
(d) one or more unit materials properties associated with the one or more unit materials, or
(e) operation of one or more second processing units positioned downstream relative to the one or more first processing units,
so that the prescriptively controlling during the FCC process causes the FCC process to produce one or more of:
(aa) one or more intermediate materials each having one or more properties within a selected range of one or more target properties of the one or more intermediate materials,
(bb) one or more unit materials each having one or more properties within a selected range of one or more target properties of the one or more unit materials, or
(cc) one or more downstream materials each having one or more properties within a selected range of one or more target properties of the one or more downstream materials,
thereby to cause the FCC process to achieve material outputs that more accurately and responsively converge on one or more of the target properties.

24. The FCC control assembly of claim 23, further comprising a sample conditioning assembly positioned to one or more of:
(i) condition the hydrocarbon feedstock sample, prior to supply to the first spectroscopic analyzer, to one or more of filter the hydrocarbon feedstock sample, change a temperature of the hydrocarbon feedstock sample, or degas the hydrocarbon feedstock sample, or
(ii) condition the unit material sample, prior to supply to the second spectroscopic analyzer, to one or more of (a) filter the unit material sample, (b) change a temperature of the unit material sample, (c) dilute the unit material sample in solvent, or (d) degas the unit material sample, and
wherein the sample conditioning assembly comprises one or more of:
(i) one or more filters comprising filter media positioned to remove one or more of water, particulates, or other contaminants from one or more of the hydrocarbon feedstock sample or the unit material sample,
(ii) a temperature control unit positioned to receive the one or more of the hydrocarbon feedstock sample or the unit material sample and a temperature of the one or more of the hydrocarbon feedstock sample or the unit material sample to provide a temperature-adjusted sample stream of the one or more of the hydrocarbon feedstock sample or the unit material sample, or
(iii) a degassing unit positioned to degas the one or more of the hydrocarbon feedstock sample or the unit material sample to provide a degassed sample stream of the one or more of the hydrocarbon feedstock sample or the unit material sample.

25. The FCC control assembly of claim 23, wherein the first spectroscopic analyzer and the second spectroscopic analyzer generate standardized spectral responses such that each of the first spectroscopic analyzer and the second spectroscopic analyzer output a respective corrected material spectrum, including a plurality of signals indicative of a plurality of material properties of an analyzed material based at least in part on the corrected material spectrum, and such that the plurality of material properties of the analyzed material outputted by the first spectroscopic analyzer are substantially consistent with a plurality of material properties of the analyzed material outputted by the second spectroscopic analyzer.

26. The FCC control assembly of claim 25, wherein the FCC processing unit comprises a reactor positioned to receive the hydrocarbon feedstock and a catalyst, thereby to promote catalytic cracking of the hydrocarbon feedstock into the FCC effluent, wherein the second spectroscopic analyzer is configured to analyze the FCC effluent at an outlet of the reactor, wherein the FCC process controller is configured to prescriptively control during the FCC process control one or more operating parameters of the one or more first processing units, and wherein the FCC process controller is configured to prescriptively control, during the FCC process control, one or more operating parameters of the one or more first processing units against operating constraints associated with the one or more first processing units.

27. The FCC control assembly of claim 23, wherein the FCC processing unit comprises a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and wherein one or more of (i) the second spectroscopic analyzer or (ii) one or more additional spectroscopic analyzers, is configured to analyze a reaction mixture sample taken from one or more locations of the reactor.

28. The FCC control assembly of claim 23, wherein
the FCC processing unit comprises:
    a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and
    a riser associated with the reactor,
wherein the FCC control assembly comprising a spectroscopic analyzer configured to analyze a reaction mixture sample at an outlet of the riser, and
wherein the second spectroscopic analyzer is configured to analyze the FCC effluent at an outlet of the reactor, the reaction mixture sample at the outlet of the riser and the FCC effluent at the outlet of the reactor analyzed substantially during concurrent periods of time.

29. The FCC control assembly of claim 23, wherein:
the FCC processing unit comprises a reactor positioned to receive the hydrocarbon feedstock and a catalyst to promote catalytic cracking of the hydrocarbon feedstock into the FCC effluent, the hydrocarbon feedstock and the catalyst providing a reaction mixture, and
the FCC control assembly comprises one or more spectroscopic analyzers configured to analyze two or more reaction mixture samples taken from two or more different locations of a cross section of the riser, the one or more spectroscopic analyzers being calibrated to generate standardized spectral responses.

30. The FCC control assembly of claim 23, wherein the FCC processing unit comprises:
    a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and
    a riser associated with the reactor, and
    the FCC control assembly further comprises a third spectroscopic analyzer, one or more of the second spectroscopic analyzer or the third spectroscopic analyzer configured to analyze a reaction mixture sample taken from an inlet of the riser.

31. The FCC control assembly of claim 23, wherein the FCC processing unit comprises:
    a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and
    a catalyst stripper bed associated with the reactor and positioned to receive at least a portion of the catalyst after the catalytic cracking, and wherein one of the first spectroscopic analyzer, the second spectroscopic analyzer, or an additional spectroscopic analyzer is configured to analyze the at least a portion of the catalyst.

32. The FCC control assembly of claim 23, wherein the prescriptively control comprises control one or more process parameters, the one or more process parameters comprising one or more of:
    (i) the one or more hydrocarbon feedstock parameters,
    (ii) a rate of supply of the hydrocarbon feedstock to the one or more first processing units,
    (iii) a pressure of the hydrocarbon feedstock supplied to the one or more first processing units,
    (iv) a preheating temperature of the hydrocarbon feedstock supplied to the one or more first processing units,
    (v) a reactor temperature in a reactor of the one or more first processing units,
    (vi) a reactor pressure associated with a reaction mixture in the reactor, the reaction mixture comprising the hydrocarbon feedstock and a catalyst, thereby to promote catalytic cracking of the hydrocarbon feedstock,
    (vii) the one or more unit materials properties associated with the one or more unit materials produced by the one or more first processing units, or
    (viii) one or more downstream properties associated with the one or more downstream materials produced by the one or more second processing units.

33. The FCC control assembly of claim 23, wherein the feedstock parameter associated with the hydrocarbon feedstock supplied to the one or more first processing units comprises one or more of API gravity, UOP K factor, distillation pints, coker gas oil content, carbon residue content, nitrogen content, sulfur content, catalyst oil ratio, saturates content, thiophene content, single-ring aromatics content, dual-ring aromatics content, triple-ring aromatics content, or quad-ring aromatics content, wherein the one or more hydrocarbon feedstock sample properties and the one or more unit material sample properties comprise a content ratio indicative of relative amounts of one or more hydrocarbon classes present in one or more of the hydrocarbon feedstock sample or the unit material sample, and wherein the one or more unit materials properties associated with the one or more unit materials comprises one or more of an amount of butane free gasoline, an amount of total butane, an amount of dry gas, an amount of coke, an amount of gasoline, octane rating, an amount of light fuel oil, an amount of heavy fuel oil, an amount of hydrogen sulfide, an amount of sulfur in light fuel oil, or an aniline point of light fuel oil.

34. The FCC control assembly of claim 23, wherein one or more of the first spectroscopic analyzer or the second spectroscopic analyzer comprises one or more of one or more near-infrared (NIR) spectroscopic analyzers, one or more mid-infrared (mid-IR) spectroscopic analyzers, one or more combined NIR and mid-IR spectroscopic analyzers, or one or more Raman spectroscopic analyzers.

35. The FCC control assembly of claim 23, wherein the prescriptively control comprises operate an analytical cracking model configured to improve an accuracy of one or more of:
    (i) predicting the one or more hydrocarbon feedstock parameters,
    (ii) predicting the one or more intermediates properties associated with the intermediate materials produced by the one or more first processing units, (iii) controlling the one or more hydrocarbon feedstock parameters of the hydrocarbon feedstock supplied to the one or more first processing units, (iv) controlling the one or more properties associated with the intermediate materials produced by the one or more first processing units, (v) controlling one or more effluent properties associated with the FCC effluent produced by the one or more first processing units, (vi) the one or more target properties of the unit materials produced by one or more of the first processing units, or (vii) the one or more target properties of the downstream materials produced by one or more of the second processing units.

36. The FCC control assembly of claim 35, wherein the analytical cracking model comprises a machine-learning-trained model, and wherein the FCC process controller further is configured to:

(a) provide, to the analytical cracking model, catalytic cracking processing data related to one or more of:
  (i) material data comprising one or more of:
    feedstock data indicative of the one or more hydrocarbon feedstock properties associated with the hydrocarbon feedstock,
    unit material data indicative of the one or more unit material properties associated with the one or more unit materials, or
    downstream material data indicative of one or more downstream material properties associated with one or more downstream materials produced by the one or more second processing units, or
  (ii) processing assembly data comprising one or more of:
    first processing unit data indicative of one or more operating parameters associated with operation of the one or more first processing units,
    second processing unit data indicative of one or more operating parameters associated with operation of the one or more second processing units, or
    conditioning assembly data indicative of operation of a sample conditioning assembly configured to one or more of control a sample temperature of a material sample, remove particulates from the material sample, dilute the material sample in solvent, or degas the material sample, and (b) prescriptively control, based at least in part on the catalytic cracking processing data, one or more of:
  (i) the one or more hydrocarbon feedstock parameters associated with the hydrocarbon feedstock,
  (ii) one or more first operating parameters associated with operation of the one or more first processing units,
  (iii) the one or more properties associated with the one or more unit materials,
  (iv) the one or more properties associated with the one or more unit materials,
  (v) one or more second operating parameters associated with operation of the one or more second processing units positioned downstream relative to the one or more first processing units,
  (vi) one or more properties associated with the one or more downstream materials produced by the one or more second processing units,
  (vii) the one or more downstream material properties associated with the one or more downstream materials, or
  (viii) one or more sample conditioning assembly operating parameters associated with operation of the sample conditioning assembly.

37. The FCC control assembly of claim 36, wherein the FCC process controller further is configured to update the analytical cracking model based at least in part on the catalytic cracking processing data, and wherein the analytical cracking model comprises one or more cracking algorithms configured to:

(i) determine, based at least in part on the catalytic cracking data, target material properties for one or more of the hydrocarbon feedstock, the unit materials, or the downstream materials, (ii) prescriptively control operation of one or more of the first processing units or the one or more second processing units, thereby to produce one or more of unit materials having unit material properties within a first predetermined range of target unit material properties for the unit materials or one or more of downstream materials having downstream material properties within a second predetermined range of target material properties for the downstream materials, (iii) determine one or more of actual unit material properties for the unit materials produced by the one or more first processing units or one or more of actual downstream material properties for the downstream materials produced by the one or more second processing units, (iv) determine one or more of unit material differences between the actual unit material properties and the target unit material properties or downstream material differences between the actual downstream material properties and the target downstream material properties, and (v) change, based at least in part on one or more of the unit material differences or the downstream material differences, the one or more cracking algorithms, thereby to reduce the one or more of the unit material differences or the downstream material differences.

38. The FCC control assembly of claim 37, wherein the prescriptively control further comprises one or more of:

(i) generate, based at least in part on the target unit material properties, a first processing unit control signal configured to control at least one first processing parameter associated with operation of the one or more first processing units, thereby to produce one or more unit materials having unit material properties within the first preselected range of the target unit material properties, or (ii) generate, based at least in part on the target downstream material properties, a second processing unit control signal configured to control at least one second processing parameter associated with operation of the one or more second processing units, thereby to produce one or more downstream materials having downstream material properties within the second preselected range of the target downstream material properties.

39. The FCC control assembly of claim 23, wherein one or more of:

(i) predicting the one or more hydrocarbon feedstock sample properties comprises mathematically manipulating a feedstock spectra signal indicative of the hydrocarbon feedstock sample spectra to provide a manipulated feedstock signal and communicating the manipulated feedstock signal an analytical property model configured to predict, based at least in part on the manipulated feedstock signal, the one or more hydrocarbon feedstock sample properties, or (ii) predicting the one or more unit material sample properties comprises mathematically manipulating a unit material spectra signal indicative of the unit material sample spectra, thereby to provide a manipulated unit material signal and communicating the manipulated unit material signal to an analytical property model configured, so as to predict, based at least in part on the manipulated unit material signal, the one or more unit material sample properties.

40. The FCC control assembly of claim 39, wherein the prescriptively control comprises generate, based at least in part on one or more of the one or more hydrocarbon feedstock sample properties or the one or more unit material sample properties, one or more processing unit control signals configured to control on-line one or more processing parameters related to operation of one or more of the one more first processing units or one or more of the second processing unit, wherein the one or more unit sample properties comprises reaction effluent yield, wherein the prescriptively control further comprises controlling one or more of:
  (a) riser outlet temperature based at least in part on the reaction effluent yield, or
  (b) riser lift velocity based at least in part on the reaction effluent yield, and wherein the one or more unit material sample properties comprises FCC product yield, and the prescriptively controlling comprises controlling riser lift steam rate based at least in part on the FCC product yield.

41. The FCC control assembly of claim 23, wherein:
the FCC processing unit comprises a reactor positioned to receive the hydrocarbon feedstock and a catalyst, thereby to promote catalytic cracking of the hydrocarbon feedstock into the FCC effluent, the hydrocarbon feedstock and the catalyst providing a reaction mixture, and
the FCC control assembly comprises one or more spectroscopic analyzers configured to analyze reaction mixture samples taken from one or more locations of the reactor to obtain unit material samples of one or more of catalyst stripper vapor, reactor dilute vapor, riser vapor, or reactor effluent, thereby to determine one or more of respective catalyst stripper vapor yield, reactor dilute vapor yield, riser vapor yield, or reactor effluent yield.

42. A fluid catalytic cracking (FCC) processing assembly for performing an FCC process associated with a refining operation, the FCC processing assembly comprising:
  (i) one or more first FCC processing units associated with the refining operation including one or more of an FCC reactor or an FCC regenerator;
  (ii) a first spectroscopic analyzer positioned to:
    receive on-line during the FCC process a hydrocarbon feedstock sample of a hydrocarbon feedstock, the hydrocarbon feedstock having one or more hydrocarbon feedstock parameters and supplied to the one or more first FCC processing units, and
    analyze during the FCC process the hydrocarbon feedstock sample, thereby to provide hydrocarbon feedstock sample spectra;
  (iii) a second spectroscopic analyzer positioned to:
    receive on-line during the FCC process a unit material sample of one more unit materials produced by the one or more first FCC processing units, the one or more unit materials comprising one or more of intermediate materials or unit product materials comprising FCC effluent, the first spectroscopic analyzer and the second spectroscopic analyzer generating standardized spectral responses, and
    analyze during the FCC process the unit material sample to provide unit material sample spectra; and
  (iv) an FCC process controller in communication with the first spectroscopic analyzer and the second spectroscopic analyzer during the FCC process, the FCC process controller configured to:
    (a) predict during the FCC process one or more hydrocarbon feedstock sample properties associated with the hydrocarbon feedstock sample based at least in part on the hydrocarbon feedstock sample spectra,
    (b) predict during the FCC process one or more unit material sample properties associated with the unit material sample based at least in part on the unit material sample spectra, and
    (c) prescriptively control, during the FCC process, based at least in part on the one or more hydrocarbon feedstock parameters, the one or more hydrocarbon feedstock sample properties, and the one or more unit material sample properties, one or more of:
      (aa) the one or more hydrocarbon feedstock parameters associated with the hydrocarbon feedstock supplied to the one or more first FCC processing units,
      (bb) one or more intermediates properties associated with the intermediate materials produced by one or more of the first FCC processing units,
      (cc) operation of the one or more first FCC processing units,
      (dd) one or more unit materials properties associated with the one or more unit materials, or
      (ee) operation of one or more second processing units positioned downstream relative to the one or more first FCC processing units,
    so that the prescriptively controlling during the FCC process causes the FCC process to produce one or more of:
      (1) one or more intermediate materials each having one or more properties within a selected range of one or more target properties of the one or more intermediate materials,
      (2) one or more unit materials each having one or more properties within a selected range of one or more target properties of the one or more unit materials, or
      (3) one or more downstream materials each having one or more properties within a selected range of one or more target properties of the one or more downstream materials,
    thereby to cause the FCC process to achieve material outputs that more accurately and responsively converge on one or more of the target properties.

43. The FCC processing assembly of claim 42, further comprising a sample conditioning assembly positioned to one or more of:
  (i) condition the hydrocarbon feedstock sample, prior to supply to the first spectroscopic analyzer, to one or more of filter the hydrocarbon feedstock sample, change a temperature of the hydrocarbon feedstock sample, or degas the hydrocarbon feedstock sample, or
  (ii) condition the unit material sample, prior to supply to the second spectroscopic analyzer, to one or more of filter the unit material sample, change a temperature of the unit material sample, dilute the unit material sample in solvent, or degas the unit material sample, and wherein the sample conditioning assembly comprises one or more of:
- (a) one or more filters comprising filter media positioned to remove one or more of water, particulates, or other contaminants from one or more of the hydrocarbon feedstock sample or the unit material sample,
- (b) a temperature control unit positioned to receive the one or more of the hydrocarbon feedstock sample or the unit material sample and a temperature of the one or more of the hydrocarbon feedstock sample or the unit material sample, thereby to provide a temperature-adjusted sample stream of the one or more of the hydrocarbon feedstock sample or the unit material sample, or
- (c) a degassing unit positioned to degas the one or more of the hydrocarbon feedstock sample or the unit material sample, thereby to provide a degassed sample stream of the one or more of the hydrocarbon feedstock sample or the unit material sample.

* * * * *